US012649150B2

(12) United States Patent
Laderoute et al.

(10) Patent No.: US 12,649,150 B2
(45) Date of Patent: Jun. 9, 2026

(54) ENZYME-DECORATED NANOCATALYSTS

(71) Applicant: Cassiopea LLC, Phoenix, AZ (US)

(72) Inventors: Keith Laderoute, Redwood City, CA (US); Mark P. Andrews, Montreal (CA); Egor Katkov, Montreal (CA); Sally Royal Hamry, Montreal (CA); Janine Mauzeroll, Montreal (CA); John Thomas Marino, Phoenix, AZ (US)

(73) Assignee: Cassiopea LLC, Phoenix, AZ (US)

( * ) Notice: Subject to any disclaimer, the term of this patent is extended or adjusted under 35 U.S.C. 154(b) by 0 days.

(21) Appl. No.: 19/222,494

(22) Filed: May 29, 2025

(65) Prior Publication Data

US 2025/0367648 A1     Dec. 4, 2025

Related U.S. Application Data

(60) Provisional application No. 63/653,187, filed on May 29, 2024.

(51) Int. Cl.
| | |
|---|---|
| *C12P 21/06* | (2006.01) |
| *B01J 31/00* | (2006.01) |
| *B01J 35/40* | (2024.01) |
| *C07K 14/00* | (2006.01) |
| *C12N 1/12* | (2006.01) |
| *C12N 1/20* | (2006.01) |
| *C12N 9/88* | (2006.01) |
| *C12P 3/00* | (2006.01) |
| *C12R 1/89* | (2006.01) |

(52) U.S. Cl.
CPC ............ *B01J 31/003* (2013.01); *B01J 35/40* (2024.01); *C07K 14/00* (2013.01); *C12N 1/12* (2013.01); *C12N 1/20* (2013.01); *C12N 9/88* (2013.01); *C12P 3/00* (2013.01); *C12Y 402/01001* (2013.01); *C07K 2319/00* (2013.01); *C12R 2001/89* (2021.05)

(58) Field of Classification Search
None
See application file for complete search history.

(56) References Cited

U.S. PATENT DOCUMENTS

| | | | |
|---|---|---|---|
| 7,628,995 | B2 | 12/2009 | Bos et al. |
| 9,322,011 | B2 | 4/2016 | Luirink et al. |
| 9,394,344 | B2 | 7/2016 | DeLisa et al. |
| 9,526,775 | B2 | 12/2016 | Feldman et al. |
| 9,764,027 | B2 | 9/2017 | Grandi et al. |
| 2006/0088553 | A1 | 4/2006 | Braun et al. |
| 2007/0166333 | A1 | 7/2007 | Niebla Perez et al. |
| 2010/0092519 | A1 | 4/2010 | Gorringe et al. |
| 2014/0093923 | A1 | 4/2014 | Reppas et al. |
| 2014/0294935 | A1 | 10/2014 | Berthet et al. |
| 2016/0222372 | A1 | 8/2016 | Walper et al. |
| 2017/0080080 | A1 | 3/2017 | Trent et al. |
| 2022/0008529 | A1 | 1/2022 | Alfini et al. |
| 2022/0080035 | A1 | 3/2022 | Park et al. |
| 2023/0035004 | A1 | 2/2023 | Heck et al. |
| 2023/0083394 | A1 | 3/2023 | Delisa et al. |
| 2023/0137821 | A1 | 5/2023 | Alfini et al. |
| 2023/0137914 | A1 | 5/2023 | Di Benedetto et al. |

FOREIGN PATENT DOCUMENTS

| | | | |
|---|---|---|---|
| CA | 3171797 | A1 | 3/2024 |
| EP | 1804834 | B1 | 5/2011 |
| EP | 2279746 | B1 | 10/2013 |
| EP | 2255826 | B1 | 4/2016 |
| EP | 2545068 | B8 | 3/2018 |
| EP | 3762409 | A1 | 1/2021 |
| EP | 3181575 | B1 | 3/2021 |
| EP | 3838918 | A1 | 6/2021 |
| EP | 3312192 | B1 | 2/2023 |
| WO | 2017087811 | A1 | 5/2017 |
| WO | 2019103548 | A2 | 5/2019 |
| WO | 2022112794 | A1 | 6/2022 |
| WO | 2022270872 | A1 | 12/2022 |
| WO | 2023153949 | A1 | 8/2023 |
| WO | 2023232976 | A1 | 12/2023 |
| WO | 2024023265 | A2 | 2/2024 |

OTHER PUBLICATIONS

Thakur et al (ACS Biomaterials Science & Engineering (2022), 8(2), 493-501).*
Matinha-Cardoso et al (Microb Biotechnol. Apr. 14, 2022;15(8):2191-2207).*
Lima et al (Life. Jul. 2020, 10, 129; pp. 1-20).*
Amalia. L. et al. "Functionalization of OMVs for Biocatalytic Applications", Membranes, vol. 13, No. 5,459, Apr. 24, 2023, 13 pages.

(Continued)

*Primary Examiner* — Jennifer E Graser

(74) *Attorney, Agent, or Firm* — Fenwick & West LLP; Hayan Yoon; Payal B. Sud

(57) ABSTRACT

Provided herein are vesicular nanocatalysts decorated on their surface with enzymes, such as for industrial use. More particularly, the nanocatalysts include outer membrane vesicles (OMVs) presenting on their surface carbonic anhydrase or a functional fragment or derivative thereof. Uses, methods of manufacture, and compositions of the nanocatalysts are also disclosed herein.

18 Claims, 9 Drawing Sheets

Specification includes a Sequence Listing.

(56) References Cited

OTHER PUBLICATIONS

Biller et al. "Bacterial Vesicles in Marine Ecosystems", Science, vol. 343, Jan. 12, 2024, 5 pages.

Kim et al. "Engineered Bacterial Outer Membrane Vesicles with Enhanced Functionality", Journal of Molecular Biology, vol. 380, no. Jun. 27, 2008, 31 pages.

Lima S. et al. "Extracellular Vesicles: An Overlooked Secretion System in Cyanobacteria", Life, vol. 10, No. 129, Jul. 31, 2020, 20 pages.

Matinha-Cardoso et al. "Novel protein carrier system based on cyanobacterial nano-sized extracellular vesicles for application in fish", Microbial Biotechnology,vol. 15, No. 8, Apr. 14, 2022, 17 pages.

Patent Cooperation Treaty, International Search Report and Written Opinion, PCT Application No. PCT/US2025/031448, 20 pages.

* cited by examiner

ENZYME-DECORATED NANOCATALYSTS

This application claims the benefit of U.S. Provisional Patent Application No. 63/653,187 filed on May 29, 2024, the entire contents of which are hereby incorporated by reference.

1. SEQUENCE LISTING

The instant application contains a Sequence Listing which has been submitted via Patent Center and is hereby incorporated by reference in its entirety. Said XML copy, created on May 28, 2025, is named 42201-58430WO_SEQLISTING, and is 40,483 bytes in size.

2. FIELD

The present disclosure generally relates to enzyme-decorated vesicular nanocatalysts, such as for industrial use.

3. BACKGROUND

The outer membrane vesicles (OMVs) derived from Gram-negative bacteria have been acknowledged for their biomedical applications, including drug delivery, vaccine development, and bioengineering. They are spherical structures naturally secreted by these bacteria, encompassing an assortment of substances such as proteins, nucleic acids, and lipopolysaccharides—each varying based on the type and state of the parent bacterium. In recent years, technologies have emerged enabling the horizontal gene transfer and genetic manipulation of bacteria to generate bespoke OMVs with desired attributes.

Despite these advances, the engineered OMVs remains vastly underutilized. It is due to several problems that still need to be addressed—for example, the assembly mechanism of OMVs hasn't been fully understood and the separation and purification processes of OMVs are complex and require further studies. In large-scale production, the size of OMVs is not easy to control, and the difference between batches is large. The lack of understanding of the exact assembly mechanism of OMVs results in difficulties in engineering the particles.

4. SUMMARY

The present disclosure concerns outer membrane vesicle (OMV) nanocatalysts presenting on their surface an enzyme. In particular embodiments, the OMV nanocatalysts present carbonic anhydrase or a functional fragment or derivative thereof. The present disclosure further relates to uses of the nanocatalysts, such as for environmental remediation, food technology, and specialty and commodity organic and inorganic chemical synthesis; methods of manufacturing the nanocatalysts; and compositions comprising the nanocatalysts.

In some embodiments, provided herein is an engineered outer membrane vesicle (OMV) comprising a heterologous enzyme presented on the outer surface of the engineered OMV. In some embodiments, the heterologous enzyme is operably linked to a transmembrane protein embedded in the membrane of the engineered OMV to form a fusion protein. In some embodiments, the transmembrane protein is derived from an autotransporter protein (ATP) or an outer membrane protein (OMP).

In some embodiments, according to any of the engineered OMVs described herein, the transmembrane protein is derived from an ATP selected from antigen 43 (Ag43), hemoglobin-binding protease (Hbp), pertactin, extracellular serine protease plasmid-encoded (EspP), IgA1 protease, esterase autotransporter (EstA), adhesion and penetration protein (Hap), adhesin involved in diffuse adherence (AIDA-I), plasmid-encoded toxin (Pet), protease involved in intestinal colonization (Pic), temperature-sensitive hemagglutinin (Tsh), *Shigella* extracellular protein (SepA), and vacuolating cytotoxin A (VacA). In some embodiments, the ATP is Ag43. In some embodiments, the transmembrane protein comprises the amino acid sequence of SEQ ID NO: 8. In some embodiments, the ATP is Hbp. In some embodiments, the transmembrane protein comprises the amino acid sequence of SEQ ID NO: 9.

In some embodiments, according to any of the engineered OMVs described herein, the transmembrane protein is derived from an OMP selected from *Synechococcus* outer membrane protein A (SomA), MipA, and ice nucleation proteins (INPs). In some embodiments, the OMP is SomA. In some embodiments, the transmembrane protein comprises the amino acid sequence of SEQ ID NO: 10. In some embodiments, the OMP is MipA. In some embodiments, the transmembrane protein comprises the amino acid sequence of SEQ ID NO: 11. In some embodiments, the OMP is an INP. In some embodiments, the INP is from *Pseudomonas syringae*. In some embodiments, the transmembrane protein comprises the amino acid sequence of SEQ ID NO: 12.

In some embodiments, according to any of the engineered OMVs described herein, the fusion protein further comprises a linker connecting the heterologous enzyme to the transmembrane protein. In some embodiments, the linker is a peptide linker comprising the amino acid sequence of any one of SEQ ID NOs: 17-19 and 25.

In some embodiments, according to any of the engineered OMVs described herein, the engineered OMV comprises at least about 10 heterologous enzyme molecules presented on its outer surface.

In some embodiments, according to any of the engineered OMVs described herein, the engineered OMV has a diameter of about 50 nm to about 250 nm. In some embodiments, the engineered OMV has a diameter of about 70 nm to about 130 nm.

In some embodiments, according to any of the engineered OMVs described herein, the engineered OMV is obtained from a photosynthetic microorganism. In some embodiments, according to any of the engineered OMVs described herein, the engineered OMV is expressed by a photosynthetic microorganism. In some embodiments, the photosynthetic organism is an engineered photosynthetic organism.

In some embodiments, the photosynthetic microorganism is a gram-negative bacterium. In some embodiments, the gram-negative bacterium is a cyanobacterium. In some embodiments, the cyanobacterium is selected from *Synechocystis* sp., *Synechococcus* sp., *Microcystis aeruginosa, Leptolyngbya boryana, Cyanobium gracile, Phormidium persicinum*, and *Gloeocapsa* sp. In some embodiments, the cyanobacterium is selected from *Synechococcus* sp. PCC 7942, *Synechococcus elongatus* UTEX 2973, and *Synechocystis* sp. PCC 6803. In some embodiments, the photosynthetic microorganism is a eukaryotic microalgae.

In some embodiments, according to any of the engineered OMVs described herein, the heterologous enzyme comprises a carbonic anhydrase (CA) polypeptide or functional fragment thereof. In some embodiments, the CA polypeptide is derived from a thermostable CA. In some embodiments, the thermostable CA is from *Thermosulfurimonas dis-*

*mutans*. In some embodiments, the CA polypeptide comprises the amino acid sequence of SEQ ID NO: 7.

In some embodiments, provided herein is an engineered host cell capable of producing an OMV comprising a heterologous enzyme presented on the outer surface of the OMV, wherein the engineered host cell is a photosynthetic microorganism comprising heterologous nucleic acid encoding a fusion protein comprising the heterologous enzyme operably linked to a transmembrane protein, and wherein the fusion protein is capable of being inserted into the outer membrane of the engineered host cell such that the heterologous enzyme is presented on the outer surface of the engineered host cell.

In some embodiments, according to any of the engineered host cells described herein, the transmembrane protein is derived from an autotransporter protein (ATP) or an outer membrane protein (OMP). In some embodiments, the transmembrane protein is derived from an ATP selected from antigen 43 (Ag43), hemoglobin-binding protease (Hbp), pertactin, extracellular serine protease plasmid-encoded (EspP), IgA1 protease, esterase autotransporter (EstA), adhesion and penetration protein (Hap), adhesin involved in diffuse adherence (AIDA-I), plasmid-encoded toxin (Pet), protease involved in intestinal colonization (Pic), temperature-sensitive hemagglutinin (Tsh), *Shigella* extracellular protein (SepA), and vacuolating cytotoxin A (VacA). In some embodiments, the ATP is Ag43. In some embodiments, the transmembrane protein comprises the amino acid sequence of SEQ ID NO: 8. In some embodiments, the ATP is Hbp. In some embodiments, the transmembrane protein comprises the amino acid sequence of SEQ ID NO: 9.

In some embodiments, according to any of the engineered host cells described herein, the transmembrane protein is derived from an OMP selected from *Synechococcus* outer membrane protein A (SomA), MipA, and ice nucleation proteins (INPs). In some embodiments, the OMP is SomA. In some embodiments, the transmembrane protein comprises the amino acid sequence of SEQ ID NO: 10. In some embodiments, the OMP is MipA. In some embodiments, the transmembrane protein comprises the amino acid sequence of SEQ ID NO: 11. In some embodiments, the OMP is an INP. In some embodiments, the INP is from *Pseudomonas syringae*. In some embodiments, the transmembrane protein comprises the amino acid sequence of SEQ ID NO: 12.

In some embodiments, according to any of the engineered host cells described herein, the fusion protein further comprises a linker connecting the heterologous enzyme to the transmembrane protein. In some embodiments, the linker is a peptide linker comprising the amino acid sequence of any one of SEQ ID NOs: 17-19 and 25. In some embodiments, the linker comprises an amino acid sequence of GGG.

In some embodiments, according to any of the engineered host cells described herein, the fusion protein further comprises a signal peptide capable of targeting the fusion protein to the inner membrane of the engineered host cell. In some embodiments, the signal peptide comprises the amino acid sequence of any one of SEQ ID NOs: 13-16.

In some embodiments, according to any of the engineered host cells described herein, the engineered host cell is a cyanobacterium. In some embodiments, the cyanobacterium is selected from *Synechocystis* sp., *Synechococcus* sp., *Microcystis aeruginosa, Leptolyngbya boryana, Cyanobium gracile, Phormidium persicinum,* and *Gloeocapsa* sp. In some embodiments, the cyanobacterium is selected from *Synechococcus* sp. PCC 7942, *Synechococcus elongatus* UTEX 2973, and *Synechocystis* sp. PCC 6803.

In some embodiments, according to any of the engineered host cells described herein, the engineered host cell is a eukaryotic microalgae.

In some embodiments, according to any of the engineered host cells described herein, the heterologous enzyme comprises a CA polypeptide or functional fragment thereof. In some embodiments, the CA polypeptide is derived from a thermostable CA. In some embodiments, the thermostable CA is from *Thermosulfurimonas dismutans*. In some embodiments, the CA polypeptide comprises the amino acid sequence of SEQ ID NO: 7.

In some embodiments, according to any of the engineered host cells described herein, the heterologous nucleic acid is present extrachromosomally. In some embodiments, the heterologous nucleic acid is a plasmid.

In some embodiments, according to any of the engineered host cells described herein, the heterologous nucleic acid is integrated into the chromosome of the engineered host cell. In some embodiments, the heterologous nucleic acid is integrated into the chromosome by site-specific targeting. In some embodiments, the heterologous nucleic acid is integrated into the chromosome by site-specific targeting using a CRISPR/Cas9 system.

In some embodiments, according to any of the engineered host cells described herein, the heterologous nucleic acid is operably linked to an inducible promoter.

In some embodiments, provided herein is a method of producing an engineered OMV comprising: (a) culturing an engineered host cell according to any of the embodiments described herein under conditions suitable for expression of the fusion protein; and (b) obtaining an OMV produced by the engineered host cell, thereby producing the engineered OMV. In some embodiments, the engineered host cell is cultured in the presence of CO2 and light. In some embodiments, the method further comprises filtering the engineered OMV. In some embodiments, the filtering is performed by ultrafiltration. In some embodiments, the filtering is performed by a membrane bioreactor. In some embodiments, the method further comprises concentrating the engineered OMV.

In some embodiments, provided herein is a nanocatalyst composition comprising an engineered OMV according to any of the embodiments described herein. In some embodiments, the engineered OMV is produced by a method of producing an engineered OMV according to any of the embodiments described herein.

In some embodiments, according to any of the nanocatalyst compositions described herein, the composition comprises the engineered OMV at a concentration greater than about 100 mg/L.

In some embodiments, according to any of the nanocatalyst compositions described herein, the composition comprises the engineered OMV in an amount greater than about 10 g.

In some embodiments, according to any of the nanocatalyst compositions described herein, the composition is not a therapeutic composition.

In some embodiments, provided herein is a nanocatalyst product comprising a nanocatalyst composition according to any of the embodiments described herein in a volume greater than about 1 L In some embodiments, provided herein is a method of reducing $CO_2$ comprising interacting an engineered OMV according to any of the embodiments described herein wherein the heterologous enzyme comprises a carbonic anhydrase (CA) polypeptide or functional fragment thereof with $CO_2$ under a condition suitable for the CA polypeptide or functional fragment thereof to convert $CO_2$ to a catalysis product. In some embodiments, the catalysis product is a metal carbonate. In some embodiments, the engineered OMV is interacted with $CO_2$ in the presence of $H_2O$ and a metal ion under alkaline conditions suitable for (i) the conversion of $CO_2$ to $CO_3^{2-}$ by the CA polypeptide or functional fragment thereof, and (ii) association of $CO_3^{2-}$ with the metal ion to form the metal carbonate. In some embodiments, the metal ion is $Ca^{2+}$, $Mg^{2+}$, $Fe^{2+}$, $Zn^{2+}$, $Cu^{2+}$, $Mn^{2+}$, or $Li^+$.

In some embodiments, according to any of the methods of reducing CO2 described herein, the engineered OMV is interacted with CO2 in air, water, or waste.

In some embodiments, according to any of the methods of reducing CO2 described herein, the method further comprises producing an engineered OMV according to any of the methods described herein. In some embodiments, producing the engineered OMV is carried out in a first reactor and producing the catalysis product is carried out in a second reactor. In some embodiments, the method further comprises isolating engineered OMVs produced in the first reactor and introducing the isolated engineered OMVs into the second reactor. In some embodiments, isolating the engineered OMVs is carried out by filtration.

In some embodiments, provided herein is a system for the production of an engineered OMV according to any of the embodiments described herein, the system comprising: (a) a first reactor configured to receive a microorganism capable of producing the engineered OMV; (b) a receptacle configured to receive the engineered OMV produced in the first reactor and (c) a filtration interface connecting the first reactor to the receptable, wherein the engineered OMV produced in the first reactor is capable of passing through the filtration interface into the receptacle.

In some embodiments, according to any of the systems for the production of an engineered OMV described herein, the first reactor is a photobioreactor configured to receive light, and the microorganism is a photosynthetic microorganism. In some embodiments, the photosynthetic microorganism is a cyanobacterium or a eukaryotic microalga. In some embodiments, the photosynthetic microorganism is an engineered host cell according to any of the embodiments described herein.

In some embodiments, according to any of the systems for the production of an engineered OMV described herein, the first reactor is configured to receive ambient air/$CO_2$.

In some embodiments, according to any of the systems for the production of an engineered OMV described herein, the microorganism in the first reactor is incapable or substantially incapable of passing through the filtration interface into the receptacle.

In some embodiments, according to any of the systems for the production of an engineered OMV described herein, the filtration interface comprises one or more filtration membranes. In some embodiments, the filtration interface comprises at least 2, 3, 4, or 5 filtration membranes. In some embodiments, the one or more filtration membranes are one or more ultrafiltration membranes.

In some embodiments, according to any of the systems for the production of an engineered OMV described herein, the receptacle is configured to receive the engineered OMV: (a) at a concentration greater than about 100 mg/L; (b) in an amount greater than about 10 g; and/or (c) in a volume greater than about 100 mL.

In some embodiments, provided herein is a system for catalyzing the conversion of CO2 and H2O to HCO3– and H+, the system comprising: (a) a first reactor configured to receive a microorganism capable of producing an engineered OMV according to any of the embodiments described herein; (b) a second reactor configured to receive the engineered OMV produced in the first reactor in conditions suitable for carrying out the conversion of CO2 and H2O to HCO3– and H+; and (c) a filtration interface connecting the first reactor to the second reactor, wherein the engineered OMV produced in the first reactor is capable of passing through the filtration interface into the second reactor.

In some embodiments, according to any of the systems for catalyzing the conversion of $CO_2$ and $H_2O$ to $HCO_3^-$ and $H^+$ described herein, the first reactor is a photobioreactor configured to receive light, and the microorganism is a photosynthetic microorganism. In some embodiments, the photosynthetic microorganism is a cyanobacterium or a eukaryotic microalga. In some embodiments, the photosynthetic microorganism is an engineered host cell according to any of the embodiments described herein.

In some embodiments, according to any of the systems for catalyzing the conversion of $CO_2$ and $H_2O$ to $HCO_3^-$ and $H^+$ described herein, the first reactor is configured to receive ambient air/$CO_2$.

In some embodiments, according to any of the systems for catalyzing the conversion of $CO_2$ and $H_2O$ to $HCO_3^-$ and $H^+$ described herein, the second reactor is an alkaline reactor comprising an aqueous composition having a pH greater than about 8.0.

In some embodiments, according to any of the systems for catalyzing the conversion of $CO_2$ and $H_2O$ to $HCO_3^-$ and $H^+$ described herein, the second reactor is configured to receive $CO_2$.

In some embodiments, according to any of the systems for catalyzing the conversion of $CO_2$ and $H_2O$ to $HCO_3^-$ and $H^+$ described herein, the second reactor comprises an aqueous composition comprising a metal ion under conditions suitable for the formation of a metal carbonate comprising the metal ion. In some embodiments, the metal ion is $Ca^{2+}$, $Mg^{2+}$, $Fe^{2+}$, $Zn^{2+}$, $Cu^{2+}$, $Mn^{2+}$, or $Li^+$.

In some embodiments, according to any of the systems for catalyzing the conversion of $CO_2$ and $H_2O$ to $HCO_3^-$ and $H^+$ described herein, the microorganism in the first reactor is incapable or substantially incapable of passing through the filtration interface into the second reactor.

In some embodiments, according to any of the systems for catalyzing the conversion of $CO_2$ and $H_2O$ to $HCO_3^-$ and $H^+$ described herein, the filtration interface comprises one or more filtration membranes. In some embodiments, the filtration interface comprises at least 2, 3, 4, or 5 filtration membranes. In some embodiments, the one or more filtration membranes are one or more ultrafiltration membranes.

In some embodiments, according to any of the systems for catalyzing the conversion of $CO_2$ and $H_2O$ to $HCO_3^-$ and $H^+$ described herein, the second reactor is configure to receive the engineered OMV: (a) at a concentration greater than about 100 mg/L; (b) in an amount greater than about 10 g; and/or (c) in a volume greater than about 100 mL.

5. BRIEF DESCRIPTION OF THE SEVERAL VIEWS OF THE DRAWINGS

These and other features, aspects, and advantages of the present invention will become better understood with regard to the following description, and accompanying drawings, where:

FIG. 1 provides graphical depiction of an OMV nano-catalyst in cross-section and as a sphere showing surface decoration with carbonic anhydrase/CA enzyme (OMV-CA nanocatalysts).

FIG. 2 provides schematic diagram of an exemplary platform for the synthesis, isolation, and function of OMV-CA (carbonic anhydrase) nanocatalysts for carbon capture, storage, and utilization.

Figure 5:
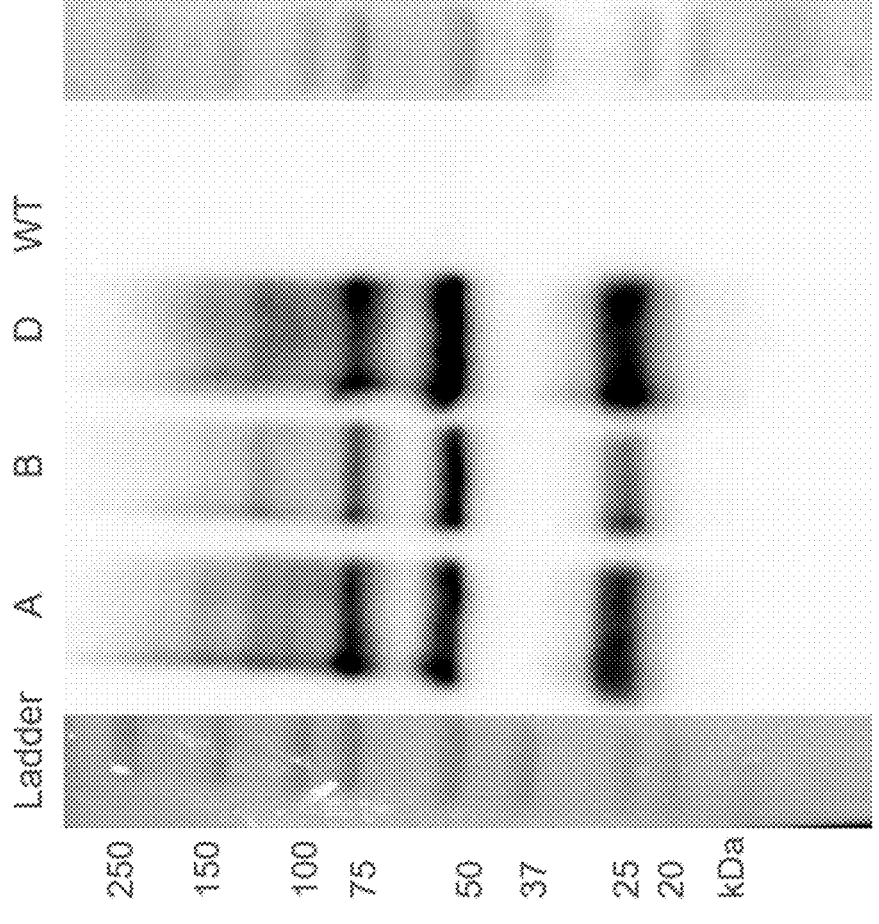

FIG. 5 provides an anti-TdCA immunoblot of whole cell lysates of UTEX 2973 cells transformed with a TdCA-Ag43 construct (78 kDa). LDR/Ladder indicates sized protein standards, the sizes of which are indicated in the margin. WT indicates the wild type UTEX 2973 strain, whereas A, B and D are separate cultures originating from distinct colonies formed following antibiotic selection. Expected sizes of different fusion proteins are (i) TdCA-Ag43 with SP (signal peptide): 84 kDa; (ii) TdCA-Ag43 without SP (signal peptide): 80 kDa; (iii) TdCA: 28 kDa; and (iv) Ag43: 52 kDa.

Figure 6:
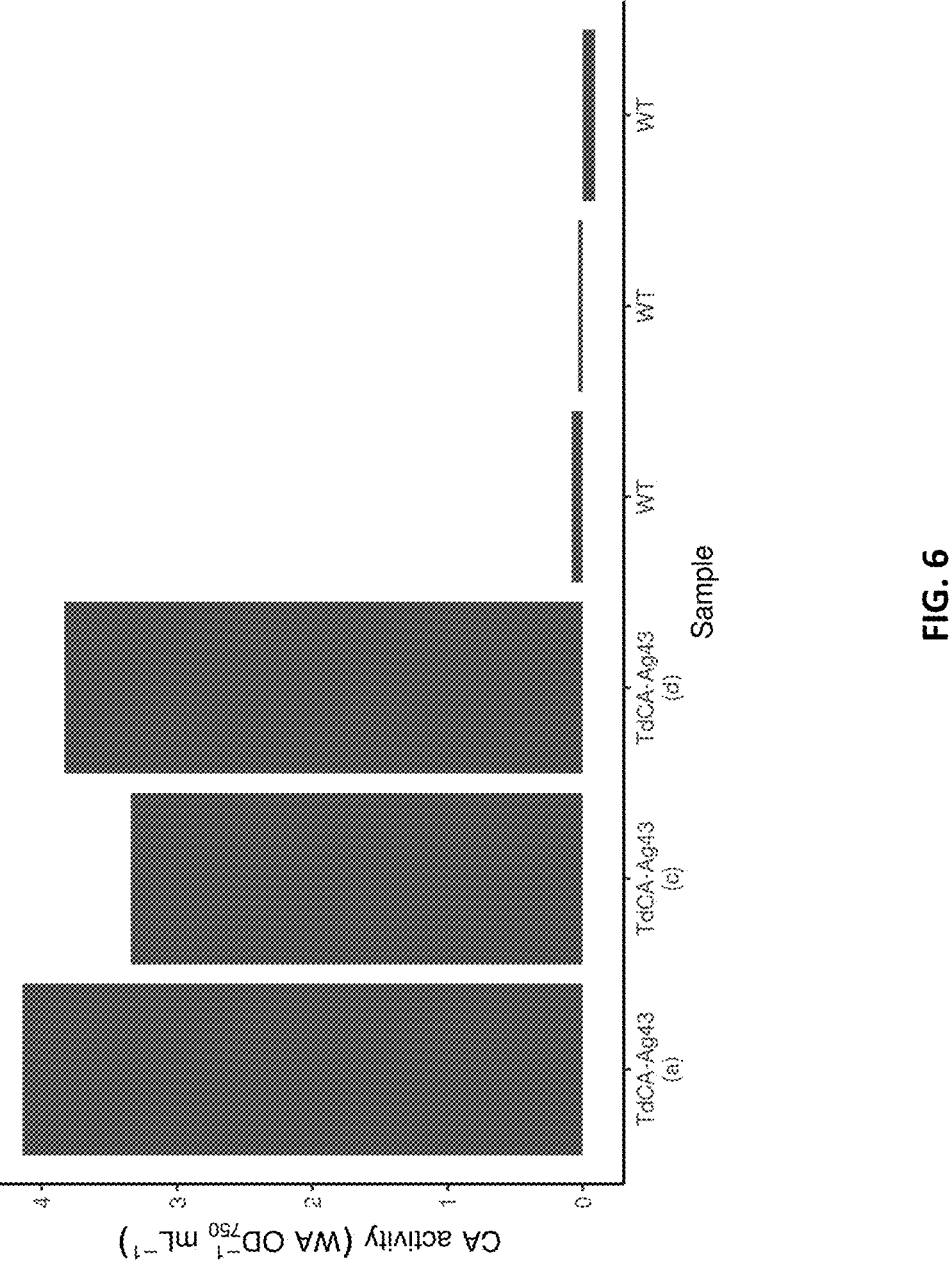

FIG. 6 provides carbonic anhydrase activity assay results of washed whole cyanobacterial cells, corrected for the optical density of the 10× concentrated culture. WT indicates wild type cells, and other samples are distinct transformed cultures (TdCA-Ag43) representing different colonies from an antibiotic selection agar plate.

Figure 7:
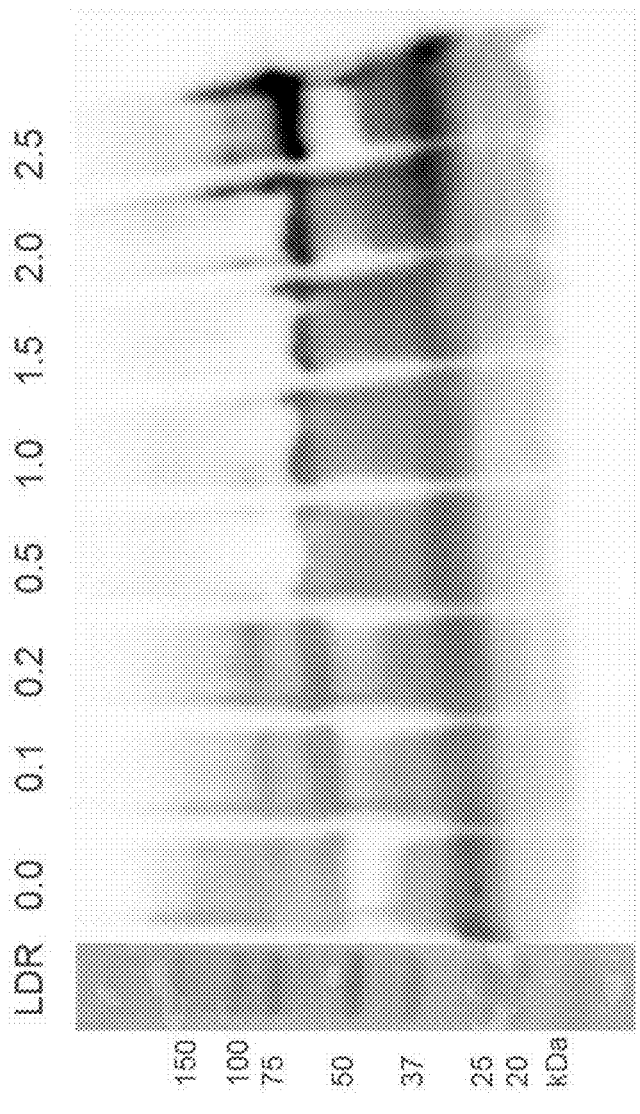

FIG. 7 provides TdCA-Ag43 immunoblotting results for separate treatments of whole cell samples of clonal culture D with proteinase K at different concentrations. The band near 78 kDa, which corresponds to the expected size of the TdCA-Ag43 fusion protein, shows significant decrease in intensity with increasing proteinase K concentrations.

Figure 8:
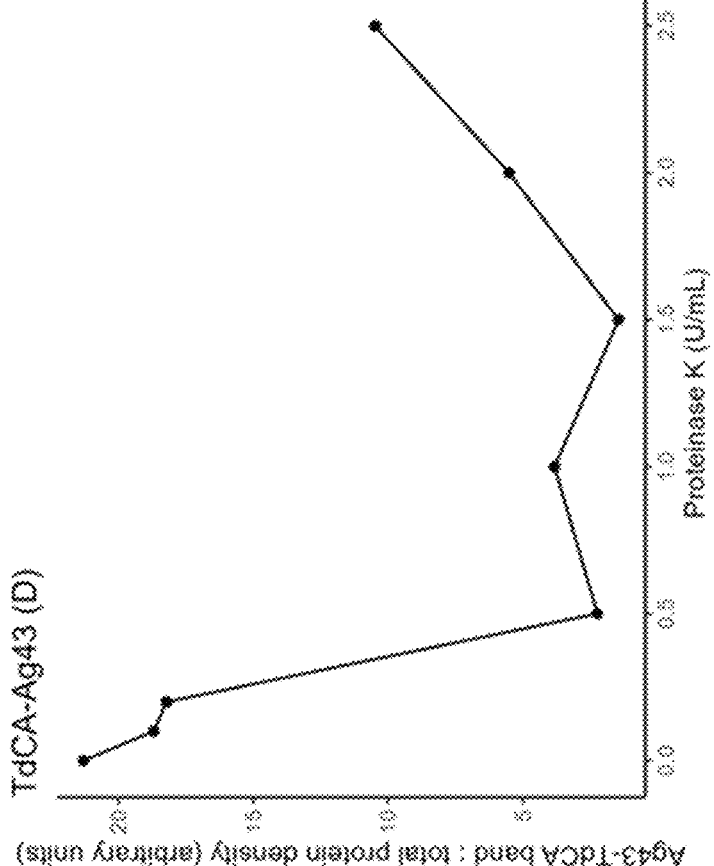

FIG. 8 provides quantitative analysis (measuring band volume/density) of TdCA-Ag43 immunoblotting results for sample D (Units proteinase K/mL) in FIG. 8.

Figure 9:
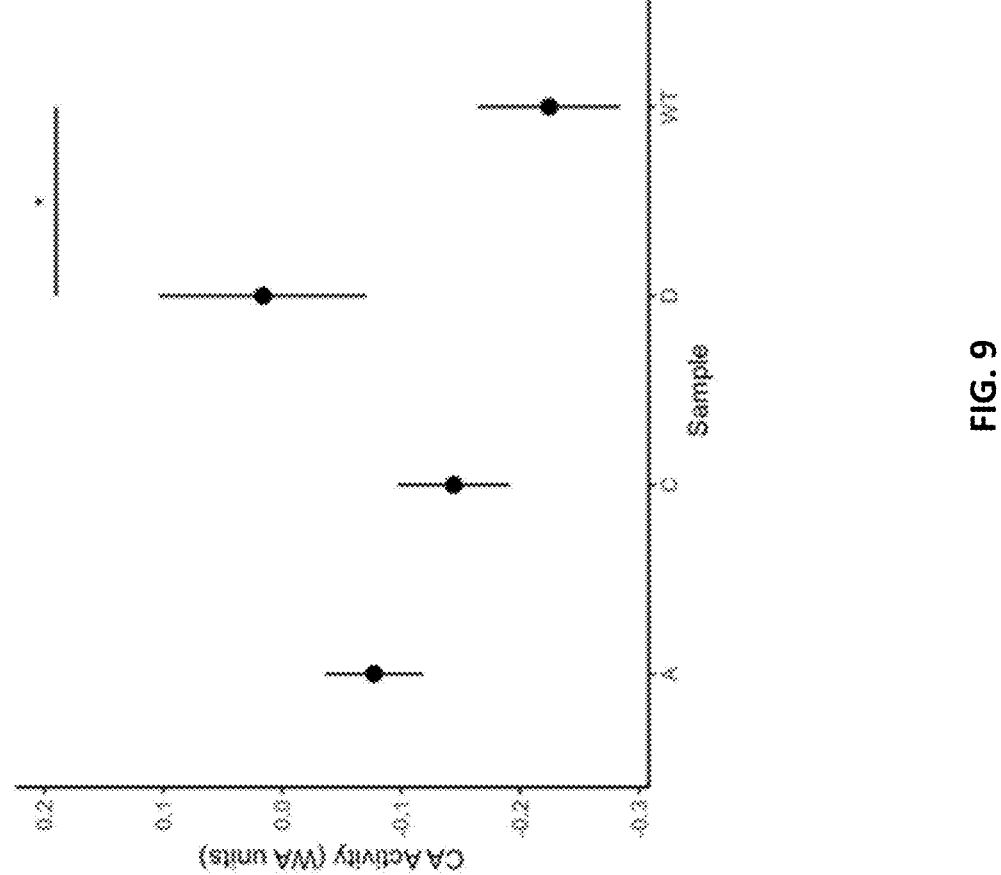

FIG. 9 shows the carbonic anhydrase activity of OMVs from the UTEX 2973 cell supernatants.

6. DETAILED DESCRIPTION OF THE INVENTION

A. Definitions

Unless described otherwise, all technical and scientific terms used herein have the same meaning as is commonly understood by one of ordinary skill in the art. For purposes of interpreting this specification, the following description of terms will apply and whenever appropriate, terms used in the singular will also include the plural and vice versa. All patents, applications, published applications, and other publications are incorporated by reference in their entirety. In the event that any description of terms set forth conflicts with any document incorporated herein by reference, the description of term set forth below shall control.

As used herein, the singular terms "a," "an," and "the" include the plural reference unless the context clearly indicates otherwise. Thus, for example, reference to "a peptide sequence" includes a plurality of such sequences and so forth.

An "autotransporter" is a protein that belongs to the pfam autotransporter family ('Autotransporter' PF03797) and that also is known or predicted to form a beta stem motif. The BETAWRAPPRO method for sequence analysis can be used to predict if the passenger domain of an autotransporter will form a beta stem motif (Junker et al 2006 Proc Natl Acad Sci USA 103(13): 4918-23).

"Beta stem forming sequence" refers to the sequence of a passenger domain of an autotransporter that forms a beta stem structure. The beta stem forming sequence of a passenger can be identified using crystal structure determination. As described above the beta stem forming sequence may alternatively be identified using the M4T homology modeling method (Rykunov et al 2009 J Struct Funct Genomics 10: 95-99) or similar prediction methods.

A "side domain" is a domain that is part of the passenger domain but is not part of the beta stem. Typically, a side domain is located in the passenger domain between two stretches of beta stem forming sequence. A side domain starts at the first amino acid after the preceding beta strand and it ends one amino acid before the starting amino acid of the beta strand following the side domain. The side domain can also be located at the N-terminus of the passenger domain. Autotransporters may have several side domains.

A moiety is "displayed" on an object, such as a cell or vesicle, or the object is "decorated" with the moiety, when it remains associated with the outer membrane of the host cell such that it at least partly protrudes outside the cell. The secreted protein may be attached to the cell membrane or a component that resides therein (such as the translocator domain from an autotransporter) in a covalent or non-covalent manner.

Unless otherwise indicated, the terms "oligonucleotides" and "nucleic acids" are used interchangeably and are written left to right in 5' to 3' orientation; amino acid sequences are written left to right in amino to carboxy orientation, respectively.

A "modification" of an amino acid residue/position refers to a change of a primary amino acid sequence as compared to a starting amino acid sequence, wherein the change results from a sequence alteration involving said amino acid residue/position. For example, typical modifications include substitution of the residue with another amino acid (e.g., a conservative or substantial substitution), insertion of one or more (e.g., generally fewer than 5, 4, or 3) amino acids adjacent to said residue/position, and/or deletion of said residue/position.

The term "sequence identity" refers to a relationship between the sequences of two or more biological molecules (e.g., a pair of polynucleotides or multiple polypeptides), as determined by aligning and comparing the respective sequences. "Percent (%) amino acid sequence identity" with respect to a reference amino acid sequence (e.g., a reference polypeptide) is defined as the percentage of amino acid residues in a candidate sequence that are identical with the amino acid residues in the reference amino acid sequence, after aligning the two sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, or MEGALIGN (DNAStar, Inc.) software. Those skilled in the art can determine appropriate parameters for aligning sequences, including any algorithms needed to achieve maximal alignment over the full length of the sequences being compared.

The term "amino acid" refers to naturally occurring and non-naturally occurring alpha-amino acids, as well as alpha-amino acid analogs and amino acid mimetics that function in a manner similar to the naturally occurring alpha-amino acids. Amino acids may be referred to herein by either their commonly known three letter symbols or by the one-letter symbols recommended by the IUPAC-IUB Biochemical Nomenclature Commission.

The term "variant" when used in relation to a peptide or polypeptide may refer to a peptide or polypeptide comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified sequence. For example, a variant of a polypeptide may result from one or more (such as, for example, about 1 to about 25, about 1 to about 20, about 1 to about 15, about 1 to about 10, or about 1 to about 5) changes to an amino acid sequence of a native or previously unmodified polypeptide. Polypeptide variants may be prepared from the corresponding nucleic acid molecules encoding the variants. In specific embodiments, a variant of a polypeptide retains at least one functional activity of the polypeptide.

A "functional fragment" of a polypeptide will exhibit at least one if not some or all of the biological functions attributed to the intact polypeptide.

The term "fusion," "fuse" or other grammatical variants thereof when used in relation to a peptide or polypeptide refers to the joining of a peptide or polypeptide, or fragment, variant, and/or derivative thereof, with a heterologous peptide or polypeptide.

The term "attenuation" or "attenuate," when used herein, refers to partial (such as, 1%, 2%, 5%, 10%, 20%, 25%, 50%, 75%, 90%, 95%, 99%) and less than complete (i.e., 100%) reduction of a given activity.

The term "inhibition," "inhibit," or "abolish" when used herein, refers to a complete (i.e., 100%) reduction of a given activity. In some embodiments, a complete reduction is manifested as no or insignificantly minimal or ignorable detection of the activity using a method (e.g., assay) that has been established and validated for detecting such activity.

The term "vector" refers to a substance that is used to carry or include a nucleic acid sequence, including for example, a nucleic acid sequence encoding a polypeptide as described herein, in order to introduce a nucleic acid sequence into a host cell. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well known in the art. When two or more nucleic acid molecules are to be co-expressed, both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product, and it is further understood that expression levels can be optimized to obtain sufficient expression using methods well known in the art.

B. Compositions and Methods of Making the Same

The present disclosure provides novel enzyme-decorated OMVs, i.e., OMVs (FIG. 1) engineered to present a heterologous enzyme on the outer surface. Enzymes contemplated for surface presentation include those having a carbonic anhydrase activity, but not limited thereto. As illustrated in further detail herein, enzyme-decorated OMVs can be designed and configured in multiple ways to achieve specific goals.

In one aspect of the present disclosure, provided herein is an engineered OMV comprising a heterologous enzyme presented on the outer surface of the engineered OMV. In some embodiments, the heterologous enzyme is operably linked to a transmembrane protein embedded in the membrane of the engineered OMV to form a fusion protein. In some embodiments, the transmembrane protein is derived from an autotransporter protein (ATP) or an outer membrane protein (OMP).

Thus, in some embodiments, provided herein is an engineered OMV comprising a heterologous enzyme presented on the outer surface of the engineered OMV, wherein the heterologous enzyme is operably linked to a transmembrane protein embedded in the membrane of the engineered OMV to form a fusion protein, and wherein the transmembrane protein is derived from an ATP. In some embodiments, the ATP is selected from antigen 43 (Ag43), hemoglobin-binding protease (Hbp), pertactin, extracellular serine protease plasmid-encoded (EspP), IgA1 protease, esterase autotransporter (EstA), adhesion and penetration protein (Hap), adhesin involved in diffuse adherence (AIDA-I), plasmid-encoded toxin (Pet), protease involved in intestinal colonization (Pic), temperature-sensitive hemagglutinin (Tsh), *Shigella* extracellular protein (SepA), and vacuolating cytotoxin A (VacA). In some specific embodiments, the ATP is Ag43. In some such embodiments, the transmembrane protein comprises the amino acid sequence of SEQ ID NO: 8, or a variant thereof having at least 90% sequence identity thereto. In some such embodiments, the transmembrane protein comprises an amino acid sequence having at least 80%, at least 85%, at least 90%, at least 95%, at least 97%, or at least 99% sequence identity to SEQ ID NO: 8. In yet other specific embodiments, the ATP is Hbp. In some such embodiments, the transmembrane protein comprises the amino acid sequence of SEQ ID NO: 9, or a variant thereof having at least 90% sequence identity thereto. In some such embodiments, the transmembrane protein comprises an amino acid sequence having at least 80%, at least 85%, at least 90%, at least 95%, at least 97%, or at least 99% sequence identity to SEQ ID NO: 9. In some such embodiments, the transmembrane protein comprises the amino acid sequence of SEQ ID NO: 23, or a variant thereof having at least 90% sequence identity thereto. In some such embodiments, the transmembrane protein comprises an amino acid sequence having at least 80%, at least 85%, at least 90%, at least 95%, at least 97%, or at least 99% sequence identity to SEQ ID NO: 23.

In some other embodiments, provided herein is an engineered outer membrane vesicle (OMV) comprising a heterologous enzyme presented on the outer surface of the engineered OMV, wherein the heterologous enzyme is operably linked to a transmembrane protein embedded in the membrane of the engineered OMV to form a fusion protein, and wherein the transmembrane protein is derived from an OMP selected from *Synechococcus* outer membrane protein A (SomA), MipA, and ice nucleation proteins (INPs). In some specific embodiments, the OMP is SomA. In some such embodiments, the transmembrane protein comprises the amino acid sequence of SEQ ID NO: 10, or a variant thereof having at least 90% sequence identity thereto. In some such embodiments, the transmembrane protein comprises an amino acid sequence having at least 80%, at least 85%, at least 90%, at least 95%, at least 97%, or at least 99% sequence identity to SEQ ID NO: 10. In yet other specific embodiments, the OMP is MipA. In some such embodiments, the transmembrane protein comprises the amino acid sequence of SEQ ID NO: 11, or a variant thereof having at least 90% sequence identity thereto. In some such embodiments, the transmembrane protein comprises an amino acid sequence having at least 80%, at least 85%, at least 90%, at least 95%, at least 97%, or at least 99% sequence identity to SEQ ID NO: 11. In yet other specific embodiments, the OMP is an INP. In some such embodiments, the INP is from *Pseudomonas syringae*. In some embodiments, the transmembrane protein comprises the amino acid sequence of SEQ ID NO: 12, or a variant thereof having at least 90% sequence identity thereto. In some such embodiments, the transmembrane protein comprises an amino acid sequence having at least 80%, at least 85%, at least 90%, at least 95%, at least 97%, or at least 99% sequence identity to SEQ ID NO: 12.

In some embodiments, according to any of the engineered OMVs described herein comprising a fusion protein, the fusion protein further comprises a linker connecting the heterologous enzyme to the transmembrane protein. In some embodiments, the linker is a peptide linker comprising the amino acid sequence of any one of SEQ ID NOs: 17-19 and 25.

In some embodiments, according to any of the engineered OMVs described herein, the engineered OMV comprises at least about 10 (including, for example, at least about any of 20, 30, 40, 50, 60, 70, 80, 90, 100, 200, 300, 400, 500, 600, 700, 800, 900, 1000, 2000, 3000, 4000, 5000, or more, including any ranges between any of these values) heterologous enzyme molecules presented on its outer surface.

In some embodiments, according to any of the engineered OMVs described herein, the engineered OMV has a diameter of about 20 nm to about 500 nm, including, for example, about any of 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 400 nm, and 500 nm, including any ranges between any of these values. For example, in some embodiments, the engineered OMV has a diameter of about 50 nm to about 300 nm, about 70 nm to about 200 nm, about 70 nm to about 130 nm, about 80 nm to about 120 nm, about 90 nm to about 110 nm, or about 100 nm.

In some embodiments, according to any of the engineered OMVs described herein, the engineered OMV is obtained from a photosynthetic microorganism. In some specific embodiments, the photosynthetic microorganism is a gram-negative bacterium. In yet other specific embodiments, the photosynthetic microorganism is a eukaryotic microalgae.

Thus, in some embodiments, provided herein is an engineered OMV according to any of the embodiments described here, wherein the engineered OMV is obtained from a gram-negative bacterium. In some embodiments, the gram-negative bacterium is a cyanobacterium. In some specific embodiments, the cyanobacterium is selected from *Synechocystis* sp., *Synechococcus* sp., *Microcystis aeruginosa, Leptolyngbya boryana, Cyanobium gracile, Phormidium persicinum*, and *Gloeocapsa* sp. In some embodiments, the cyanobacterium is selected from *Synechococcus* sp. PCC 7942, *Synechococcus elongatus* UTEX 2973, and *Synechocystis* sp. PCC 6803.

In some embodiments, according to any of the engineered OMVs described herein, the heterologous enzyme comprises a carbonic anhydrase (CA) polypeptide or functional fragment or derivative thereof. For example, in some embodiments, the heterologous enzyme comprises a polypeptide having a carbonic anhydrase activity. In some embodiments, the polypeptide having a carbonic anhydrase activity is derived from a thermostable carbonic anhydrase, such as a carbonic anhydrase from *Thermosulfurimonas dismutans*. In some embodiments, the polypeptide having a carbonic anhydrase activity is a functional fragment of a carbonic anhydrase from *Thermosulfurimonas dismutans* retaining at least some (e.g., at least about 50%, 60%, 70%, 80%, 90%, 91%, 92%, 93%, 94%, 95%, 96%, 97%, 98%, or 99%) of its carbonic anhydrase activity. In some embodiments, the polypeptide having a carbonic anhydrase activity is a functional derivative of a carbonic anhydrase from *Thermosulfurimonas dismutans*, such as a polypeptide having sequence similarity (e.g., at least about any of 70%, 80%, 90%, 91%, 92%, 93%, 94%, 95%, 96%, 97%, 98%, or 99% sequence identity) to a carbonic anhydrase from *Thermosulfurimonas dismutans* and retaining at least some (e.g., at least about 50%, 60%, 70%, 80%, 90%, 91%, 92%, 93%, 94%, 95%, 96%, 97%, 98%, or 99%) of its carbonic anhydrase activity. In some specific embodiments, the polypeptide having a carbonic anhydrase activity comprises the amino acid sequence of SEQ ID NO: 7, or a variant thereof having at least 90% sequence identity thereto.

In some embodiments, provided herein is a nanocatalyst composition comprising an engineered OMV according to any of the embodiments described herein. In some embodiments, the engineered OMV is produced by a method according to any of the embodiments described herein.

In some embodiments, according to any of the nanocatalyst compositions described herein, the nanocatalyst composition comprises the engineered OMV at a concentration greater than about 100 mg/L, including, for example, greater than about any of 200 mg/L, 300 mg/L, 400 mg/L, 500 mg/L, 600 mg/L, 700 mg/L, 800 mg/L, 900 mg/L, 1 g/L, 2 g/L, 3 g/L, 4 g/L, 5 g/L, 6 g/L, 7 g/L, 8 g/L, 9 g/L, 10 g/L, or greater.

In some embodiments, according to any of the nanocatalyst compositions described herein, the nanocatalyst composition comprises the engineered OMV in an amount greater than about 10 g, including, for example, greater than about any of 20 g, 30 g, 40 g, 50 g, 60 g, 70 g, 80 g, 90 g, 100 g, 200 g, 300 g, 400 g, 500 g, or greater.

In some embodiments, according to any of the nanocatalyst compositions described herein, the nanocatalyst composition is not a therapeutic composition. In some embodiments, according to any of the nanocatalyst compositions described herein, the nanocatalyst composition is not a composition of therapeutic quality. In some embodiments, according to any of the nanocatalyst compositions described herein, the nanocatalyst composition is a composition for industrial use.

In some embodiments, provided herein is a nanocatalyst product comprising a nanocatalyst composition according to any of the embodiments described herein. In some embodiments, the nanocatalyst product comprises the nanocatalyst composition in a volume greater than about 100 mL, including, for example, greater than about any of 200 mL, 300 mL, 400 mL, 500 mL, 600 mL, 700 mL, 800 mL, 900 mL, 1 L, 2 L, 3 L, 4 L, 5 L, or greater.

C. Transmembrane Proteins

According to the present disclosure, one approach for presenting a heterologous enzyme on the outer surface of an OMV is to fuse the heterologous enzyme to a transmembrane protein to form a fusion protein in such a way that expression of the fusion protein in a host cell results in the production of OMVs with the fusion protein embedded in their membrane and oriented such that the heterologous enzyme is presented on the outer surface of the OMVs.

D. Autotransporter Proteins (ATPs)

In some embodiments, the transmembrane domain is derived from an autotransporter protein (ATP). In some embodiments, the ATP is selected from antigen 43 (Ag43), hemoglobin-binding protease (Hbp), pertactin, extracellular serine protease plasmid-encoded (EspP), IgA1 protease, esterase autotransporter (EstA), adhesion and penetration protein (Hap), adhesin involved in diffuse adherence (AIDA-I), plasmid-encoded toxin (Pet), protease involved in intestinal colonization (Pic), temperature-sensitive hemagglutinin (Tsh), *Shigella* extracellular protein (SepA), and vacuolating cytotoxin A (VacA).

In some embodiments, the transmembrane domain is derived from porins, ice-nucleation proteins (INP), or pilins.

E. Outer Membrane Proteins (OMPs)

In some embodiments, the transmembrane domain is derived from an outer membrane protein (OMP). In some embodiments, the OMP is selected from *Synechococcus* outer membrane protein A (SomA), MipA, and ice nucleation proteins (INPs).

In some embodiments, the INP is a InaZ derived from *Pseudomonas syringae*. In some embodiments, the INP is derived from *Erwinia herbicola* or *Xanthomonas campestris*.

In some embodiments, the OMP is MipA.

In some embodiment, the OMP is a Ton-B-dependent transporter (TBDTs). In some embodiments, the TBDts are selected from ferric enterobactin transporter and vitamin B12 transporter.

F. Carbonic Anhydrase

According to the present disclosure, the engineered OMVs may be employed to catalyze the conversion of $CO_2$ and $H_2O$ to $HCO_3^-$ and $H^+$, a reaction catalyzed by the metalloenzyme carbonic anhydrase. A non-limiting example of this conversion is provided in FIG. 2.

In some embodiments, an engineered OMV according to any of the embodiments described herein comprises a fusion protein comprising a polypeptide have a carbonic anhydrase activity.

Carbonic anhydrases (CAs) are metalloenzymes that catalyze the conversion of $CO_2$ to bicarbonate ions and protons, which is used by cells to control pH and $CO_2$.

In some embodiments, the heterologous enzyme comprises a polypeptide having a carbonic anhydrase activity. In some embodiments, the polypeptide having a carbonic anhydrase activity is derived from a thermostable carbonic anhydrase, such as a carbonic anhydrase from *Thermosulfurimonas dismutans*. In some embodiments, the polypeptide having a carbonic anhydrase activity is a functional fragment of a carbonic anhydrase from *Thermosulfurimonas dismutans* retaining at least some (e.g., at least about 50%, 60%, 70%, 80%, 90%, 91%, 92%, 93%, 94%, 95%, 96%, 97%, 98%, or 99%) of its carbonic anhydrase activity. In some embodiments, the polypeptide having a carbonic anhydrase activity is a functional derivative of a carbonic anhydrase from *Thermosulfurimonas dismutans*, such as a polypeptide having sequence similarity (e.g., at least about any of 70%, 80%, 90%, 91%, 92%, 93%, 94%, 95%, 96%, 97%, 98%, or 99% sequence identity) to a carbonic anhydrase from *Thermosulfurimonas dismutans* and retaining at least some (e.g., at least about 50%, 60%, 70%, 80%, 90%, 91%, 92%, 93%, 94%, 95%, 96%, 97%, 98%, or 99%) of its carbonic anhydrase activity. In some specific embodiments, the polypeptide having a carbonic anhydrase activity comprises the amino acid sequence of SEQ ID NO: 7, or a variant thereof having at least 90% sequence identity thereto.

In some embodiments, a carbonic anhydrase (CA) can function at high temperatures (over 60° C.) from the bacterium *Thermosulfurimonas dismutan*.

In some embodiments, the carbonic anhydrase (CA) enzyme is selected from one or more of the following: aCA; (3CA; yCA; 6CA; (CA; r1CA; OCA; and LCA. In some embodiments, the CA enzyme is selected from one or more of: *Gracilariopsis chorda* CA (NBIV01000047.1); 004846, ATCA1_ARATH; F4IHR4, ATCA2_ARATH; Q9FYE3, ATCA3_ARATH; F4JI K2, ATCA4_ARATH; F4HUC4, ATCA5_ARATH; Q9SUB4, ATCA6_ARATH; Q8L817, ATCA7_ARATH; Q9FM99, ATCA8_ARATH; P27140, BCA1_ARATH; A8XKVO, BCA1_CAEBR; Q22460, BCA1_CAEEL; P42737, BCA2_ARATH; Q9ZUC2, BCA3_ARATH; Q94CE4, BCA4_ARATH; Q94CE3, BCA5_ARATH; Q9C6F5, BCA6_ARATH; 043570, CAH12_HUMAN; Q8CI85, CAH12_MOUSE; Q9MZ30, CAH12_RABIT; Q8N1Q1, CAH13_HUMAN; Q9D6N1, CAH13_MOUSE; Q9ULX7, CAH14_HUMAN; Q9WVT6, CAH14_MOUSE; Q99N23, CAH15_MOUSE; Q1LZA1, CAH1_BOVIN; P83299, CAH1_CHIHA; P20507, CAH1_CHLRE; P46512, CAH1_FLALI; Q7M316, CAH1_GORGO; P00917, CAH1_HORSE; P00915, CAH1_HUMAN; B3A0P2, CAH1_LOTGI; P00916, CAH1_MACMU; P35217, CAH1_MACNE; Q8HY33, CAH1_MONDO; P13634, CAH1_MOUSE; Q7M317, CAH1_PANTR; P07452, CAH1_RABIT; BOBNN3, CAH1_RAT; P48282, CAH1_SHEEP; P00921, CAH2_BOVIN; P07630, CAH2_CHICK; P24258, CAH2_CHLRE; P46513, CAH2_FLALI; P00918, CAH2_HUMAN; B3A0Q6, CAH2_LOTGI; P00920, CAH2_MOUSE; P00919, CAH2_RABIT; P27139, CAH2_RAT; P00922, CAH2_SHEEP; Q8UWA5, CAH2_TRIHK; Q3SZX4, CAH3_BOVIN; Q27504, CAH3_CAEEL; P07450, CAH3_HORSE; P07451, CAH3_HUMAN; P16015, CAH3_MOUSE; Q55154, CAH3_PIG; P14141, CAH3_RAT; Q95323, CAH4_BOVIN; P22748, CAH4_HUMAN; Q64444, CAH4_MOUSE; P48283, CAH4_RABIT; P48284, CAH4_RAT; P35218, CAH5A_HUMAN; P23589, CAH5A_MOUSE; P43165, CAH5A_RAT; Q9Y2DO, CAH5B_HUMAN; Q9QZAO, CAH5B_MOUSE; Q66HG6, CAH5B_RAT; Q10462, CAH5_CAEEL; P18915, CAH6_BOVIN; Q865CO3 CAH6_CANLF; P23280, CAH6_HUMAN; P18761, CAH6_MOUSE; P08060, CAH6_SHEEP; P43166, CAH7_HUMAN; Q9ERQ8, CAH7_MOUSE; Q16790, CAH9_HUMAN; Q8VHB5, CAH9_MOUSE; P40880, CAHC_HORVU; P17067, CAHC_PEA; P16016, CAHC_SPIOL; P27141, CAHC_TOBAC; P46510, CAHX_FLABI; P46511, CAHX_F-LABR; P46281, CAHX_FLAPR; Q92051, CAHZ_DANRE; B8V7P3, CAH_ACRMI; P54212, CAH_DUNSA; 052535, CAH_KLEPN; P84537, CAH_LOBCS; Q57752, CAH_METJA; P40881, CAH_METTT; Q50940, CAH_NEIGO; P94170, CAH_NOSS1; Q6DAJ6, CAH_PE-CAS; 052538, CAH_PECCA; Q5AJ71, CAN_CANAL; P61517, CAN_ECOLI; Q5BCC5, CAN_EMENI; P45148, CAN_HAEIN; 094255, CAN_SCHPO; P61518, CAN_SHIFL; P53615, CAN_YEAST; Q8YYI3, CCMM_NOSS1; Q8DKB5, CCMM_THEVB; 085042, CSOCA_HALNC; Q31HD6, CSOCA_HYDCU; Q7TTT8, CSOCA_PARMW; Q7V6G1, CSOCA_PROMM; Q7V2C7, CSOCA_PROMP; POABFO, CYNT_EC057; POABE9, CYNT_ECOLI; Q9ZN54, CYNT_HELPJ; 024855, CYNT_HELPY; A0R566, CYNT_MYCS2; Q9I262, CYNT_PSEAE; P83329, CYNT_STRTR; P27134, CYNT_SYNE7; Q54735, CYNT_SYNY3; Q75N34, DB3S_DIOP0; A7MAQ2, DIOA3_DIOJA; Q9NL38, MA66_PINMA; AOZSF6, MAC1_CRANI; AOZSF7, MAC2_CRANI; AOZSF2, MAF_PINFU; AOZSF3, MAM_PINMA; Q27908, MANA_PINFU; AOZSF4, MAP1_MIZYE; AOZSF5, MAP2_MIZYE; P64798, MTCA1_MYCBO; P9WPJ6, MTCA1_MYCTO; P9WPJ7, MTCA1_MYCTU; P9WPJ8, MTCA2_MYCTO; P9WPJ9, MTCA2_MYCTU; Q84UV8, NEC3_NICLS; 034872, YTIB_BACSU; NBIV01000047.1; and 006983, YVDA_BACSU. Non-limiting examples of calcium anhydrase enzymes can be found in Canadian Application Publication No.: CA3171797, which is hereby incorporated by reference in its entirety.

G. Examples of Fusion Proteins

In some embodiments, provided herein are fusion proteins according to any of the embodiments described herein comprising a heterologous enzyme and a transmembrane protein useful for presentation of the heterologous enzyme on the outer surface of an OMV.

In some embodiments, the fusion protein comprises, from N-terminus to C-terminus, a polypeptide having carbonic anhydrase activity and a transmembrane protein derived from an autotransporter protein (ATP). In some embodiments, the polypeptide having carbonic anhydrase activity comprises the amino acid sequence of SEQ ID NO: 7, or a variant thereof having at least about 90%, 91%, 92%, 93%, 94%, 95%, 96%, 97%, 98%, or 99% sequence identity thereto. In some embodiments, the transmembrane protein comprises the amino acid sequence of SEQ ID NO: 8 or 9, or a variant thereof having at least about 90%, 91%, 92%, 93%, 94%, 95%, 96%, 97%, 98%, or 99% sequence identity thereto. In some embodiments, the transmembrane protein comprises the amino acid sequence of SEQ ID NO: 10, or a variant thereof having at least about 90%, 91%, 92%, 93%, 94%, 95%, 96%, 97%, 98%, or 99% sequence identity thereto. In some embodiments, the fusion protein further comprises a peptide linker connecting the polypeptide having carbonic anhydrase activity to the transmembrane protein. In some embodiments, the peptide linker comprises the amino acid sequence of SEQ ID NO: 17. In some embodiments, the fusion protein further comprises an N-terminal signal peptide capable of targeting the fusion protein to the inner membrane of a host cell. In some embodiments, the signal peptide comprises the amino acid sequence of any one of SEQ ID NOs: 13-15. In some embodiments, the signal peptide comprises the amino acid sequence of SEQ ID NO: 22.

Accordingly, in some embodiments, provided herein is a fusion protein comprising the amino acid sequence of SEQ ID NO: 1. In some embodiments, provided herein is a fusion protein comprising an amino acid sequence having at least about 70%, 75%, 80%, 85%, 90%, 95%, 96%, 97%, 98%, or 99% identity to SEQ ID NO: 1. In some embodiments, provided herein is a fusion protein comprising an amino acid having at least about 90%, 91%, 92%, 93%, 94%, 95%, 96%, 97%, 98%, or 99% identity to SEQ ID NO: 1.

In some other embodiments, provided herein is a fusion protein comprising the amino acid sequence of SEQ ID NO: 2. In some embodiments, provided herein is a fusion protein comprising an amino acid sequence having at least about 70%, 75%, 80%, 85%, 90%, 95%, 96%, 97%, 98%, or 99% identity to SEQ ID NO: 2. In some embodiments, provided herein is a fusion protein comprising an amino acid sequence having at least about 90%, 91%, 92%, 93%, 94%, 95%, 96%, 97%, 98%, or 99% identity to SEQ ID NO: 2.

In yet some other embodiments, provided herein is a fusion protein comprising the amino acid sequence of SEQ ID NO: 3. In some embodiments, provided herein is a fusion protein comprising an amino acid sequence at least about 70%, 75%, 80%, 85%, 90%, 95%, 96%, 97%, 98%, or 99% identity to SEQ ID NO: 3. In some embodiments, provided herein is a fusion protein comprising an amino acid sequence having at least about 90%, 91%, 92%, 93%, 94%, 95%, 96%, 97%, 98%, or 99% identity to SEQ ID NO: 3.

In some embodiments, the fusion protein comprises, from N-terminus to C-terminus, a transmembrane protein derived from an outer membrane protein (OMP) and a polypeptide having carbonic anhydrase activity. In some embodiments, the polypeptide having carbonic anhydrase activity comprises the amino acid sequence of SEQ ID NO: 7, or a variant thereof having at least about 90%, 91%, 92%, 93%, 94%, 95%, 96%, 97%, 98%, or 99% sequence identity thereto. In some embodiments, the transmembrane protein comprises the amino acid sequence of any one of SEQ ID NOs: 10-12, or a variant thereof having at least about 90%, 91%, 92%, 93%, 94%, 95%, 96%, 97%, 98%, or 99% sequence identity thereto. In some embodiments, the fusion protein further comprises a peptide linker connecting the polypeptide having carbonic anhydrase activity to the transmembrane protein. In some embodiments, the peptide linker comprises the amino acid sequence of SEQ ID NO: 18 or 19. In some embodiments, the fusion protein further comprises an N-terminal signal peptide capable of targeting the fusion protein to the inner membrane of a host cell. In some embodiments, the signal peptide comprises the amino acid sequence of SEQ ID NO: 16.

Accordingly, in some embodiments, provided herein is a fusion protein comprising the amino acid sequence of SEQ ID NO: 4. In some embodiments, provided herein is a fusion protein comprising an amino acid sequence having at least about 70%, 75%, 80%, 85%, 90%, 95%, 96%, 97%, 98%, or 99% identity to SEQ ID NO: 4. In some embodiments, provided herein is a fusion protein comprising an amino acid sequence having at least about 90%, 91%, 92%, 93%, 94%, 95%, 96%, 97%, 98%, or 99% identity to SEQ ID NO: 4.

In some other embodiments, provided herein is a fusion protein comprising the amino acid sequence of SEQ ID NO: 5. In some embodiments, provided herein is a fusion protein comprising an amino acid sequence having at least about 70%, 75%, 80%, 85%, 90%, 95%, 96%, 97%, 98%, or 99% identity to SEQ ID NO: 5. In some embodiments, provided herein is a fusion protein comprising an amino acid sequence having at least about 90%, 91%, 92%, 93%, 94%, 95%, 96%, 97%, 98%, or 99% identity to SEQ ID NO: 5.

In yet some other embodiments, provided herein is a fusion protein comprising the amino acid sequence of SEQ ID NO: 6. In some embodiments, provided herein is a fusion protein comprising an amino acid sequence having at least about 70%, 75%, 80%, 85%, 90%, 95%, 96%, 97%, 98%, or 99% identity to SEQ ID NO: 6. In some embodiments, provided herein is a fusion protein comprising an amino acid sequence having at least about 90%, 91%, 92%, 93%, 94%, 95%, 96%, 97%, 98%, or 99% identity to SEQ ID NO: 6.

In yet some other embodiments, provided herein is a fusion protein comprising the amino acid sequence of SEQ ID NO: 20. In some embodiments, provided herein is a fusion protein comprising an amino acid sequence having at least about 70%, 75%, 80%, 85%, 90%, 95%, 96%, 97%, 98%, or 99% identity to SEQ ID NO: 20. In some embodiments, provided herein is a fusion protein comprising an amino acid sequence having at least about 90%, 91%, 92%, 93%, 94%, 95%, 96%, 97%, 98%, or 99% identity to SEQ ID NO: 20.

In yet some other embodiments, provided herein is a fusion protein comprising the amino acid sequence of SEQ ID NO: 21. In some embodiments, provided herein is a fusion protein comprising an amino acid sequence having at least about 70%, 75%, 80%, 85%, 90%, 95%, 96%, 97%, 98%, or 99% identity to SEQ ID NO: 21. In some embodiments, provided herein is a fusion protein comprising an amino acid sequence having at least about 90%, 91%, 92%, 93%, 94%, 95%, 96%, 97%, 98%, or 99% identity to SEQ ID NO: 21.

In yet some other embodiments, provided herein is a nucleic acid encoding a fusion protein comprising the nucleotide sequence of SEQ ID NO: 24. In some embodiments, provided herein is a nucleic acid encoding a fusion protein comprising a nucleotide sequence having at least about 70%, 75%, 80%, 85%, 90%, 95%, 96%, 97%, 98%, or 99% identity to SEQ ID NO: 24. In some embodiments, provided herein is a nucleic acid encoding a fusion protein comprising a nucleotide sequence having at least about 90%, 91%, 92%, 93%, 94%, 95%, 96%, 97%, 98%, or 99% identity to SEQ ID NO: 21.

H. Preparation of Engineered OMVs

Enzyme-decorated OMVs may be produced by culturing cells transformed or transfected with nucleic acid encoding the enzyme or a fusion protein comprising the enzyme. Polynucleotide sequences encoding polypeptide components of the engineered OMVs of the present disclosure can be obtained using standard recombinant techniques. In some embodiments, polynucleotides can be synthesized using nucleotide synthesizer or PCR techniques. Once obtained, sequences encoding the polypeptides are inserted into a recombinant vector capable of replicating and expressing heterologous polynucleotides in host cells. Many vectors that are available and known in the art can be used for the purpose of the present disclosure. Selection of an appropriate vector will depend mainly on the size of the nucleic acids to be inserted into the vector and the particular host cell to be transformed with the vector. Host cells are transformed with the above-described expression vectors and cultured in conventional nutrient media modified as appropriate for inducing promoters, selecting transformants, or amplifying the genes encoding the desired sequences. OMVs produced by the host cells can be purified using standard purification methods as known in the art.

I. Engineered Host Cells

In one aspect of the present disclosure, provided herein is an engineered host cell capable of producing an OMV comprising a heterologous enzyme presented on the outer surface of the OMV, wherein the engineered host cell is a photosynthetic microorganism comprising heterologous nucleic acid encoding a fusion protein comprising the heterologous enzyme operably linked to a transmembrane protein, and wherein the fusion protein is capable of being inserted into the outer membrane of the engineered host cell such that the heterologous enzyme is presented on the outer surface of the engineered host cell.

Thus, in some embodiments, provided herein is an engineered host cell capable of producing an OMV comprising a heterologous enzyme presented on the outer surface of the OMV, wherein the engineered host cell is a photosynthetic microorganism comprising heterologous nucleic acid encoding a fusion protein comprising the heterologous enzyme operably linked to a transmembrane protein, wherein the fusion protein is capable of being inserted into the outer membrane of the engineered host cell such that the heterologous enzyme is presented on the outer surface of the engineered host cell, and wherein the transmembrane protein is derived from an ATP. In some embodiments, the ATP is selected from antigen 43 (Ag43), hemoglobin-binding protease (Hbp), pertactin, extracellular serine protease plasmid-encoded (EspP), IgA1 protease, esterase autotransporter (EstA), adhesion and penetration protein (Hap), adhesin involved in diffuse adherence (AIDA-I), plasmid-encoded toxin (Pet), protease involved in intestinal colonization (Pic), temperature-sensitive hemagglutinin (Tsh), *Shigella* extracellular protein (SepA), and vacuolating cytotoxin A (VacA). In some specific embodiments, the ATP is Ag43. In some such embodiments, the transmembrane protein comprises the amino acid sequence of SEQ ID NO: 8, or a variant thereof having at least about 90%, 91%, 92%, 93%, 94%, 95%, 96%, 97%, 98%, or 99% sequence identity thereto. In yet other specific embodiments, the ATP is Hbp. In some such embodiments, the transmembrane protein comprises the amino acid sequence of SEQ ID NO: 9, or a variant thereof having at least about 90%, 91%, 92%, 93%, 94%, 95%, 96%, 97%, 98%, or 99% sequence identity thereto.

In some other embodiments, provided herein is an engineered host cell capable of producing an OMV comprising a heterologous enzyme presented on the outer surface of the OMV, wherein the engineered host cell is a photosynthetic microorganism comprising heterologous nucleic acid encoding a fusion protein comprising the heterologous enzyme operably linked to a transmembrane protein, wherein the fusion protein is capable of being inserted into the outer membrane of the engineered host cell such that the heterologous enzyme is presented on the outer surface of the engineered host cell, and wherein the transmembrane protein is derived from an OMP selected from *Synechococcus* outer membrane protein A (SomA), MipA, and ice nucleation proteins (INPs). In some specific embodiments, the OMP is SomA. In some such embodiments, the transmembrane protein comprises the amino acid sequence of SEQ ID NO: 10, or a variant thereof having at least about 90%, 91%, 92%, 93%, 94%, 95%, 96%, 97%, 98%, or 99% sequence identity thereto. In yet other specific embodiments, the OMP is MipA. In some such embodiments, the transmembrane protein comprises the amino acid sequence of SEQ ID NO: 11, or a variant thereof having at least about 90%, 91%, 92%, 93%, 94%, 95%, 96%, 97%, 98%, or 99% sequence identity thereto. In yet other specific embodiments, the OMP is an INP. In some such embodiments, the INP is from *Pseudomonas syringae*. In some embodiments, the transmembrane protein comprises the amino acid sequence of SEQ ID NO: 12, or a variant thereof having at least about 90%, 91%, 92%, 93%, 94%, 95%, 96%, 97%, 98%, or 99% sequence identity thereto.

In some embodiments, according to any of the engineered host cells described herein, the fusion protein further comprises a linker connecting the heterologous enzyme to the transmembrane protein. In some embodiments, the linker is a peptide linker comprising the amino acid sequence of any one of SEQ ID NOs: 17-19 and 25.

In some embodiments, according to any of the engineered host cells described herein, the fusion protein further comprises a signal peptide capable of targeting the fusion protein to the inner membrane of the engineered host cell. In some embodiments, the signal peptide comprises the amino acid sequence of any one of SEQ ID NOs: 13-16.

In some embodiments, according to any of the engineered host cells described herein, the engineered host cell is a gram-negative bacterium. In some embodiments, the gram-negative bacterium is a cyanobacterium. In some specific embodiments, the cyanobacterium is selected from *Synechocystis* sp., *Synechococcus* sp., *Microcystis aeruginosa*, *Leptolyngbya boryana*, *Cyanobium gracile*, *Phormidium persicinum*, and *Gloeocapsa* sp. In some embodiments, the cyanobacterium is selected from *Synechococcus* sp. PCC 7942, *Synechococcus elongatus* UTEX 2973, and *Synechocystis* sp. PCC 6803.

In some embodiments, according to any of the engineered host cells described herein, the engineered host cell is a eukaryotic microalgae. In some embodiments, the microalgae is selected from one or more of: *Dunaliella; Tetraselmis; Chlorella*; and *Chlamydomonas*. The microalgae may be selected from one or more of: *Chlorella vulgaris; Thalassiosira pseudonana; Isochrysis* sp.; *Nannochloropsis* sp.; *Tetraselmis* sp.; *Chaetoceros muelleri; Thalassiosira weissflogii; Pavlova* sp.; *Karenia brevis; Skeletonema* sp.; *Chaetoceros* grad/is; *Chaetoceros calcitrans; Haematococcus pluvialis; Spirulina* sp.; *Chlamydomonas* sp.; *Chlorella* sp.; *Euhalothece* sp. (alkalihalophilic cyanobacterium).

In some embodiments, according to any of the engineered host cells described herein, the heterologous enzyme comprises a carbonic anhydrase (CA) polypeptide or functional fragment or derivative thereof. For example, in some embodiments, the heterologous enzyme comprises a polypeptide having a carbonic anhydrase activity. In some embodiments, the polypeptide having a carbonic anhydrase activity is derived from a thermostable carbonic anhydrase, such as a carbonic anhydrase from *Thermosulfurimonas dismutans*. In some embodiments, the polypeptide having a carbonic anhydrase activity is a functional fragment of a carbonic anhydrase from *Thermosulfurimonas dismutans* retaining at least some (e.g., at least about 50%, 60%, 70%, 80%, 90%, 91%, 92%, 93%, 94%, 95%, 96%, 97%, 98%, or 99%) of its carbonic anhydrase activity. In some embodiments, the polypeptide having a carbonic anhydrase activity is a functional derivative of a carbonic anhydrase from *Thermosulfurimonas dismutans*, such as a polypeptide having sequence similarity (e.g., at least about any of 70%, 80%, 90%, 91%, 92%, 93%, 94%, 95%, 96%, 97%, 98%, or 99% sequence identity) to a carbonic anhydrase from *Thermosulfurimonas dismutans* and retaining at least some (e.g., at least about 50%, 60%, 70%, 80%, 90%, 91%, 92%, 93%, 94%, 95%, 96%, 97%, 98%, or 99%) of its carbonic anhydrase activity. In some specific embodiments, the polypeptide having a carbonic anhydrase activity comprises the amino acid sequence of SEQ ID NO: 7, or a variant thereof having at least 90% sequence identity thereto.

In some embodiments, according to any of the engineered host cells described herein, the heterologous nucleic acid is present extrachromosomally. In some embodiments, the heterologous nucleic acid is a plasmid.

In some embodiments, according to any of the engineered host cells described herein, the heterologous nucleic acid is integrated into the chromosome of the engineered host cell. In some embodiments, the heterologous nucleic acid is integrated into the chromosome by site-specific targeting. In some embodiments, the heterologous nucleic acid is integrated into the chromosome by site-specific targeting using a CRISPR/Cas9 system.

In some embodiments, according to any of the engineered host cells described herein, the heterologous nucleic acid is operably linked to an inducible promoter.

Accordingly, in some embodiments, provided herein is a method of producing an engineered OMV comprising (a) culturing an engineered host cell according to any one of the embodiments described herein under conditions suitable for expression of the fusion protein; and (b) obtaining an OMV produced by the engineered host cell, thereby producing the engineered OMV. In some embodiments, he engineered host cell is cultured in the presence of $CO_2$ and light. In some embodiments, the method further comprises filtering the engineered OMV. In some embodiments, the filtering is performed by ultrafiltration. In some embodiments, the filtering is performed by a membrane bioreactor. In some embodiments, the method further comprises concentrating the engineered OMV.

J. Manufacturing Systems

In one aspect of the present disclosure, provided herein is a system capable of producing an engineered OMV according to any of the embodiments described herein. In some embodiments, the system is capable of producing a composition comprising a plurality of the engineered OMVs. In some embodiments, the composition is suitable for use in an industrial application. For example, in some embodiments, the composition (a) comprises the engineered OMV at a concentration greater than about 100 mg/L (including, for example, greater than about any of 200 mg/L, 300 mg/L, 400 mg/L, 500 mg/L, 600 mg/L, 700 mg/L, 800 mg/L, 900 mg/L, 1 g/L, 2 g/L, 3 g/L, 4 g/L, 5 g/L, 6 g/L, 7 g/L, 8 g/L, 9 g/L, 10 g/L, or greater); (b) comprises the engineered OMV in an amount greater than about 10 g (including, for example, greater than about any of 20 g, 30 g, 40 g, 50 g, 60 g, 70 g, 80 g, 90 g, 100 g, 200 g, 300 g, 400 g, 500 g, or greater); and/or (c) has a volume greater than about 100 mL (including, for example, greater than about any of 200 mL, 300 mL, 400 mL, 500 mL, 600 mL, 700 mL, 800 mL, 900 mL, 1 L, 2 L, 3 L, 4 L, 5 L, or greater).

Thus, in some embodiments, provided herein is a system capable of producing a composition comprising an engineered OMV according to any of the embodiments described herein. In some embodiments, the system comprises a first reactor (e.g., a photobioreactor) for the production of the engineered OMV. In some embodiments, the first reactor is a photobioreactor configured to receive light and photosynthetic microorganisms (e.g., cyanobacteria or eukaryotic microalgae) capable of producing the engineered OMV, wherein culturing the photosynthetic microorganisms under suitable conditions (e.g., appropriate light exposure, culture medium, and incubation conditions, such as temperature and agitation) allows for the production of the engineered OMV in the photobioreactor. In some embodiments, the photobioreactor is configured to receive ambient air/CO2. In some embodiments, the system further comprises a receptacle configured to receive engineered OMVs produced in the photobioreactor. In some embodiments, the receptacle is connected to the photobioreactor by way of a filtration interface (e.g., an ultrafiltration interface), wherein engineered OMVs produced in the photobioreactor are capable of passing through the filtration interface into the receptacle. In some embodiments, photosynthetic microorganisms in the photobioreactor are incapable or substantially incapable of passing through the filtration interface into the receptacle. In some embodiments, the filtration interface comprises one or more filtration membranes (e.g., ultrafiltration membranes). In some embodiments, the filtration interface comprises one or more (including, for example, 2, 3, 4, 5, 6, 7, 8, 9, 10, or more) ultrafiltration membranes.

In some embodiments, provided herein is a system for the production of an engineered OMV according to any of the embodiments described herein, the system comprising: (a) a first reactor configured to receive a microorganism capable of producing the engineered OMV; (b) a receptacle configured to receive the engineered OMV produced in the first reactor; and (c) a filtration interface connecting the first reactor to the receptable, wherein the engineered OMV produced in the first reactor is capable of passing through the filtration interface into the receptacle. In some embodiments, the first reactor is a photobioreactor configured to receive light, and the microorganism is a photosynthetic microorganism. In some embodiments, the photosynthetic microorganism is a cyanobacterium or a eukaryotic microalga. In some embodiments, the photosynthetic microorganism is an engineered host cell according to any of the embodiments described herein. In some embodiments, the receptable is a second reactor. In some embodiments, the second reactor is in conditions suitable for carrying out the conversion of $CO_2$ and $H_2O$ to $HCO_3^-$ and $H^+$.

In some embodiments, according to any of the systems for the production of an engineered OMV described herein, the first reactor is configured to receive ambient air/CO2.

In some embodiments, according to any of the systems for the production of an engineered OMV described herein, the microorganism in the first reactor is incapable or substantially incapable of passing through the filtration interface into the receptacle.

In some embodiments, according to any of the systems for the production of an engineered OMV described herein, the filtration interface comprises one or more filtration membranes. In some embodiments, the filtration interface comprises at least 2, 3, 4, or 5 filtration membranes. In some embodiments, the one or more filtration membranes are one or more ultrafiltration membranes. In some embodiments, the filtration interface comprises at least 2, 3, 4, or 5 ultrafiltration membranes.

In some embodiments, according to any of the systems for the production of an engineered OMV described herein, the receptacle is configured to receive the engineered OMV: (a) at a concentration greater than about 100 mg/L (including, for example, greater than about any of 200 mg/L, 300 mg/L, 400 mg/L, 500 mg/L, 600 mg/L, 700 mg/L, 800 mg/L, 900 mg/L, 1 g/L, 2 g/L, 3 g/L, 4 g/L, 5 g/L, 6 g/L, 7 g/L, 8 g/L, 9 g/L, 10 g/L, or greater); (b) in an amount greater than about 10 g (including, for example, greater than about any of 20 g, 30 g, 40 g, 50 g, 60 g, 70 g, 80 g, 90 g, 100 g, 200 g, 300 g, 400 g, 500 g, or greater); and/or (c) in a volume greater than about 100 mL (including, for example, greater than about any of 200 mL, 300 mL, 400 mL, 500 mL, 600 mL, 700 mL, 800 mL, 900 mL, 1 L, 2 L, 3 L, 4 L, 5 L, or greater).

K. Methods of Using the Engineered OMVs

As would be appreciated from the present disclosure, the engineered OMVs according to the present disclosure can be used for a variety of purposes.

Accordingly, in one aspect, provided herein is a method of reducing $CO_2$ comprising interacting an engineered OMV according to any of the embodiments described herein employing a fusion protein comprising a polypeptide having a carbonic anhydrase activity with $CO_2$ under a condition suitable for the polypeptide having a carbonic anhydrase activity to convert $CO_2$ to a catalysis product. In some embodiments, the catalysis product is a metal carbonate. In some embodiments, the engineered OMV is interacted with $CO_2$ in the presence of $H_2O$ and a metal ion under alkaline conditions suitable for (i) the conversion of $CO_2$ to $CO_3^{2-}$ by the polypeptide having a carbonic anhydrase activity, and (ii) association of $CO_3^{2-}$ with the metal ion to form the metal carbonate. In some embodiments, the metal ion is a divalent metal cation. In some embodiments, the metal ion is $Ca^{2+}$, $Mg^{2+}$, $Fe^{2+}$, $Zn^{2+}$, $Cu^{2+}$, or $Mn^{2+}$. Accordingly, in some embodiments, the catalysis product is $CaCO_3$, $MgCO_3$, $FeCO_3$, $ZnCO_3$, $CuCO_3$, or $MnCO_3$. In some embodiments, the metal ion is a monovalent metal cation. In some embodiments, the metal ion is $Li^+$. Accordingly, in some embodiments, the catalysis product is $Li_2CO_3$.

Figure 2:
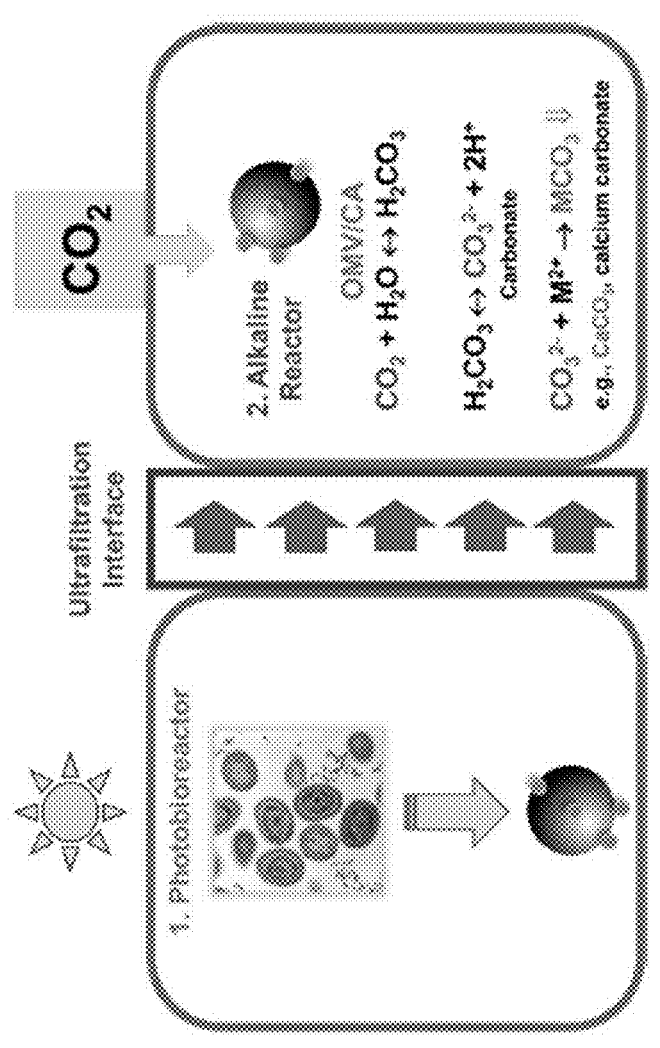

In some embodiments, the engineered OMV catalyzes the reversable reaction $CO_2+H_2O=H_2CO_3$ (carbonic acid; subsequently forming $HCO_3$ [bicarbonate]+$H^+$). In some embodiment, the reaction is performed under mildly alkaline condition (e.g., pH 10) and in the presence of a suitable salt (e.g., $CaCl_2$). In some embodiments, the bicarbonate precipitates spontaneously as an insoluble carbonate (e.g., calcium carbonate, $CaCO_3$). In some embodiments, the engineered OMV is used to capture dissolved $CO_2$ as stable carbonate solids. The process can be used for carbon capture, storage, and utilization. (FIG. 2).

In some embodiments, according to any of the methods of reducing CO2 described herein, the engineered OMV is interacted with CO2 in air, water, or waste.

In some embodiments, according to any of the methods of reducing CO2 described herein, the method further comprises producing the engineered OMV according to any of the method described herein. In some embodiments, producing the engineered OMV is carried out in a first reactor and producing the catalysis product is carried out in a second reactor. In some embodiments, the method further comprises isolating engineered OMVs produced in the first reactor and introducing the isolated engineered OMVs into the second reactor. In some embodiments, isolating the engineered OMVs is carried out by filtration.

Figure 3:
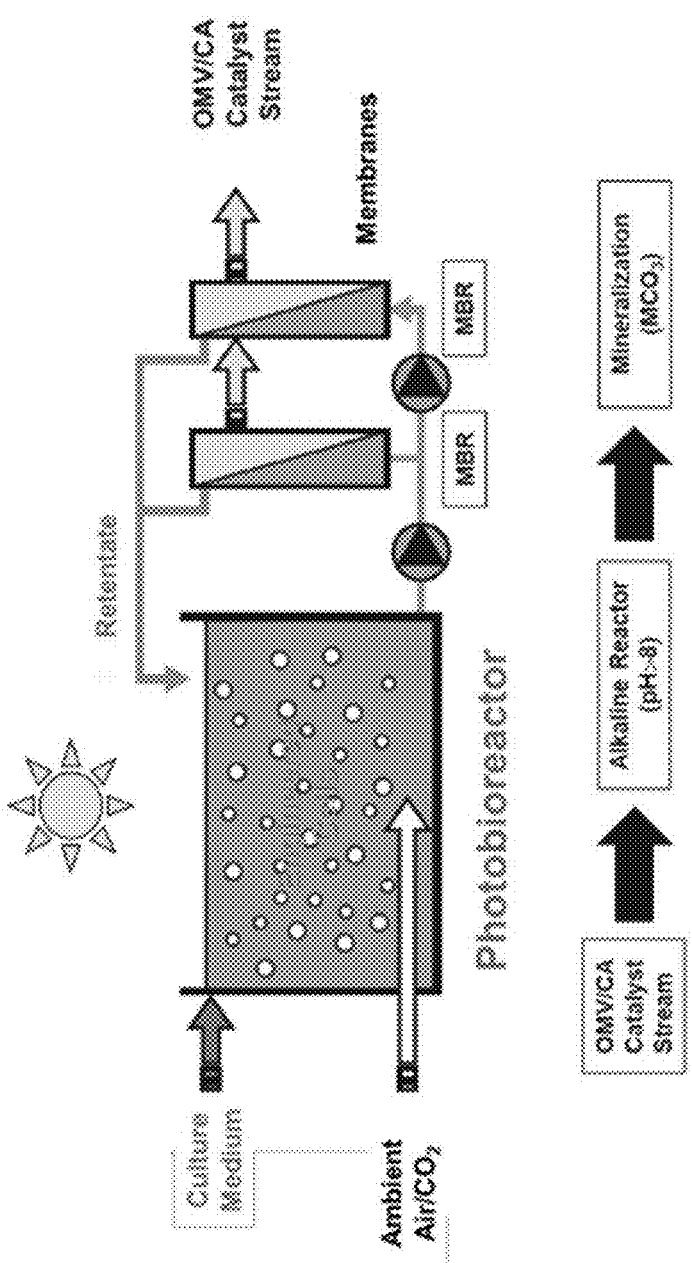
FIG. 3 illustrates a method for scaling up the OMV-CA (carbonic anhydrase) nanocatalyst platform for industrial application.

In some embodiments, the method of separating the engineered OMVs are scaled up for industrial application. In some embodiments, the system illustrated in FIG. 3 is used.

L. Reactor Systems

In one aspect of the present disclosure, provided herein is a system capable of producing an engineered OMV according to any of the embodiments described herein and carrying out a reaction using the engineered OMV. In some embodiments, the engineered OMV presents on its surface a polypeptide having a carbonic anhydrase activity, and the engineered OMV is used to catalyze the conversion of $CO_2$ and $H_2O$ to $HCO_3^-$ and $H^+$. In some embodiments, the system is capable of producing a composition comprising a plurality of the engineered OMVs. In some embodiments, the composition (a) comprises the engineered OMV at a concentration greater than about 100 mg/L (including, for example, greater than about any of 200 mg/L, 300 mg/L, 400 mg/L, 500 mg/L, 600 mg/L, 700 mg/L, 800 mg/L, 900 mg/L, 1 g/L, 2 g/L, 3 g/L, 4 g/L, 5 g/L, 6 g/L, 7 g/L, 8 g/L, 9 g/L, 10 g/L, or greater); (b) comprises the engineered OMV in an amount greater than about 10 g (including, for example, greater than about any of 20 g, 30 g, 40 g, 50 g, 60 g, 70 g, 80 g, 90 g, 100 g, 200 g, 300 g, 400 g, 500 g, or greater); and/or (c) has a volume greater than about 100 mL (including, for example, greater than about any of 200 mL, 300 mL, 400 mL, 500 mL, 600 mL, 700 mL, 800 mL, 900 mL, 1 L, 2 L, 3 L, 4 L, 5 L, or greater).

Thus, in some embodiments, provided herein is a system capable of catalyzing the conversion of $CO_2$ and $H_2O$ to $HCO_3^-$ and $H^+$ using an engineered OMV according to any of the embodiments described herein presenting on its surface a polypeptide having a carbonic anhydrase activity. In some embodiments, the system comprises a first reactor (e.g., a photobioreactor) for the production of the engineered OMV. In some embodiments, the first reactor is a photobioreactor configured to receive light and photosynthetic microorganisms (e.g., cyanobacteria or eukaryotic microalgae) capable of producing the engineered OMV, wherein culturing the photosynthetic microorganisms under suitable conditions (e.g., appropriate light exposure, culture medium, and incubation conditions, such as temperature and agitation) allows for the production of the engineered OMV in the photobioreactor. In some embodiments, the photobioreactor is configured to receive ambient air/$CO_2$. In some embodiments, the system further comprises a second reactor configured to receive engineered OMVs produced in the photobioreactor into an aqueous composition and carry out the conversion of $CO_2$ and $H_2O$ to $HCO_3^-$ and $H^+$. In some embodiments, the second reactor is an alkaline reactor, e.g., a reactor comprising an aqueous composition having a pH greater than about 8.0 (including, for example, greater than about any of 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or greater). In some embodiments, the second reactor is configured to receive $CO_2$. In some embodiments, the aqueous composition in the second reactor further comprises a metal ion. In some embodiments, the metal ion is a divalent metal cation. In some embodiments, the metal ion is $Ca^{2+}$, $Mg^{2+}$, $Fe^{2+}$, $Zn^{2+}$, $Cu^{2+}$, or $Mn^{2+}$. In some embodiments, the metal ion is a monovalent metal cation. In some embodiments, the metal ion is $Li^+$. Accordingly, in some embodiments, a metal carbonate (e.g., $CaCO_3$, $MgCO_3$, $FeCO_3$, $ZnCO_3$, $CuCO_3$, $MnCO_3$, or $Li_2CO_3$) is formed in the second reactor. In some embodiments, the second reactor is connected to the photobioreactor by way of a filtration interface (e.g., an ultra-filtration interface), wherein engineered OMVs produced in the photobioreactor are capable of passing through the filtration interface into the second reactor. In some embodiments, photosynthetic microorganisms in the photobioreactor are incapable or substantially incapable of passing through the filtration interface into the second reactor. In some embodiments, the filtration interface comprises one or more filtration membranes (e.g., ultrafiltration membranes). In some embodiments, the filtration interface comprises one or more (including, for example, 2, 3, 4, 5, 6, 7, 8, 9, 10, or more) ultrafiltration membranes.

In some embodiments, provided herein is a system for catalyzing the conversion of $CO_2$ and $H_2O$ to $HCO_3^-$ and $H^+$, the system comprising: (a) a first reactor configured to receive a microorganism capable of producing an engineered OMV according to any of the embodiments described herein presenting a heterologous enzyme comprising a carbonic anhydrase (CA) polypeptide or functional fragment thereof; (b) a second reactor configured to receive the engineered OMV produced in the first reactor in conditions suitable for carrying out the conversion of $CO_2$ and $H_2O$ to $HCO_3^-$ and $H^+$; and (c) a filtration interface connecting the first reactor to the second reactor, wherein the engineered OMV produced in the first reactor is capable of passing through the filtration interface into the second reactor. In some embodiments, the first reactor is a photobioreactor configured to receive light, and the microorganism is a photosynthetic microorganism. In some embodiments, the photosynthetic microorganism is a cyanobacterium or a eukaryotic microalga. In some embodiments, the photosynthetic microorganism is an engineered host cell according to any of the embodiments described herein.

In some embodiments, according to any of the systems for catalyzing the conversion of $CO_2$ and $H_2O$ to $HCO_3^-$ and $H^+$ described herein, the first reactor is configured to receive ambient air/$CO_2$.

In some embodiments, according to any of the systems for catalyzing the conversion of $CO_2$ and $H_2O$ to $HCO_3^-$ and $H^+$ described herein, the second reactor is an alkaline reactor comprising an aqueous composition having a pH greater than about 8.0 (including, for example, greater than about any of 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or greater).

In some embodiments, according to any of the systems for catalyzing the conversion of $CO_2$ and $H_2O$ to $HCO_3^-$ and $H^+$ described herein, the second reactor is configured to receive $CO_2$.

In some embodiments, according to any of the systems for catalyzing the conversion of $CO_2$ and $H_2O$ to $HCO_3^-$ and $H^+$ described herein, the second reactor comprises an aqueous composition comprising a metal ion under conditions suitable for the formation of a metal carbonate comprising the metal ion. In some embodiments, the metal ion is a divalent metal cation. In some embodiments, the metal ion is a monovalent metal cation. In some embodiments, the metal ion is $Ca^{2+}$, $Mg^{2+}$, $Fe^{2+}$, $Zn^{2+}$, $Cu^{2+}$, $Mn^{2+}$, or $Li^+$. Accordingly, in some embodiments, the metal carbonate is $CaCO_3$, $MgCO_3$, $FeCO_3$, $ZnCO_3$, $CuCO_3$, $MnCO_3$, or $Li_2CO_3$.

In some embodiments, according to any of the systems for catalyzing the conversion of $CO_2$ and $H_2O$ to $HCO_3^-$ and $H^+$ described herein, the microorganism in the first reactor is incapable or substantially incapable of passing through the filtration interface into the second reactor.

In some embodiments, according to any of the systems for catalyzing the conversion of $CO_2$ and $H_2O$ to $HCO_3^-$ and $H^+$ described herein, the filtration interface comprises one or more filtration membranes. In some embodiments, the filtration interface comprises at least 2, 3, 4, or 5 filtration membranes. In some embodiments, the one or more filtration membranes are one or more ultrafiltration membranes. In some embodiments, the filtration interface comprises at least 2, 3, 4, or 5 ultrafiltration membranes.

In some embodiments, according to any of the systems for catalyzing the conversion of $CO_2$ and $H_2O$ to $HCO_3^-$ and $H^+$ described herein, the second reactor is configured to receive the engineered OMV: (a) at a concentration greater than about 100 mg/L (including, for example, greater than about any of 200 mg/L, 300 mg/L, 400 mg/L, 500 mg/L, 600 mg/L, 700 mg/L, 800 mg/L, 900 mg/L, 1 g/L, 2 g/L, 3 g/L, 4 g/L, 5 g/L, 6 g/L, 7 g/L, 8 g/L, 9 g/L, 10 g/L, or greater); (b) in an amount greater than about 10 g (including, for example, greater than about any of 20 g, 30 g, 40 g, 50 g, 60 g, 70 g, 80 g, 90 g, 100 g, 200 g, 300 g, 400 g, 500 g, or greater); and/or (c) in a volume greater than about 100 mL (including, for example, greater than about any of 200 mL, 300 mL, 400 mL, 500 mL, 600 mL, 700 mL, 800 mL, 900 mL, 1 L, 2 L, 3 L, 4 L, 5 L, or greater).

M. Kits

Also provided herein are kits comprising a nucleic acid encoding a fusion protein as provided herein, or a composition thereof, packaged into suitable packaging material. A kit optionally includes a label or packaging insert including a description of the components or instructions for use of the components therein.

The term "packaging material" refers to a physical structure housing the components of the kit. The packaging material can maintain the components sterilely, and can be made of material commonly used for such purposes (e.g., paper, corrugated fiber, glass, plastic, foil, ampoules, vials, tubes, etc.).

Kits provided herein can include labels or inserts. Labels or inserts include "printed matter," e.g., paper or cardboard, separate or affixed to a component, a kit or packing material (e.g., a box), or attached to, for example, an ampoule, tube, or vial containing a kit component. Labels or inserts can additionally include a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media, or memory type cards. Labels or inserts can include information identifying manufacturer information, lot numbers, manufacturer location, and date.

Kits provided herein can additionally include other components. Each component of the kit can be enclosed within an individual container, and all of the various containers can be within a single package. Kits can also be designed for cold storage. A kit can further be designed to contain nucleic acids provided herein, or cells that contain the nucleic acids. The cells in the kit can be maintained under appropriate storage conditions until ready to use.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

All applications, publications, patents and other references, GenBank citations and ATCC citations cited herein are incorporated by reference in their entirety. In case of conflict, the specification, including definitions, will control.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250 includes 1, 2, 3, 4, 5, 6, 7, 8, 9, 10, 11, 12, 13, 14, 15, 16, 17, 18, 19, 20, etc. In a further example, reference to a range of 25-250, 250-500, 500-1,000, 1,000-2,500, 2,500-5,000, 5,000-25,000, 25,000-50,000 includes any numerical value or range within or encompassing such values, e.g., 25, 26, 27, 28, 29 . . . 250, 251, 252, 253, 254 . . . 500, 501, 502, 503, 504 . . . , etc.

As also used herein a series of ranges are disclosed throughout this document. The use of a series of ranges includes combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth.

For the sake of conciseness, certain abbreviations are used herein. One example is the single letter abbreviation to represent amino acid residues. The amino acids and their corresponding three letter and single letter abbreviations are as follows:

| alanine | Ala | (A) |
|---|---|---|
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |

-continued

| tryptophan | Trp | (W) |
| tyrosine | Tyr | (Y) |
| valine | Val | (V) |

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

7. NON-LIMITING ASPECTS AND EMBODIMENTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure numbered 1-110 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. An engineered outer membrane vesicle (OMV) comprising a heterologous enzyme presented on the outer surface of the engineered OMV.

Aspect 2. The engineered OMV of aspect 1, wherein the engineered OMV is obtained from a photosynthetic microorganism.

Aspect 3. The engineered OMV of aspect 2, wherein the photosynthetic microorganism is an engineered photosynthetic microorganism.

Aspect 4. The engineered OMV of any one of aspects 2-3, wherein the photosynthetic microorganism is a gram-negative bacterium.

Aspect 5. The engineered OMV of aspect 4, wherein the gram-negative bacterium is a cyanobacterium.

Aspect 6. The engineered OMV of aspect 5, wherein the cyanobacterium is selected from *Synechocystis* sp., *Synechococcus* sp., *Microcystis aeruginosa, Leptolyngbya boryana, Cyanobium gracile, Phormidium persicinum*, and *Gloeocapsa* sp.

Aspect 7. The engineered OMV of aspect 5, wherein the cyanobacterium is selected from *Synechococcus* sp. PCC 7942, *Synechococcus elongatus* UTEX 2973, and *Synechocystis* sp. PCC 6803.

Aspect 8. The engineered OMV of any one of aspects 2-3, wherein the photosynthetic microorganism is a eukaryotic microalgae.

Aspect 9. The engineered OMV of any one of aspects 1-8, wherein the heterologous enzyme is operably linked to a transmembrane protein embedded in the membrane of the engineered OMV to form a fusion protein.

Aspect 10. The engineered OMV of aspect 9, wherein the transmembrane protein is derived from an autotransporter protein (ATP) or an outer membrane protein (OMP).

Aspect 11. The engineered OMV of aspect 10, wherein the transmembrane protein is derived from an ATP selected from antigen 43 (Ag43), hemoglobin-binding protease (Hbp), pertactin, extracellular serine protease plasmid-encoded (EspP), IgA1 protease, esterase autotransporter (EstA), adhesion and penetration protein (Hap), adhesin involved in diffuse adherence (AIDA-I), plasmid-encoded toxin (Pet), protease involved in intestinal colonization (Pic), temperature-sensitive hemagglutinin (Tsh), *Shigella* extracellular protein (SepA), and vacuolating cytotoxin A (VacA).

Aspect 12. The engineered OMV of aspect 11, wherein the ATP is Ag43.

Aspect 13. The engineered OMV of aspect 12, wherein the transmembrane protein comprises the amino acid sequence of SEQ ID NO: 8.

Aspect 14. The engineered OMV of aspect 11, wherein the ATP is Hbp.

Aspect 15. The engineered OMV of aspect 14, wherein the transmembrane protein comprises the amino acid sequence of SEQ ID NO: 9.

Aspect 16. The engineered OMV of aspect 10, wherein the transmembrane protein is derived from an OMP selected from *Synechococcus* outer membrane protein A (SomA), MipA, and ice nucleation proteins (INPs).

Aspect 17. The engineered OMV of aspect 16, wherein the OMP is SomA.

Aspect 18. The engineered OMV of aspect 17, wherein the transmembrane protein comprises the amino acid sequence of SEQ ID NO: 10.

Aspect 19. The engineered OMV of aspect 16, wherein the OMP is MipA.

Aspect 20. The engineered OMV of aspect 19, wherein the transmembrane protein comprises the amino acid sequence of SEQ ID NO: 11.

Aspect 21. The engineered OMV of aspect 16, wherein the OMP is an INP.

Aspect 22. The engineered OMV of aspect 21, wherein the INP is from *Pseudomonas syringae.*

Aspect 23. The engineered OMV of aspect 22, wherein the transmembrane protein comprises the amino acid sequence of SEQ ID NO: 12.

Aspect 24. The engineered OMV of any one of aspects 9-23, wherein the fusion protein further comprises a linker connecting the heterologous enzyme to the transmembrane protein.

Aspect 25. The engineered OMV of aspect 17, wherein the linker is a peptide linker comprising the amino acid sequence of any one of SEQ ID NOs: 17-19 and 25.

Aspect 26. The engineered OMV of any one of aspects 1-25, wherein the engineered OMV comprises at least about 10 heterologous enzyme molecules presented on its outer surface.

Aspect 27. The engineered OMV of any one of aspects 1-26, wherein the engineered OMV has a diameter of about 50 nm to about 250 nm.

Aspect 28. The engineered OMV of aspect 27, wherein the engineered OMV has a diameter of about 70 nm to about 130 nm.

Aspect 29. The engineered OMV of any one of aspects 1-28, wherein the heterologous enzyme comprises a carbonic anhydrase (CA) polypeptide or functional fragment thereof.

Aspect 30. The engineered OMV of aspect 29, wherein the CA polypeptide is derived from a thermostable CA.

Aspect 31. The engineered OMV of aspect 30, wherein the thermostable CA is from *Thermosulfurimonas dismutans*.

Aspect 32. The engineered OMV of aspect 31, wherein the CA polypeptide comprises the amino acid sequence of SEQ ID NO: 7.

Aspect 33. An engineered host cell capable of producing an OMV comprising a heterologous enzyme presented on the outer surface of the OMV, wherein the engineered host cell is a photosynthetic microorganism comprising heterologous nucleic acid encoding a fusion protein comprising the heterologous enzyme operably linked to a transmembrane protein, and wherein the fusion protein is capable of being inserted into the outer membrane of the engineered host cell such that the heterologous enzyme is presented on the outer surface of the engineered host cell.

Aspect 34. The engineered host cell of aspect 33, wherein the transmembrane protein is derived from an autotransporter protein (ATP) or an outer membrane protein (OMP).

Aspect 35. The engineered host cell of aspect 34, wherein the transmembrane protein is derived from an ATP selected from antigen 43 (Ag43), hemoglobin-binding protease (Hbp), pertactin, extracellular serine protease plasmid-encoded (EspP), IgA1 protease, esterase autotransporter (EstA), adhesion and penetration protein (Hap), adhesin involved in diffuse adherence (AIDA-I), plasmid-encoded toxin (Pet), protease involved in intestinal colonization (Pic), temperature-sensitive hemagglutinin (Tsh), *Shigella* extracellular protein (SepA), and vacuolating cytotoxin A (VacA).

Aspect 36. The engineered host cell of aspect 35, wherein the ATP is Ag43.

Aspect 37. The engineered host cell of aspect 36, wherein the transmembrane protein comprises the amino acid sequence of SEQ ID NO: 8.

Aspect 38. The engineered host cell of aspect 35, wherein the ATP is Hbp.

Aspect 39. The engineered host cell of aspect 38, wherein the transmembrane protein comprises the amino acid sequence of SEQ ID NO: 9.

Aspect 40. The engineered host cell of aspect 34, wherein the transmembrane protein is derived from an OMP selected from *Synechococcus* outer membrane protein A (SomA), MipA, and ice nucleation proteins (INPs).

Aspect 41. The engineered host cell of aspect 40, wherein the OMP is SomA.

Aspect 42. The engineered host cell of aspect 41, wherein the transmembrane protein comprises the amino acid sequence of SEQ ID NO: 10.

Aspect 43. The engineered host cell of aspect 40, wherein the OMP is MipA.

Aspect 44. The engineered host cell of aspect 43, wherein the transmembrane protein comprises the amino acid sequence of SEQ ID NO: 11.

Aspect 45. The engineered host cell of aspect 40, wherein the OMP is an INP.

Aspect 46. The engineered host cell of aspect 45, wherein the INP is from *Pseudomonas syringae*.

Aspect 47. The engineered host cell of aspect 46, wherein the transmembrane protein comprises the amino acid sequence of SEQ ID NO: 12.

Aspect 48. The engineered host cell of any one of aspects 33-47, wherein the fusion protein further comprises a linker connecting the heterologous enzyme to the transmembrane protein.

Aspect 49. The engineered host cell of aspect 48, wherein the linker is a peptide linker comprising the amino acid sequence of any one of SEQ ID NOs: 17-19 and 25.

Aspect 50. The engineered host cell of any one of aspects 33-49, wherein the fusion protein further comprises a signal peptide capable of targeting the fusion protein to the inner membrane of the engineered host cell.

Aspect 51. The engineered host cell of aspect 50, wherein the signal peptide comprises the amino acid sequence of any one of SEQ ID NOs: 13-16.

Aspect 52. The engineered host cell of any one of aspects 33-51, wherein the engineered host cell is a cyanobacterium.

Aspect 53. The engineered host cell of aspect 52, wherein the cyanobacterium is selected from *Synechocystis* sp., *Synechococcus* sp., *Microcystis aeruginosa, Leptolyngbya boryana, Cyanobium gracile, Phormidium persicinum*, and *Gloeocapsa* sp.

Aspect 54. The engineered host cell of aspect 53, wherein the cyanobacterium is selected from *Synechococcus* sp. PCC 7942, *Synechococcus elongatus* UTEX 2973, and *Synechocystis* sp. PCC 6803.

Aspect 55. The engineered host cell of any one of aspects 33-51, wherein the engineered host cell is a eukaryotic microalgae.

Aspect 56. The engineered host cell of any one of aspects 33-55, wherein the heterologous enzyme comprises a CA polypeptide or functional fragment thereof.

Aspect 57. The engineered host cell of aspect 56, wherein the CA polypeptide is derived from a thermostable CA.

Aspect 58. The engineered host cell of aspect 57, wherein the thermostable CA is from *Thermosulfurimonas dismutans*.

Aspect 59. The engineered host cell of aspect 58, wherein the CA polypeptide comprises the amino acid sequence of SEQ ID NO: 7.

Aspect 60. The engineered host cell of any one of aspects 33-59, wherein the heterologous nucleic acid is present extrachromosomally.

Aspect 61. The engineered host cell of aspect 60, wherein the heterologous nucleic acid is a plasmid.

Aspect 62. The engineered host cell of any one of aspects 33-59, wherein the heterologous nucleic acid is integrated into the chromosome of the engineered host cell.

Aspect 63. The engineered host cell of aspect 62, wherein the heterologous nucleic acid is integrated into the chromosome by site-specific targeting.

Aspect 64. The engineered host cell of aspect 63, wherein the heterologous nucleic acid is integrated into the chromosome by site-specific targeting using a CRISPR/Cas9 system.

Aspect 65. The engineered host cell of any one of aspects 33-64, wherein the heterologous nucleic acid is operably linked to an inducible promoter.

Aspect 66. A method of producing an engineered OMV comprising:
(a) culturing the engineered host cell according to any one of aspects 33-65 under conditions suitable for expression of the fusion protein; and
(b) obtaining an OMV produced by the engineered host cell, thereby producing the engineered OMV.

Aspect 67. The method of aspect 66, wherein the engineered host cell is cultured in the presence of CO2 and light.

Aspect 68. The method of aspect 66 or 67, further comprising filtering the engineered OMV.

Aspect 69. The method of aspect 68, wherein the filtering is performed by ultrafiltration.

Aspect 70. The method of aspect 68, wherein the filtering is performed by a membrane bioreactor.

Aspect 71. The method of any one of aspects 66-70, further comprising concentrating the engineered OMV.

Aspect 72. A nanocatalyst composition comprising the engineered OMV of any one of aspects 1-31.

Aspect 73. The nanocatalyst composition of aspect 72, wherein the engineered OMV is produced by the method of any one of aspects 66-71.

Aspect 74. The nanocatalyst composition of aspect 72 or 73, comprising the engineered OMV at a concentration greater than about 100 mg/L.

Aspect 75. The nanocatalyst composition of any one of aspects 72-74, comprising the engineered OMV in an amount greater than about 10 g.

Aspect 76. The nanocatalyst composition of aspect 74 or 75, wherein the composition is not a therapeutic composition.

Aspect 77. A nanocatalyst product comprising the nanocatalyst composition of any one of aspects 74-76 in a volume greater than about 1 L.

Aspect 78. A method of reducing $CO_2$ comprising interacting the engineered OMV according to any one of aspects 29-32 with $CO_2$ under a condition suitable for the CA polypeptide or functional fragment thereof to convert $CO_2$ to a catalysis product.

Aspect 79. The method of aspect 78, wherein the catalysis product is a metal carbonate.

Aspect 80. The method of aspect 79, wherein the engineered OMV is interacted with $CO_2$ in the presence of H2O and a metal ion under alkaline conditions suitable for (i) the conversion of $CO_2$ to $CO_3^2$ by the CA polypeptide or functional fragment thereof, and (ii) association of $CO_3^{2-}$ with the metal ion to form the metal carbonate.

Aspect 81. The method of aspect 80, wherein the metal ion is Ca2+, Mg2+, Fe2+, Zn2+, Cu2+, Mn2+, or Li+.

Aspect 82. The method of any one of aspects 78-81, wherein the engineered OMV is interacted with CO2 in air, water, or waste.

Aspect 83. The method of any one of aspects 78-82, further comprising producing the engineered OMV according to the method of any one of aspects 66-71.

Aspect 84. The method of aspect 83, wherein producing the engineered OMV is carried out in a first reactor and producing the catalysis product is carried out in a second reactor.

Aspect 85. The method of aspect 84, further comprising isolating engineered OMVs produced in the first reactor and introducing the isolated engineered OMVs into the second reactor.

Aspect 86. The method of aspect 85, wherein isolating the engineered OMVs is carried out by filtration.

Aspect 87. A system for the production of an engineered OMV according to any one of aspects 1-32, the system comprising: (a) a first reactor configured to receive a microorganism capable of producing the engineered OMV; (b) a receptacle configured to receive the engineered OMV produced in the first reactor; and (c) a filtration interface connecting the first reactor to the receptacle, wherein the engineered OMV produced in the first reactor is capable of passing through the filtration interface into the receptacle.

Aspect 88. The system of aspect 87, wherein the first reactor is a photobioreactor configured to receive light, and wherein the microorganism is a photosynthetic microorganism.

Aspect 89. The system of aspect 88, wherein the photosynthetic microorganism is a cyanobacterium or a eukaryotic microalga.

Aspect 90. The system of aspect 89, wherein the photosynthetic microorganism is an engineered host cell according to any one of aspects 33-65.

Aspect 91. The system of any one of aspects 87-90, wherein the first reactor is configured to receive ambient air/CO2.

Aspect 92. The system of any one of aspects 87-91, wherein the microorganism in the first reactor is incapable or substantially incapable of passing through the filtration interface into the receptacle.

Aspect 93. The system of any one of aspects 87-92, wherein the filtration interface comprises one or more filtration membranes.

Aspect 94. The system of aspect 93, wherein the filtration interface comprises at least 2, 3, 4, or 5 filtration membranes.

Aspect 95. The system of aspect 93 or 94, wherein the one or more filtration membranes are one or more ultrafiltration membranes.

Aspect 96. The system of any one of aspects 87-95, wherein the receptacle is configured to receive the engineered OMV: (a) at a concentration greater than about 100 mg/L; (b) in an amount greater than about 10 g; and/or (c) in a volume greater than about 100 mL.

Aspect 97. A system for catalyzing the conversion of $CO_2$ and $H_2O$ to $HCO_{3-}$ and H+, the system comprising: (a) a first reactor configured to receive a microorganism capable of producing an engineered OMV according to any one of aspects 1-32; (b) a second reactor configured to receive the engineered OMV produced in the first reactor in conditions suitable for carrying out the conversion of $CO_2$ and $H_2O$ to $HCO_{3-}$ and $H_+$; and (c) a filtration interface connecting the first reactor to the second reactor, wherein the engineered OMV produced in the first reactor is capable of passing through the filtration interface into the second reactor.

Aspect 98. The system of aspect 97, wherein the first reactor is a photobioreactor configured to receive light, and wherein the microorganism is a photosynthetic microorganism.

Aspect 99. The system of aspect 98, wherein the photosynthetic microorganism is a cyanobacterium or a eukaryotic microalga.

Aspect 100. The system of aspect 99, wherein the photosynthetic microorganism is an engineered host cell according to any one of aspects 33-65.

Aspect 101. The system of any one of aspects 97-100, wherein the first reactor is configured to receive ambient air/$CO_2$.

Aspect 102. The system of any one of aspects 97-101, wherein the second reactor is an alkaline reactor comprising an aqueous composition having a pH greater than about 8.0.

Aspect 103. The system of any one of aspects 97-105, wherein the second reactor is configured to receive $CO_2$.

Aspect 104. The system of any one of aspects 97-106, wherein the second reactor comprises an aqueous composition comprising a metal ion under conditions suitable for the formation of a metal carbonate comprising the metal ion.

Aspect 105. The system of aspect 107, wherein the metal ion is Ca2+, Mg2+, Fe2+, Zn2+, Cu2+, Mn2+, or Li+.

Aspect 106. The system of any one of aspects 97-108, wherein the microorganism in the first reactor is incapable or substantially incapable of passing through the filtration interface into the second reactor.

Aspect 107. The system of any one of aspects 97-106, wherein the filtration interface comprises one or more filtration membranes.

Aspect 108. The system of aspect 107, wherein the filtration interface comprises at least 2, 3, 4, or 5 filtration membranes.

Aspect 109. The system of aspect 107 or 108, wherein the one or more filtration membranes are one or more ultrafiltration membranes.

Aspect 110. The system of any one of aspects 97-109, wherein the second reactor is configured to receive the engineered OMV: (a) at a concentration greater than about 100 mg/L; (b) in an amount greater than about 10 g; and/or (c) in a volume greater than about 100 mL; (a) at a concentration greater than about 100 mg/L; (b) in an amount greater than about 10 g; and/or (c) in a volume greater than about 100 mL.

8. EXAMPLES

A. Example 1: OMV Engineering

Proof-of-concept experimental studies were performed. They involved expression of fusion proteins in a) *E. coli* strains (common commercial strains such as BL21 [DE3]) and b) cyanobacterial species (*Synechococcus* sp. PCC 7942 and UTEX 2973).

Plasmid expression vectors for expressing fusion proteins included pET22b(+), pET25b(+), pBb(RSF1010)1k-GFPuv (Plasmid #106395; Addgene), and pSyn6 (GeneArt *Synechococcus* Protein Expression Vector). Constructs were conventionally transfected/transformed into cells. Cells were cultured under established conditions. Transfected/transformed cells were isolated using standard techniques.

Figure 4:
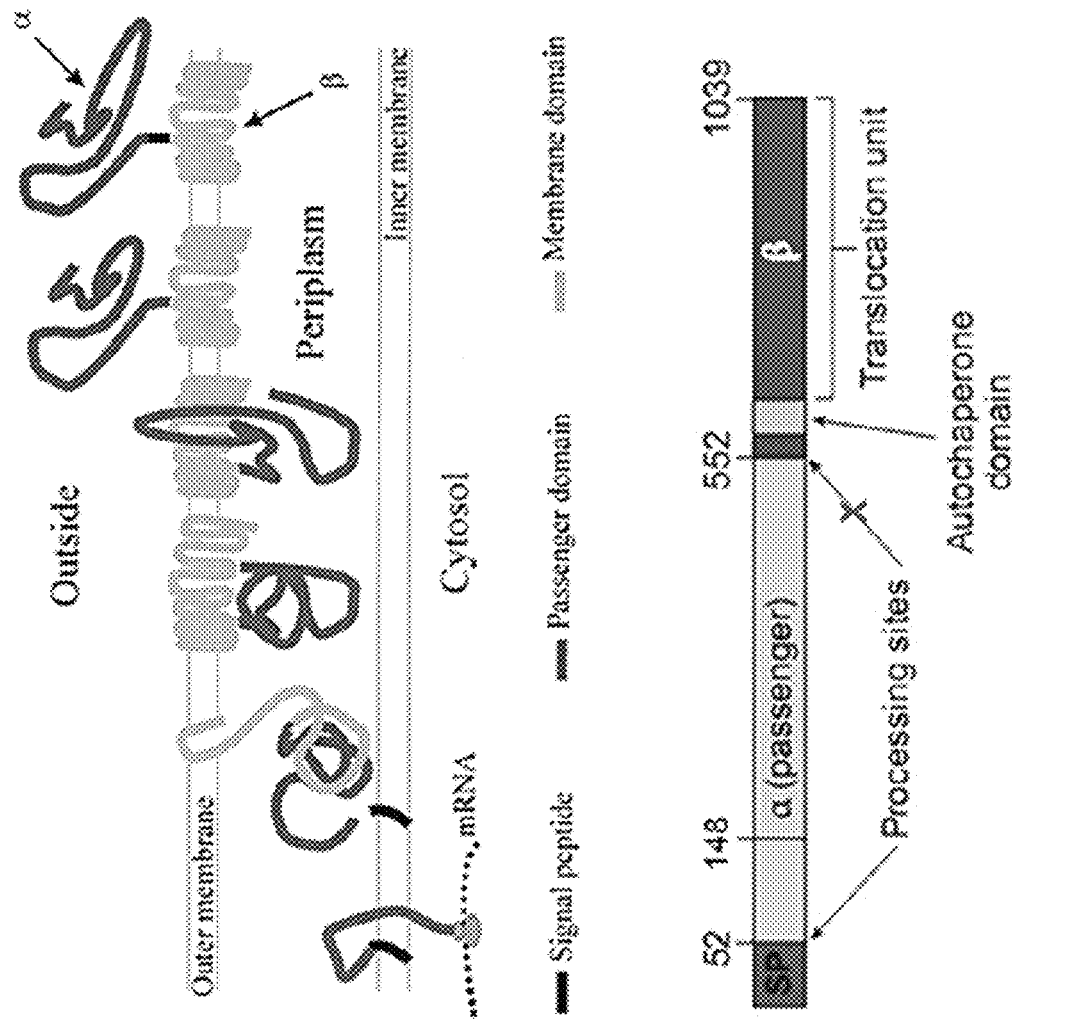
FIG. 4 illustrates the pathway by which an autotransporter such as Ag43 transports a protein domain to the surface of the OM of a gram-negative bacterial cell. Bottom: schematic diagram of a recombinant fusion protein design based on the Ag43 autotransporter, including a signal peptide (SP) for transport to the periplasm, an α domain (passenger), and a β domain (translocation unit).

Several fusion protein constructs were evaluated, each of which encodes a thermostable CA from *Thermosulfurimonas dismutans* (GenBank: OAQ21602.1; Td-CA). The Td-CA was fused, as appropriate, with a signal peptide and a transmembrane protein (e.g., a β-translocator domain from the *E. coli* autotransporter Ag43 as shown in FIG. 4). The constructs generated are summarized in Table 1.

TABLE 1

| Construct/Host cell | Fusion protein (FP) insert | Vector | SEQ ID NO (FP) |
|---|---|---|---|
| Ag43SP-TdCA-Ag43β-pET25b(+)/ *Escherichia coli* K-12 | TdCA-Ag43 fusion protein: Ag 43 *E. coli* signal peptide + Td carbonic anhydrase/CA + linker + Ag43 β-chain translocator domain | pET25b(+) | 1 |
| 6xHis-TdCA-Ag43-pET25b(+)/ *Escherichia coli* K-12 | TdCA-Ag43 fusion protein with 6X His | pET25b(+) | |
| SynSP-TdCA-Ag43β-pSyn6/ *Synechococcus elongatus* PCC 7942 or UTEX 2973 | TdCA-Ag43 fusion protein: *Synechococcus* PCC 7942 27-AA signal peptide + Td carbonic anhydrase/CA + linker + Ag43 β-chain translocator domain | pSyn6 | 2 |
| 6xHis-TdCA-Ag43-pBb(RSF1010)1k-GFPuv/ *Synechocystis* sp. (ATCC 27184) | TdCA-Ag43 fusion protein with 6X His | pBb(RSF1010)1k-GFPuv | |
| 6xHis-TdCA-Ag43-pSyn6/ *Synechococcus elongatus* PCC 7942 | TdCA-Ag43 fusion protein with 6X His | pSyn6 | |
| SP-TdCA-tHbp-pET25b(+)/ *Escherichia coli* K-12 | TdCA-Hbp fusion protein: signal peptide (Daleke-Schermerhorn et al.) + Td carbonic anhydrase/CA + linker + truncated Hbp passenger domain: minus the N-terminal D1 subdomain + the remaining subdomains + the β domain | pET25b(+) | 3 |
| tSomA-TdCA-pSyn6/ *Synechococcus elongatus* PCC 7942 or UTEX 2973 | SomA-TdCA fusion protein: Truncated *Synechococcus* SomA with the C-terminus at amino acid position 382 (located at the fifth cell-surface exposed loop) + Td carbonic anhydrase/CA | pSyn6 | 4 |
| tMipA-TdCA-pET25b(+)/ *Escherichia coli* K-12 | MipA-TdCA fusion protein: truncated MipA with the C-terminus at amino acid position 140 located at the third cell-surface exposed loop + linker + Td carbonic anhydrase/CA | pET25b(+) | 5 |

TABLE 1-continued

| Construct/Host cell | Fusion protein (FP) insert | Vector | SEQ ID NO (FP) |
| --- | --- | --- | --- |
| pelBSP-INPN-TdCA-pET22b(+)/ *Escherichia coli* K-12 | INPN-RE-TdCA fusion protein: pelB signal peptide + INPN domain from *Pseudomonas syringae* + linker + Td carbonic anhydrase/CA + His-Tag | pET22b(+) | 6 |

Fusion protein expression was evaluated by colony RT-PCR at the mRNA level and by immunoblotting at the protein level in both total cell lysates and lysates of OMVs. OMVs were obtained from cell culture supernatants by polyethylene glycol (PEG) precipitation and evidence of TdCA-Ag43 fusion protein expression in the OMVs was detected by immunoblotting.

Purified engineered OMV preparations were tested and found to have CA activity above background using standard techniques.

The study demonstrated successful expression of the fusion protein and enzyme activity in OMVs obtained from the engineered bacteria.

B. Example 2: Membrane Accumulation of TdCA-Ag43 Protein in UTEX 2973 Cells

Figure 1:
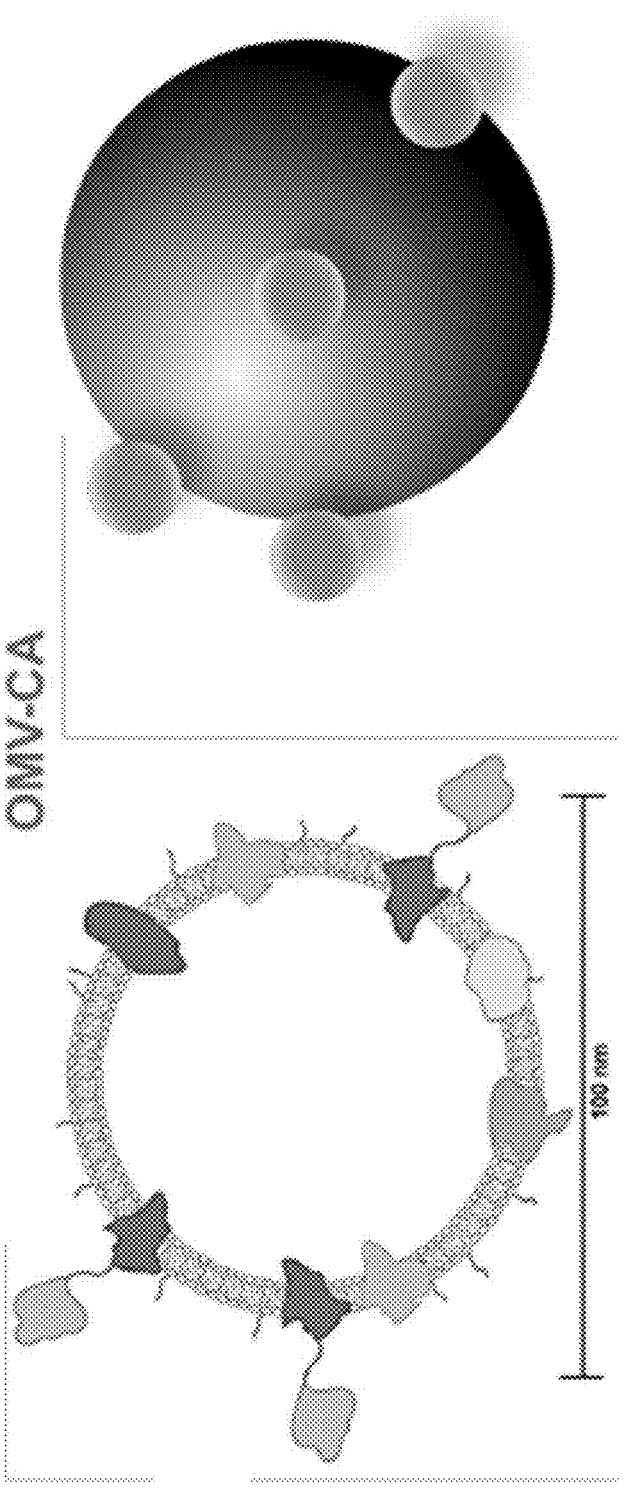

Carbonic anhydrase (CA) that can function at high temperatures (over 60° C.) from the bacterium *Thermosulfurimonas dismutans* (Td) was selected. TdCA was fused with a truncated *E. coli* autotransporter called antigen 43 (Ag43; FIG. 1; SEQ ID NO: 1). The coding sequence of the construct was inserted into a *Synechococcus*-specific plasmid vector with a strong, constitutive (continuous transcription) promoter at the NdeI restriction site (pSyn6; Thermo Fischer). The resulting recombinant plasmid (pSyn6-TdCA-Ag43; SEQ ID NO: 24) was transformed into the fast-growing cyanobacterium *Synechococcus elongatus* UTEX 2973 using tri-conjugal transformation, aided by one population of *E. coli* HB101 transformed with plasmid pRL623 and the pSyn6 plasmid and another population of *E. coli* HB101 transformed with plasmid pRL443. Following antibiotic selection by 10 µg/mL spectinomycin resistance on BG-11 (Millipore Sigma) agar plates, colonies were transferred to liquid BG-11 media (Millipore Sigma) supplemented with 10 µg/mL spectinomycin and incubated at 37° C. in 2.5% $CO_2$ under a light intensity of 60 µmol m$^{-2}$ s$^{-1}$ with shaking.

To detect expression of the fusion protein TdCA-Ag43 in transformed cyanobacteria, whole cells were lysed by vortexing with glass beads. To suppress proteolysis, complete protease inhibitor (MilliporeSigma) was added to the lysis mixture prior to lysis. Next, samples were mixed with 2× Laemmli buffer (BioRAD) and heated to 95° C. for 5 minutes. After centrifugation, samples were loaded on and electrophoresed through a 4-20% gradient SDS-PAGE gel (BioRAD). Protein was then transferred to a PVDF membrane (ImmobilonP; MilliporeSigma). The membrane was blocked with 5% bovine serum albumin in Tris-buffered saline for 20 minutes and incubated with a monoclonal anti-TdCA antibody (GenScript, USA).

After 5 washes, the membrane was incubated for 1 hour with a secondary, HRP-conjugated antibody (Abcam, USA), washed, and then chemiluminesence was developed using Clarity substrate (BioRAD) and visualized using a Chemi- DocMP+ imaging system (BioRAD). It was confirmed that the correct fusion protein was expressed with the expected molecular weight (FIG. 5; ~78 kDa). Smaller bands were also observed with the sizes indicating cleavage of the fusion protein (TdCA about 28 kDa and Ag43 about 52 kDa).

Results

FIG. 5 shows immunoblot of samples A, B, and D, separate UTEX 2973 colonies stably transfected with TdCA-Ag43 (pSyn_6 (constitutive expression vector). Wild type (WT) included untransfected cells. The presence of a band at 78 kDa confirmed the expression of TdCA-Ag43 in the transformed cells (FIG. 5). The presence of additional bands (FIG. 5; <78 kDa) was related to cleavage fragments of the fusion protein containing the TdC Antigen.

C. Example 3: Evidence of Whole Cell Cyanobacterial Cell Carbonic Anhydrase (CA) Activity Involving Whole UTEX 2973 Cells and OMVs Overall carbonic anhydrase (CA) activity of whole cyanobacterial cells was evaluated in whole UTEX 2973 cells and OMVs.

Methods:

A colorimetric assay was used to monitor the rate of pH change caused by CA activity using phenol red as an indicator.

In step 1, whole cell samples were washed 2× with growth media, then washed 2× and resuspended in pH 8.5, 20 mM Tris-HCl. In step 2, cell density was measured optically at 750 nm ($OD_{750}$).

In step 3, in a quartz cuvette, 600 µL of a pH 8.5, 20 mM Tris-HCl and 1 mM phenol red solution was combined with a 10 µL sub-sample of the concentrated cells and 400 µL ice-cold water supersaturated with $CO_2$.

In step 4, while stirring, changes in absorbance at 570 nm over time were recorded using an Agilent Cary 3500 UV-Vis System cooled to 4° C. In step 5, the Wilbur-Anderson activity (WA) was calculated using the following:

$$WA = (t_0 - t)/t$$

where t, is the time taken for the concentrated cell sample to record a pH change from 7.5 to 6.5 (corresponding to absorbency values of 1.2 and 0.18, respectively) and $t_0$ is time taken for the blank (20 mM Tris-HCl) to record any pH change from 7.5 to 6.5.

In step 6, WA was divided by the $OD_{750}$ of the sample obtained in step 2, to account for variation in cell density across samples, and by 0.001 mL to obtain a per-volume measurement.

Results

The results as shown in FIG. 6 indicated significantly more whole cell CA activity in cells transformed with the TdCA-Ag43 construct as described in Example 2 compared to wild type cells.

D. Example 4: Proteinase K Evidence for Cell Surface Accumulation of TdCA-Ag43

Proteinase K digestion of cyanobacterial surface-displayed proteins was assessed.

Proteinase K is a cysteine protease that is impermeable to a whole/intact bacterial cell. To detect cell surface display of the TdCA protein (SEQ ID NO: 1), a proteinase K digestion of protein on the outside of whole cells was performed.

For each culture, six 1 mL samples were collected, centrifuged at 6000×g and re-suspended in phosphate buffer (pH 7.4). Next, 0, 0.1, 0.2, 0.5, 1.0, or 1.5 U proteinase K (Ferri et al. 2015) were added to each of the six samples and incubated at 37° C. for 30 minutes. The cells were then washed with PBS (pH 7.4) and an immunoblot was performed with the process as described in Example 2.

A replicate polyacrylamide gel was stained with Comassie blue as a control for total protein loading and visualized using the Gel Doc XR+ system (BioRad). Evidence was found of surface protein digestion at high proteinase K concentrations (esp. 1 U) inTdCA-Ag43 culture D. To confirm evidence of proteinase K digestion in TdCA-Ag43 replicate culture D, a follow-up proteinase K assay was performed, as described above, but with eight samples, and addition of 0, 0.1, 0.2, 0.5, 1.0, 1.5, 2.0, or 2.5 U proteinase K, as shown in FIG. 7.

Results

In the treatments of whole cell samples of clonal culture D with different concentrations of proteinase K, as shown in FIG. 7, the immunoblotting band near 78 kDa, which corresponds to the expected size of the TdCA-Ag43 fusion protein, showed significant decrease in the intensity with increasing proteinase K concentrations.

FIG. 8 provides quantitative analysis (measuring band volume/density) of the results in FIG. 7. These results suggest cell surface accumulation of TdCA-Ag43 (immunoblot for sample D; Units proteinase K/mL) since proteinase K works mostly on the cell surface.

E. Example 5: CA Activity of OMV from UTEX 2973 Cell Supernatants

This study assessed carbonic anhydrase activity of outer membrane vesicles/OMVs in UTEX 2973 cell supernatants.

Methods

OMVs were isolated from ~40 mL samples of cell culture with an OD750>1. The culture samples were centrifuged at 6000×g and supernatants were filtered using 0.22 μm syringe filters. Next, the filtered supernatants were spin-concentrated to 250-1000 μL using 50 MWCO filter units (Amicon). An ExoQuick-TC kit (SBI) was then used to pellet OMVs and re-suspend them in pH 7.4 phosphate buffer.

Total protein concentration in the samples was estimated using a microvolume spectrometer (NanoDrop). Dynamic light scattering was used to confirm that the size distribution of particles in the sample corresponds to the expected size of OMVs (e.g., 100-200 nm). CA activity assays were performed as detailed for Example 3. In this case, no normalization was performed on the measurements. The experiment was repeated four times, and the data were used to fit a linear mixed model, where, the sample type (WT, A, C, D)

was the predictor, and the date of the experiment was used as a random intercept to control for variations across the different replicate experiments.

Results

An analysis of variance was performed on the data. The results showed that there was a significant effect of sample type on the CA activity (ANOVA: F3,12=6.28; p=0.0083).

A Tukey-corrected pairwise post-hoc test indicated a significant difference of 0.24±0.07 WA units (±SE; p=0.011) between the D and wild type sample types.

As shown in FIG. 9, there was a statistically significant level of carbonic anhydrase activity on OMVs isolated from at least one of the three cyanobacterial cells expressing the Ag43-TdCA fusion protein (SEQ ID NO: 1).

F. Example 6: Liquid Chromatography-Mass Spectrometry (LC-MS) Study of SomA-TdCA Expression in UTEX 2973 Cells TdCA was fused with a *Synechococcus* outer membrane protein A, somatostatin A (somA; SEQ ID NO: 4). The coding sequence of the construct was inserted into a *Synechococcus*-specific plasmid vector with a strong, constitutive (continuous transcription) promoter at the NdeI restriction site (pSyn6; Thermo Fischer). The resulting recombinant plasmid (tSomA-TdCA-pSyn6; SEQ ID NO: 4) was transformed into the fast-growing cyanobacterium *Synechococcus elongatus* UTEX 2973 cells. As shown by Mass Spectrometry, the full length of the tSOMA-TdCA fusion protein is 67,113.57 Da.

To detect expression of the fusion protein tSomA-TdCA in transformed cyanobacteria, whole cells were lysed by vortexing with glass beads. To suppress proteolysis, complete protease inhibitor (MilliporeSigma) was added to the lysis mixture prior to lysis. Next, samples were mixed with 2× Laemmli buffer (BioRAD) and heated to 95° C. for 5 minutes. After centrifugation, samples were loaded on and electrophoresed through a 4-20% gradient SDS-PAGE gel (BioRAD). Protein was then transferred to a PVDF membrane (ImmobilonP; MilliporeSigma). The membrane was blocked with 5% bovine serum albumin in Tris-buffered saline for 20 minutes and incubated with a monoclonal anti-TdCA antibody (GenScript, USA).

After 5 washes, the membrane was incubated for 1 hour with a secondary, HRP-conjugated antibody (Abcam, USA), washed, and then chemiluminesence was developed using Clarity substrate (BioRAD) and visualized using a ChemiDocMP+ imaging system (BioRAD).

The experiment confirmed expression of the fusion protein although some of the fusion protein was cleaved, resulting in bands with smaller sizes.

9. EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents, and patent applications cited within the body of the instant specification are hereby incorporated by reference in their entirety, for all purposes.

10. SEQUENCES

| SEQ ID NO | Description | Sequence |
|-----------|-------------|----------|
| 1 | *Thermosulfurimonas dismutans* (TdCA); *Escherichia coli* (strain K12), Ag43 beta-barrel domain TdCA-Ag43 fusion protein: Ag 43 *E. coli* signal peptide (amino acid 1-52) + Td carbonic anhydrase/CA (amino acids 53-281) + linker (amino acids 282-288) + Ag43 β-chain translocator domain (amino acids 289-776): | MKRHLNTCYRLVWNHMTGAFVVASELARARGKRGGVAVALSLAAVTSLPVLAGGGHV VKWGYVGKIGPAHWGDLAHEYFMCKVGKNQSPVDINSSVTIEAQLEPINFHYRDQISGE IVNNGHTIMVVPKEDNYIVVDGKKFHLKQFHFHSPSEHTVEGKYYLLELHFVHQADDGQ LAVIGVVFDRGAEHPEIAKLWKEAPEHEGKKELKSLVNMQALLPENLDYYRYSGSLTTPP CSEGVIWLFLKNPLQISEAQAEKFKKIMGFENNRPVQPVNARKILKGSSSGSSPTNVTLAS GATWNIPDNATVQSVVDDLSHAGQIHFTSTRTGKFVPATLKVKNLNGQNGTISLRVRPD MAQNNADRLVIDGGRATGKTILNLVNAGNSASGLATSGKGIQVVEAINGATTEEGAFV QGNRLQAGAFNYSLNRDSDESWYLRSENAYRAEVPLYASMLTQAMDYDRIVAGSRSH QTGVNGENNSVRLSIQGGHLGHDNNGGIARGATPESSGSYGFVRLEGDLMRTEVAGM SVTAGVYGAAGHSSVDVKDDDGSRAGTVRDDAGSLGGYLNLVHTSSGLWADIVAQGT RHSMKASSDNNDFRARGWGWLGSLETGLPFSITDNLMLEPQLQYTWQGLSLDDGKDN AGYVKFGHGSAQHVRAGFRLGSHNDMTFGEGTSSRAPLRDSAKHSVSELPVNWWVQ PSVIRTFSSRGDMRVGTSTAGSGMTFSPSQNGTSLDLQAGLEARVRENITLGVQAGYAH SVSGSSAEGYNGQATLNVTF |
| 2 | TdCA-Ag43 fusion protein: *Synechococcus* PCC 7942 27-AA signal peptide (amino acids 1-27) + Td carbonic anhydrase/CA (amino acids 28-256) + linker (amino acids 257-263) + Ag43 β-chain translocator domain (amino acids 264-751) | MKRLFSALLLAPAIAGVAAGAANANGLGGGHVVKWGYVGKIGPAHWGDLAHEYFMC KVGKNQSPVDINSSVTIEAQLEPINFHYRDQISGEIVNNGHTIMVVPKEDNYIVVDGKKF HLKQFHFHSPSEHTVEGKYYLLELHFVHQADDGQLAVIGVVFDRGAEHPEIAKLWKEAP EHEGKKELKSLVNMQALLPENLDYYRYSGSLTTPPCSEGVIWLFLKNPLQISEAQAEKFKKI MGFENNRPVQPVNARKILKGSSSGSSPTNVTLASGATWNIPDNATVQSVVDDLSHAGQ IHFTSTRTGKFVPATLKVKNLNGQNGTISLRVRPDMAQNNADRLVIDGGRATGKTILNLV NAGNSASGLATSGKGIQVVEAINGATTEEGAFVQGNRLQAGAFNYSLNRDSDESWYLR SENAYRAEVPLYASMLTQAMDYDRIVAGSRSHQTGVNGENNSVRLSIQGGHLGHDNN GGIARGATPESSGSYGFVRLEGDLMRTEVAGMSVTAGVYGAAGHSSVDVKDDDGSRA GTVRDDAGSLGGYLNLVHTSSGLWADIVAQGTRHSMKASSDNNDFRARGWGWLGSL ETGLPFSITDNLMLEPQLQYTWQGLSLDDGKDNAGYVKFGHGSAQHVRAGFRLGSHN DMTFGEGTSSRAPLRDSAKHSVSELPVNWWVQPSVIRTFSSRGDMRVGTSTAGSGMT FSPSQNGTSLDLQAGLEARVRENITLGVQAGYAHSVSGSSAEGYNGQATLNVTF |
| 3 | TdCA-Hbp fusion protein: signal peptide (Daleke-Schermerhorn et al.) (amino acids 1-53) + Td carbonic anhydrase/CA (amino acids 54-282) + linker (amino acids 283-289) + truncated Hbp passenger domain: minus the N-terminal D1 subdomain + the remaining subdomains + the b domain (amino acids 290-1359) | MNRIYSLRYSAVARGFIAVSEFARKCVHKSVRRLCFPVLLLIPVLFSAGSLAGGGGHVVKW GYVGKIGPAHWGDLAHEYFMCKVGKNQSPVDINSSVTIEAQLEPINFHYRDQISGEIVN NGHTIMVVPKEDNYIVVDGKKFHLKQFHFHSPSEHTVEGKYYLLELHFVHQADDGQLAV IGVVFDRGAEHPEIAKLWKEAPEHEGKKELKSLVNMQALLPENLDYYRYSGSLTTPPCSE GVIWLFLKNPLQISEAQAEKFKKIMGFENNRPVQPVNARKILKGSSSGSSNDAPVTFRTS EGGALEWSFNSSTGAGALTQGTTTYAMHGQQGNDLNAGKNLIFQGQNGQINLKDSVS QGAGSLTFRDNYTVTTSNGSTWTGAGIVVDNGVSVNWQVNGVKGDNLHKIGEGTLTV QGTGINEGGLKVGDGKVVLNQQADNKGQVQAFSSVNIASGRPTVVLTDERQVNPDTV SWGYRGGTLDVNGNSLTFHQLKAADYGAVLANNVDKRATITLDYALRADKVALNGWS ESGKGTAGNLYKYNNPYTNTTDYFILKQSTYGYFPTDQSSNATWEFVGHSQGDAQKLVA DRFNTAGYLFHGQLKGNLNVDNRLPEGVTGALVMDGAADISGTFTQENGRLTLQGHP VIHAYNTQSVADKLAASGDHSVLTQPTSFSQEDWENRSFTFDRLSLKNTDFGLGRNATL NTTIQADNSSVTLGDSRVFIDKNDGQGTAFTLEEGTSVATKDADKSVFNGTVNLDNQSV LNINDIFNGGIQANNSTVNISSDSAVLGNSTLTSTALNLNKGANALASQSFVSDGPVNISD ATLSLNSRPDEVSHTLLPVYDYAGSWNLKGDDARLNVGPYSMLSGNINVQDKGTVTLG GEGELSPDLTLQNQMLYSLFNGYRNIWSGSLNAPDATVSMTDTQWSMNGNSTAGNM KLNRTIVGFNGGTSPFTTLTTDNLDAVQSAFVMRTDLNKADKLVINKSATGHDNSIWVN FLKKPSNKDTLDIPLVSAPEATADNLFRASTRVVGFSDVTPILSVRKEDGKKEWVLDGYQV ARNDGQGKAAATFMHISYNNFITEVGSLNKRMGDLRDINGEAGTWVRLLNGSGSADG GFTDHYTLLQMGADRKHELGSMDLFTGVMATYTDTDASADLYSGKTKSWGGGFYASG LFRSGAYFDVIAKYIHNENKYDLNFAGAGKQNFRSHSLYAGAEVGYRYHLTDTTFVEPQA ELVWGRLQGQTFNWNDSGMDVSMRRNSVNPLVGRTGVVSGKTFSGKDWSLTARAG LHYEFDLTDSADVHLKDAAGEHQINGRKDSRMLYGVGLNARFGDNTRLGLEVERSAFGK YNTDDAINANIRYSF |
| 4 | SomA-TdCA fusion protein: Truncated *Synechococcus* SomA with the C-terminus at amino acid position 382 | MKRLFSALLLAPAIAGVAAGAANANGLSTEQLQKIDAVTPNGITSGQITSITELSDVKPTD WAYQALQSLVERYGCIVGYPDRTYRGSRPLSRYEFAAGLNACLDKVIEFAASKEDLDTLKR LTEEFQAELATLRGRVDSLEARVKELEATRFSTTTKLQGEVIFSLDAVANTAGNERNQDG AVSFGNRVSLNLNTSFTGKDLLLTRLRARNIETIQQRLSPGFNPSGSRLDYDGTGSPGVPN SANTFFLDKLLYRFPVGDVSFTVGTAGVQPQDYGLSDATFFSGPANTKAFKYVGAGVYA DTRDADTAGVGFNWKASKNFSFQAGYINRNSADVSTVNSGGVFGFTPTGTGTNSWDV |

| SEQ ID NO | Description | Sequence |
|---|---|---|
| | (located at the fifth cell-surface exposed loop) (amino acids 1-382) + Td carbonic anhydrase/CA (amino acids 383-613) | NAQVKYQTDNNKFRVALAYALRNGGGHVVKWGYVGKIGPAHWGDLAHEYFMCKVG KNQSPVDINSSVTIEAQLEPINFHYRDQISGEIVNNGHTIMVVPKEDNYIVVDGKKFHLKQ FHFHSPSEHTVEGKYYLLELHFVHQADDGQLAVIGVVFDRGAEHPEIAKLWKEAPEHEG KKELKSLVNMQALLPENLDYYRYSGSLTTPPCSEGVIWLFLKNPLQISEAQAEKFKKIMGF ENNRPVQPVNARKILK |
| 5 | MipA-TdCA fusion protein: truncated MipA with the C-terminus at amino acid position 140 located at the third cell-surface exposed loop (amino acids 1-140) + linker (amino acids 141-163) + Td carbonic anhydrase/CA (amino acids 164-392) | MTKLKLLALGVLIATSAGVAHAEGKFSLGAGVGVVEHPYKDYDTDVYPVPVINYEGDNF WFRGLGGGYYLWNDATDKLSITAYWSPLYFKAKDSGDHQMRHLDDRKSTMMAGLSY AHFTQYGYLRTTLAGDTLDNSNGIV GGGGSGGSGGGGSGGGGSGGGGS GGGHVVKWGYVGKIGPAHWGDLAHEYFMCKVGKNQSPVDINSSVTIEAQLEPINFH YRDQISGEIVNNGHTIMVVPKEDNYIVVDGKKFHLKQFHFHSPSEHTVEGKYYLLELHF VHQADDGQLAVIGVVFDRGAEHPEIAKLWKEAPEHEGKKELKSLVNMQALLPENLDY YRYSGSLTTPPCSEGVIWLFLKNPLQISEAQAEKFKKIMGFENNRPVQPVNARKILK |
| 6 | INPN-RE-TdCA fusion protein: pelB signal peptide (amino acids 1-22) + INPN (: underlining: front two sub-repeats in the middle repeat domain of ice nucleoprotein) (amino acids 23-233) + linker (amino acids 234-238) + Td carbonic anhydrase/CA (amino acids 239-467) + His-Tag (amino acids 468-473) | MKYLLPTAAAGLLLLAAQPAMAMTLDKALVLRTCANNMADHCGLIWPASGTVESRYW QSTRRHENGLVGLLWGAGTSAFLSVHADARWIVCEVAVADIISLEEPGMVKFPRAEVVH VGDRISASHFISARQADPASTSTSTSTLTPMPTAIPTPMPAVASVTLPVAEQARHEVFD VASVSAAAAPVNTLPVTTPQNLQTATYGSTLSGDNHSRLIAGYGSNETAGNHSDLIGGG GSGGGHVVKWGYVGKIGPAHWGDLAHEYFMCKVGKNQSPVDINSSVTIEAQLEPINFH YRDQISGEIVNNGHTIMVVPKEDNYIVVDGKKFHLKQFHFHSPSEHTVEGKYYLLELHFV HQADDGQLAVIGVVFDRGAEHPEIAKLWKEAPEHEGKKELKSLVNMQALLPENLDYYRY SGSLTTPPCSEGVIWLFLKNPLQISEAQAEKFKKIMGFENNRPVQPVNARKILKHHHHHH |
| 7 | Td carbonic anhydrase | GGGHVVKWGYVGKIGPAHWGDLAHEYFMCKVGKNQSPVDINSSVTIEAQLEPINFHYR DQISGEIVNNGHTIMVVPKEDNYIVVDGKKFHLKQFHFHSPSEHTVEGKYYLLELHFVHQ ADDGQLAVIGVVFDRGAEHPEIAKLWKEAPEHEGKKELKSLVNMQALLPENLDYYRYSG SLTTPPCSEGVIWLFLKNPLQISEAQAEKFKKIMGFENNRPVQPVNARKILK |
| 8 | Ag43 b-chain translocator domain | PTNVTLASGATWNIPDNATVQSVVDDLSHAGQIHFTSTRTGKFVPATLKVKNLNGQNG TISLRVRPDMAQNNADRLVIDGGRATGKTILNLVNAGNSASGLATSGKGIQVVEAINGA TTEEGAFVQGNRLQAGAFNYSLNRDSDESWYLRSENAYRAEVPLYASMLTQAMDYDRI VAGSRSHQTGVNGENNSVRLSIQGGHLGHDNNGGIARGATPESSGSYGFVRLEGDLMR TEVAGMSVTAGVYGAAGHSSVDVKDDDGSRAGTVRDDAGSLGGYLNLVHTSSGLWA DIVAQGTRHSMKASSDNNDFRARGWGWLGSLETGLPFSITDNLMLEPQLQYTWQGLS LDDGKDNAGYVKFGHGSAQHVRAGFRLGSHNDMTFGEGTSSRAPLRDSAKHSVSELPV NWWVQPSVIRTFSSRGDMRVGTSTAGSGMTFSPSQNGTSLDLQAGLEARVRENITLGV QAGYAHSVSGSSAEGYNGQATLNVTF |
| 9 | Truncated Hbp passenger domain: minus the N-terminal D1 subdomain + the remaining subdomains + the b domain | NDAPVTFRTSEGGALEWSFNSSTGAGALTQGTTTYAMHGQQGNDLNAGKNLIFQGQN GQINLKDSVSQGAGSLTFRDNYTVTTSNGSTWTGAGIVVDNGVSVNWQVNGVKGDNL HKIGEGTLTVQGTGINEGGLKVGDGKVVLNQQADNKGVQAFSSVNIASGRPTVVLTD ERQVNPDTVSWGYRGGTLDVNGNSLTFHQLKAADYGAVLANNVDKRATITLDYALRAD KVALNGWSESGKGTAGNLYKYNNPYTNTTDYFILKQSTYGYFPTDQSSNATWEFVGHS QGDAQKLVADRFNTAGYLFHGQLKGNLVNDNRLPEGVTGALVMDGAADISGTFTQEN GRLTLQGHPVIHAYNTQSVADKLAASGDHSVLTQPTSFSQEDWENRSFTFDRLSLKNTD FGLGRNATLNTTIQADNSSVTLGDSRVFIDKNDGQGTAFTLEEGTSVATKDADKSVFNG TVNLDNQSVLNINDIFNGGIQANNSTVNISSDSAVLGNSTLTSTALNLNKGANALASQSF VSDGPVNISDATLSLNSRPDEVSHTLLPVYDYAGSWNLKGDDARLNVGPYSMLSGNINV QDKGTVTLGGEGELSPDLTLQNQMLYSLFNGYRNIWSGSLNAPDATVSMTDTQWSM NGNSTAGNMKLNRTIVGFNGGTSPFTTLTTDNLDAVQSAFVMRTDLNKADKLVINKSA TGHDNSIWVNFLKKPSNKDTLDIPLVSAPEATADNLFRASTRVVGFSDVTPILSVRKEDGK KEWVLDGYQVARNDGQGKAAATFMHISYNNFITEVGSLNKRMGDLRDINGEAGTWV |

| SEQ ID NO | Description | Sequence |
|---|---|---|
| | | RLLNGSGSADGGFTDHYTLLQMGADRKHELGSMDLFTGVMATYTDTDASADLYSGKTK SWGGGFYASGLFRSGAYFDVIAKYIHNENKYDLNFAGAGKQNFRSHSLYAGAEVGYRYH LTDTTFVEPQAELVWGRLQGQTFNWNDSGMDVSMRRNSVNPLVGRTGVVSGKTFSG KDWSLTARAGLHYEFDLTDSADVHLKDAAGEHQINGRKDSRMLYGVGLNARFGDNTRL GLEVERSAFGKYNTDDAINANIRYSF |
| 10 | Truncated *Synechococcus* SomA with the C-terminus at amino acid position 382 | MKRLFSALLLAPAIAGVAAGAANANGLSTEQLQKIDAVTPNGITSGQITSITELSDVKPTD WAYQALQSLVERYGCIVGYPDRTYRGSRPLSRYEFAAGLNACLDKVIEFAASKEDLDTLKR LTEEFQAELATLRGRVDSLEARVKELEATRFSTTTKLQGEVIFSLDAVANTAGNERNQDG AVSFGNRVSLNLNTSFTGKDLLLTRLRARNIETIQQRLSPGFNPSGSRLDYDGTGSPGVPN SANTFFLDKLLYRFPVGDVSFTVGTAGVQPQDYGLSDATFFSGPANTKAFKYVGAGVYA DTRDADTAGVGFNWKASKNFSFQAGYINRNSADVSTVNSGGVFGFTPTGTGTNSWDV NAQVKYQTDNNKFRVALAYALRN |
| 11 | Truncated MipA with the C-terminus at amino acid position 140 located at the third cell-surface exposed loop | MTKLKLLALGVLIATSAGVAHAEGKFSLGAGVGVVEHPYKDYDTDVYPVPVINYEGDNF WFRGLGGGYYLWNDATDKLSITAYWSPLYFKAKDSGDHQMRHLDDRKSTMMAGLSY AHFTQYGYLRTTLAGDTLDNSNGIV |
| 12 | INPN from Pseudomonas syringae | MTLDKALVLRTCANNMADHCGLIWPASGTVESRYWQSTRRHENGLVGLLWGAGTSAF LSVHADARWIVCEVAVADIISLEEPGMVKFPRAEVVHVGDRISASHFISARQADPASTSTS TSTSTLTPMPTAIPTPMPAVASVTLPVAEQARHEVFDVASVSAAAAPVNTLPVTTPQNL QTATYGSTLSGDNHSRLIAGYGSNETAGNHSDLI |
| 13 | Ag 43 *E. coli* signal peptide | MKRHLNTCYRLVWNHMTGAFVVASELARARGKRGGVAVALSLAAVTSLPVLA |
| 14 | *Synechococcus* PCC 7942 27-AA signal peptide | MKRLFSALLLAPAIAGVAAGAANANGL |
| 15 | pelB signal peptide | MKYLLPTAAAGLLLLAAQPAMA |
| 16 | signal peptide | MNRIYSLRYSAVARGFIAVSEFARKCVHKSVRRLCFPVLLLIPVLFSAGSLAG |
| 17 | Linker | GSSSGSS |
| 18 | G4S linker | GGGGS |
| 19 | G4SGGS(G4S)3 linker | GGGGSGGSGGGGSGGGGSGGGGS |
| 20 | sp\|P39180\|AG43_ *ECOLI* Antigen 43 OS = *Escherichia coli* (strain K12) OX = 83333 GN = flu PE = 1 SV = 3 | MKRHLNTCYRLVWNHMTGAFVVASELARARGKRGGVAVALSL AAVTSLPVLAADIVVHPGETVNGGTLANHDNQIVFGTTNGMT ISTGLEYGPDNEANTGGQWVQDGGTANKTTVTSGGLQRVNPG GSVSDTVISAGGGQSLQGRAVNTTLNGGEQWMHEGAIATGTV INDKGWQVVKPGTVATDTVVNTGAEGGPDAENGDTGQFVRGD AVRTTINKNGRQIVRAEGTANTTVVYAGGDQTVHGHALDTTL NGGYQYVHNGGTASDTVVNSDGWQIVKNGGVAGNTTVNQKGR LQVDAGGTATNVTLKQGGALVTSTAATVTGINRLGAFSVVEG KADNVVLENGGRLDVLTGHTATNTRVDDGGTLDVRNGGTATT VSMGNGGVLLADSGAAVSGTRSDGKAFSIGGGQADALMLEKG SSFTLNAGDTATDTTVNGGLFTARGGTLAGTTTLNNGAILTL SGKTVNNDTLTIREGDALLQGGSLTGNGSVEKSGSGTLTVSN TTLTQKAVNLNEGTLTLNDSTVTTDVIAQRGTALKLTGSTVL NGAIDPTNVTLASGATWNIPDNATVQSVVDDLSHAGQIHFTS TRTGKFVPATLKVKNLNGQNGTISLRVRPDMAQNNADRLVID GGRATGKTILNLVNAGNSASGLATSGKGIQVVEAINGATTEE GAFVQGNRLQAGAFNYSLNRDSDESWYLRSENAYRAEVPLYA SMLTQAMDYDRIVAGSRSHQTGVNGENNSVRLSIQGGHLGHD NNGGIARGATPESSGSYGFVRLEGDLMRTEVAGMSVTAGVYG AAGHSSVDVKDDDGSRAGTVRDDAGSLGGYLNLVHTSSGLWA DIVAQGTRHSMKASSDNNDFRARGWGWLGSLETGLPFSITDN LMLEPQLQYTWQGLSLDDGKDNAGYVKFGHGSAQHVRAGFRL GSHNDMTFGEGTSSRAPLRDSAKHSVSELPVNWWVQPSVIRT FSSRGDMRVGTSTAGSGMTFSPSQNGTSLDLQAGLEARVREN ITLGVQAGYAHSVSGSSAEGYNGQATLNVT |
| 21 | TdCA-Ag43 construct (Tdcarbonic anhydrase + Ag43 | MKRHLNTCYRLVWNHMTGAFVVASELARARGKRGGVAVALSL AKKFIGGLVGSLMIGGVALAGGGHVVKWGYVGKIGPAHWGDL AHEYFMCKVGKNQSPVDINSSVTIEAQLEPINFHYRDQISGE IVNNGHTIMVVPKEDNYIVVDGKKFHLKQFHFHSPSEHTVEG |

| SEQ ID NO | Description | Sequence |
|---|---|---|
|  | β-chain translocator domain) MW fusion protein-signal peptide/SP: 79577.67 Da (80 kDa) MW TdCA:27780.93 Da (28 kDa) | KYYLLELHFVHQADDGQLAVIGVVFDRGAEHPEIAKLWKEAP EHEGKKELKSLVNMQALLPENLDYYRYSGSLTTPPCSEGVIW LFLKNPLQISEAQAEKFKKIMGFENNRPVQPVNARKILKGS SSGSSTNVTLASGATWNIPDNATVQSVVDDLS<u>HAGQIHF</u>TS TRTGKFVPATLKVKNLNGQNGTISLRVRPDMAQNNADRLVID GGRATGKTILNLVNAGNSASGLATSGKGIQVVEAINGATTEE GAFVQGNRLQAGAFNYSLNRDSDESWYLRSENAYRAEVPLYA SMLTQAMDYDRIVAGSRSHQTGVNGENNSVRLSIQGGHLGHD NNGGIARGATPESSGSYGFVRLEGDLMRTEVAGMSVTAGVYG AAGHSSVDVKDDDGSRAGTVRDDAGSLGGYLNLVHTSSGLWA DIVAQGTRHSMKASSDNNDFRARGWGWLGSLETGLPFSITDN LMLEPQLQYTWQGLSLDDGKDNAGYVKFGHGSAQHVRAGFRL GSHNDMTFGEGTSSRAPLRDSAKHSVSELPVNWWVQPSVIRT FSSRGDMRVGTSTAGSGMTFSPSQNGTSLDLQAGLEARVREN ITLGVQAGYAHSVSGSSAEGYNGQATLNVT |
| 22 | signal peptide (red) | MKRHLNTCYRLVWNHMTGAFVVASELARARGKRGGV AVALSLA |
| 23 | Ag43 b-chain translocator domain | PTNVTLASGATWNIPDNATVQSVVDDLSHAGQIHFTSTRTGKFVPATLK VKNLNGQNGTISLRVRPDMAQNNADRLVIDGGRATGKTILNLVNAGNS ASGLATSGKGIQVVEAINGATTEEGAFVQGNRLQAGAFNYSLNRDSDES WYLRSENAYRAEVPLYASMLTQAMDYDRIVAGSRSHQTGVNGENNSV RLSIQGGHLGHDNNGGIARGATPESSGSYGFVRLEGDLMRTEVAGMSVT AGVYGAAGHSSVDVKDDDGSRAGTVRDDAGSLGGYLNLVHTSSGLWA DIVAQGTRHSMKASSDNNDFRARGWGWLGSLETGLPFSITDNLMLEPQL QYTWQGLSLDDGKDNAGYVKFGHGSAQHVRAGFRLGSHNDMTFGEGT SSRAPLRDSAKHSVSELPVNWWVQPSVIRTFSSRGDMRVGTSTAGSGMT FSPSQNGTSLDLQAGLEARVREN ITLGVQAGYAHSVSGSSAEGYNGQATLNVT |
| 24 | pSyn6-TdCA-Ag43 pSyn_6 plasmid vector DNA (codon optimized for *Synechococcus elongatus* strain UTEX 2973) 6795 nucleotides including 2328 nucleotides corresponding to SEQ 1 | CTGGTTGGCTTGGTTTCATCAGCCATCCGCTTGCCCTCATCTGTTACGCCGGCGGTAG CCGGCCAGCCTCGCAGAGCAGGATTCCCGTTGAGCACCGCCAGGTGCGAATAAGGG ACAGTGAAGAAGGAACACCCGCTCGCGGGTGGGCCTACTTCACCTATCCTGCCCGGC TGACGCCGTTGGATACACCAAGGAAAGTCTACACGAACCCTTTGGCAAATCCTGTA TATCGTGCGAAAAAGGATGGATATACCGAAAAAATCGCTATAATGACCCCGAAGCA GGGTTATGCAGCGGAAGATCGATAATCTCATGACCAAAATCCCTTAACGTGAGTTTT CGTTCCACTGAGCGTCAGACCCCGTATAAAAGATCAAAGGATCTTCTTGAGATCCTTT TTTTCTGCGCGTAATCTGCTGCTTGCAAACAAAAAAACCACCGCTACCAGCGGTGGTT TGTTTGCCGGATCAAGAGCTACCAACTCTTTTTCCGAAGGTAACTGGCTTCAGCAGA GCGCAGATACCAAATACTGTTCTTCTAGTGTAGCCGTAGTTAGGCCACCACTTCAAGA ACTCTGTAGCACCGCCTACATACCTCGCTCTGCTAATCCTGTTACCAGTGGCTGCTGC CAGTGGCGATAAGTCGTGTCTTACCGGGTTGGACTCAAGACGATAGTTACCGGATAA GGCGCAGCGGTCGGGCTGAACGGGGGGTTCGTGCACACAGCCCAGCTTGGAGCGA ACGACCTACACCGAACTGAGATACCTACAGCGTGAGCTATGAGAAAGCGCCACGCTT CCCGAAGGGAGAAAGGCGGACAGGTATCCGGTAAGCGGCAGGGTCGGAACAGGA GAGCGCACGAGGGAGCTTCCAGGGGGAAACGCCTGGTATCTTTATAGTCCTGTCGG GTTTCGCCACCTCTGACTTGAGCGTCGATTTTTGTGATGCTCGTCAGGGGGGCGGAG CCTATGGAAAAACGCCAGCAACGCGGCCTTTTTACGGTTCCTGGCCTTTTGCTGGCCT TTTGCTCACATGTGTGCTGGGCCCCAATGCCTTCTCCAAGGGCGGCATTCCCCTGACT GTTGAAGGCGTTGCCAATATCAAGATTGCTGGGGAAGAACCGACCATCCACAACGC GATCGAGCGGCTGCTTGGCAAAAACCGTAAGGAAATCGAGCAAATTGCCAAGGAGA CCCTCGAAGGCAACTTGCGTGGTGTTTTAGCCAGCCTCACGCCGGAGCAGATCAACG AGGACAAAATTGCCTTTGCCAAAAGTCTGCTGGAAGAGGCGGAGGATGACCTTGAG CAGCTGGGTCAAGTCCTCGATACGCTGCAAGTCCAGAACATTTCCGATGAGGTCGGT TATCTCTCGGCTAGTGGACGCAAGCAGCGGGCTGATCTGCAGCGAGATGCCCGAATT GCTGAAGCCGATGCCCAGGCTGCCTCTGCGATCCAAACGGCCGAAATGACAAGAT CACGGCCCTGCGTCGGATCGATCGCGATGTAGCGATCGCCCAAGCCGAGGCCGAGC GCCGGATTCAGGATGCGTTGACGCGGCGCGAAGCGGTGGTGGCCGAAGCTGAAGC GGACATTGCTACCGAAGTCGCTCGTAGCCAAGCAGAACTCCCTGTGCAGCAGGAGC GGATCAAACAGGTGCAGCAGCAACTTCAAGCCGATGTGATCGCCCCAGCTGAGGCA GCTTGTAAACGGGCGATCGCGGAAGCGCGGGGGGCCGCCGCCCGTATCGTCGAAG ATGGAAAAGCTCAAGCGGAAGGGACCCAACGGCTGGCGGAGGCTTGGCAGACCGC TGGTGCTAATGCCCGCGACATCTTCCTGCTCCAGAAGTCTAGATAATCCCTAGCGATC GCAAGTCCAAAGGTTGTCTACAATCAATATCCAAGCATCAAAAAGCGCCCCATTCGA GGCGCTTTTTGATTATTCAGACTGCTGTAATTCCGGCAATTAGGTTATTTGCCGACTA CCTTGGTGATCTCGCCTTTCACGTAGTGGACAAATTCTTCCAACTGATCTGCGCGCGA GGCCAAGCGATCTTCTTCTTGTCCAAGATAAGCCTGTCTAGCTTCAAGTATGACGGGC TGATACTGGGCCGGCAGGCGCTCCATTGCCCAGTCGGCAGCGACATCTTCGGCGCG ATTTTGCCGGTTACTGCGCTGTACCAAATGCGGGACAACGTAAGCACTACATTTCGCT CATCGCCAGCCCAGTCGGGCGGCGAGTTCCATAGCGTTAAGGTTTCATTTAGCGCCT CAAATAGATCCTGTTCAGGAACCGGATCAAAGAGTTCCTCCGCCGCTGGACCTACCA AGGCAACGCTATGTTCTCTTGCTTTTGTCAGCAAGATAGCCAGATCAATGTCGATCGT GGCTGGCTCGAAGATACCAGCAAGAATGTCATTGCGCTGCCATTCTCAAATTGCAG TTCGCGCTTAGCTGGATAACGCCACGGAATGATGTCGTCGTGCACAACAATGGTGAC |

| SEQ ID NO | Description | Sequence |
|---|---|---|
| | | TTCTACAGCGCGGAGAATCTCGCTCTCTCCAGGGGAAGCCGAAGTTTCCAAAAGGTC |
| | | GTTGATCAAAGCTCGCCGCGTTGTTTCATCAAGCCTTACGGTCACCGTAACCAGCAAA |
| | | TCAATATCACTGTGTGGCTTCAGGCCGCCATCCACTGCGGAGCCGTACAAATGTACG |
| | | GCCAGCAACGTCGGTTCGAGATGGCGCTCGATGACGCCAACTACCTCTGATAGTTGA |
| | | GTCGATACTTCGGCGATCACCGCTTCCCTCATAATGTTTAACTTTGTTTTAGGGCGACT |
| | | GCCCTGCTGCGTAACATCGTTGCTGCTCCATAACATCAAACATCGACCCACGGCGTAA |
| | | CGCGCTTGCTGCTTGGATGCCCGAGGCATAGACTGTACCCCAAAAAAACAGTCATAA |
| | | CAAGCCATGAAAACCGCCACTGCGCCGTTACCACCGCTGCGTTCGGTCAAGGTTCTG |
| | | GACCAGTTGCGTGAGCGCATACGCTACTTGCATTACAGCTTACGAACCGAACAGGCT |
| | | TATGTCCACTGGGTTCGTGCCTTCATCCGTTTCCACGGTGTGCGTCACCCGGCAACCT |
| | | TGGGTAGCAGCGAAGTCGAGGCATTTCTGTCCTGGCTGGCTATTTAGCGTCTTCTAAT |
| | | CCAGTGTAGACAGTAGTTTTGGCTCCGTTGAGCACTGTAGCCTTGGGCGATCGCTCT |
| | | AAACATTACATAAATTCACAAAGTTTTCGTTACATAAAAATAGTGTCTACTTAGCTAA |
| | | AAATTAAGGGTTTTTTACACCTTTTTGACAGTTAATCTCCTAGCCTAAAAAGCAAGAG |
| | | TTTTTAACTAAGACTCTTGCCCTTTACAACCTCGAAGGAGCGTCAGATCTCATATGAA |
| | | ACGCCACCTGAACACCTGCTACCGCCTGGTGTGGAACCACATGACCGGCGCCTTTGT |
| | | GGTGGCCAGCGAACTGGCCCGCGCCCGCGGCAAACGCGGCGGCGTGGCCGTGGCC |
| | | CTGAGCCTGGCCGCCGTGACCAGCCTGCCCGTGCTGGCCGGCGGCGGCCACGTGGT |
| | | GAAATGGGGCTACGTGGGCAAAATCGGCCCCGCCCACTGGGGCGATCTGGCCCACG |
| | | AATACTTTATGTGCAAAGTGGGCAAAAACCAGAGCCCCGTGGATATCAACAGCAGC |
| | | GTGACCATCGAAGCCCAGCTGGAACCCATCAACTTTCACTACCGCGATCAGATCAGC |
| | | GGCGAAATCGTGAACAACGGCCACACCATCATGGTGGTGCCCAAAGAAGATAACTA |
| | | CATCGTGGTGGATGGCAAAAAATTTCACCTGAAACAGTTTCACTTTCACAGCCCCAGC |
| | | GAACACACCGTGGAAGGCAAATACTACCTGCTGGAACTGCACTTTGTGCACCAGGCC |
| | | GATGATGGCCAGCTGGCCGTGATCGGCGTGGTGTTTGATCGCGGCGCCGAACACCC |
| | | CGAAATCGCCAAACTGTGGAAAGAAGCCCCCGAACACGAAGGCAAAAAAGAACTGA |
| | | AAAGCCTGGTGAACATGCAGGCCCTGCTGCCCGAAAACCTGGATTACTACCGCTACA |
| | | GCGGCAGCCTGACCACCCCCCCCTGCAGCGAAGGCGTGATCTGGCTGTTTCTGAAAA |
| | | ACCCCCTGCAGATCAGCGAAGCCCAGGCCGAAAAATTTAAAAAAATCATGGGCTTTG |
| | | AAAACAACCGCCCCGTGCAGCCCGTGAACGCCCGCAAAATCCTGAAAGGCAGCAGC |
| | | AGCGGCAGCAGCCCCACCAACGTGACCCTGGCCAGCGGCGCCCACCTGGAACATCCC |
| | | CGATAACGCCACCGTGCAGAGCGTGGTGGATGATCTGAGCCACGCCGGCCAGATCC |
| | | ACTTTACCAGCACCCGCACCGGCAAATTTGTGCCCGCCACCCTGAAAGTGAAAAACC |
| | | TGAACGGCCAGAACGGCACCATCAGCCTGCGCGTGCGCCCCGATATGGCCCAGAAC |
| | | AACGCCGATCGCCTGGTGATCGATGGCGGCCGCGCCACCGGCAAAACCATCCTGAA |
| | | CCTGGTGAACGCCGGCAACAGCGCCAGCGGCCTGGCCACCAGCGGCAAAGGCATCC |
| | | AGGTGGTGGAAGCCATCAACGGCGCCACCACCGAAGAAGGCGCCTTTGTGCAGGGC |
| | | AACCGCCTGCAGGCCGGCGCCTTTAACTACAGCCTGAACCGCGATAGCGATGAAAG |
| | | CTGGTACCTGCGCAGCGAAAACGCCTACCGCGCCGAAGTGCCCCTGTACGCCAGCAT |
| | | GCTGACCCAGGCCCATGGATTACGATCGCATCGTGGCCGGCAGCCGCAGCCACCAGA |
| | | CCGGCGTGAACGGCGAAAACAACAGCGTGCGCCTGAGCATCCAGGGCGGCCACCTG |
| | | GGCCACGATAACAACGGCGGCATCGCCCGCGGCGCCACCCCCCGAAAGCAGCGGCAG |
| | | CTACGGCTTTGTGCGCCTGGAAGGCGATCTGATGCGCACCGAAGTGGCCGGCATGA |
| | | GCGTGACCGCCGGCGTGTACGGCGCCGCCGGCCACAGCAGCGTGGATGTGAAAGAT |
| | | GATGATGGCAGCCGCGCCGGCACCGTGCGCGATGATGCCGGCAGCCTGGGCGGCTA |
| | | CCTGAACCTGGTGCACACCAGCAGCGGCCTGTGGGCCGATATCGTGGCCCAGGGCA |
| | | CCCGCCACAGCATGAAAGCCAGCAGCGATAACAACGATTTTCGCGCCCGCGGCTGG |
| | | GGCTGGCTGGGCAGCCTGGAAACCGGCCTGCCCTTTAGCATCACCGATAACCTGATG |
| | | CTGGAACCCCAGCTGCAGTACACCTGGCAGGGCCTGAGCCTGGATGATGGCAAAGA |
| | | TAACGCCGGCTACGTGAAATTTGGCCACGGCAGCGCCCAGCACGTGCGCGCCGGCT |
| | | TTCGCCTGGGCAGCCACAACGATATGACCTTTGGCGAAGGCACCAGCAGCCGCGCCC |
| | | CCCTGCGCGATAGCGCCAAACACAGCGTGAGCGAACTGCCCGTGAACTGGTGGGTG |
| | | CAGCCCAGCGTGATCCGCACCTTTAGCAGCCGCGGCGATATGCGCGTGGGCACCAG |
| | | CACCGCCGGCAGCGGCATGACCTTTAGCCCCAGCCAGAACGGCACCAGCCTGGATCT |
| | | GCAGGCCGGCCTGGAAGCCCGCGTGCGCGAAAACATCACCCTGGGCGTGCAGGCCG |
| | | GCTACGCCCACAGCGTGAGCGGCAGCAGCGCCGAAGGCTACAACGGCCAGGCCACC |
| | | CTGAACGTGACCTTTTTAAcatatgCACCACCACCATCACCACGAAAACCTGTACTTTCAG |
| | | GGCAAGCTTCGAATTCCCGGATCCGCGGTACCAGGCAAACCCATCCCCAACCCCCTG |
| | | CTGGGCCTGGATAGCACCGGTGGTGGTCACCACCACCATCACCACTAGAGTACTGTA |
| | | TGCATCGAGTGCCTGGCGGCAGTAGCGCGGTGGTCCCACCTGACCCCATGCCGAACT |
| | | CAGAAGTGAAACGCCGTAGCGCCGATGGTAGTGTGGGGTCTCCCCATGCGAGAGTA |
| | | GGGAACTGCCAGGCATCAAATAAAACGAAAGGCTCAGTCGAAAGACTGGGCCTTCT |
| | | CGAGTCCCTGCTCGTCACGCTTTCAGGCACCGTGCCAGATATCGACGTGGAGTCGAT |
| | | CACTGTGATTGGCGAAGGGGAAGGCAGCGCTACCCAAATCGCTAGCTTGCTGGAGA |
| | | AGCTGAAACAAACCACGGGCATTGATCTGGCGAAATCCCTACCGGGTCAATCCGACT |
| | | CGCCCGCTGCGAAGTCCTAAGAGATAGCGATGTGACCGCGATCGCTTGTCAAGAATC |
| | | CCAGTGATCCCGAACCATAGGAGAGGCAAGCTCAATGCTTGCCTCGTCTTGAGGACTA |
| | | TCTAGATGTCTGTGGAACGCACATTTATTGCCATCAAGCCCGATGGCGTTCAGCGGG |
| | | GTTTGGTCGGTACGATCATCGGCCGCTTTGAGCAAAAAGGCTTCAAACTGGTGGGCC |
| | | TAAAGCAGCTGAAGCCCAGTCGCGAGCTGGCCGAACAGCACTATGCTGTCCACCGC |
| | | GAGCGCCCCTTCTTCAATGGCCTCGTCGAGTTCATCACCTCTGGGCCGATCGTGGCG |

-continued

| SEQ ID NO | Description | Sequence |
|---|---|---|

ATCGTCTTGGAAGGCGAAGGCGTTGTGGCGGCTGCTCGCAAGTTGATCGGCGCTAC
CAATCCGCTGACGGCAGAACCGGGCACCATCCGTGGTGATTTTGGTGTCAATATTGG
CCGCAACATCATCCATGGCTCGGATGCAATCGAAACAGCACAACAGGAAATTGCTCT
CTGGTTTAGCCCAGCAGAGCTAAGTGATTGGACCCCCACGATTCAACCCTGGCTGTA
CGAATAAGGTCTGCATTCCTTCAGAGAGACATTGCCATGCCG

25          Linker          G₄SGGS(G₄S)₃

---

What is claimed is:

1. An engineered outer membrane vesicle (OMV) comprising a carbonic anhydrase (CA) polypeptide presented on the outer surface of the engineered OMV, wherein the engineered OMV is produced from engineered cyanobacteria *Synchronous* sp. comprising:
   a fusion protein comprising the CA polypeptide having the amino acid sequence of SEQ ID NO: 7 operably linked to a transmembrane protein having the amino acid sequence of any one of SEQ ID NOs: 8-12.

2. The engineered OMV of claim 1, wherein the CA polypeptide is operably linked to the transmembrane protein embedded in the membrane of the engineered OMV to form the fusion protein.

3. The engineered OMV of claim 1, wherein the fusion protein further comprises a linker connecting the CA polypeptide to the transmembrane protein.

4. The engineered OMV of claim 1, wherein the engineered OMV comprises at least about 10 CA polypeptide molecules presented on its outer surface.

5. An engineered host cell capable of producing an engineered outer membrane vesicle (OMV) comprising a carbonic anhydrase (CA) polypeptide presented on the outer surface of the OMV, wherein the engineered host cell is an engineered photosynthetic microorganism *Synchronous* sp. comprising a heterologous nucleic acid encoding a fusion protein, wherein the fusion protein comprises the CA polypeptide having the amino acid sequence of SEQ ID NO: 7 operably linked to a transmembrane protein having the amino acid sequence of any one of SEQ ID Nos: 8-12, and wherein the fusion protein is capable of being inserted into the outer membrane of the engineered host cell such that CA polypeptide is presented on the outer surface of the engineered host cell.

6. The engineered host cell of claim 5, wherein the fusion protein further comprises:
   a linker connecting the CA polypeptide to the transmembrane protein; and
   a signal peptide capable of targeting the fusion protein to the inner membrane of the engineered host cell.

7. The engineered host cell of claim 5, wherein the heterologous nucleic acid is present extrachromosomally or is integrated into the chromosome of the engineered host cell.

8. A method of producing an engineered OMV comprising:
   (a) culturing the engineered host cell according to claim 5 under conditions suitable for expression of the fusion protein; and
   (b) obtaining an OMV produced by the engineered host cell,
   thereby producing the engineered OMV.

9. The method of claim 8, wherein the engineered host cell is cultured in the presence of $CO_2$ and light, and wherein the method further comprises filtering the engineered OMV.

10. A nanocatalyst composition comprising the engineered OMV of claim 1.

11. The nanocatalyst composition of claim 10, comprising the engineered OMV at a concentration greater than about 100 mg/L or 10 g.

12. The nanocatalyst of claim 10, wherein the composition is not a therapeutic composition.

13. The engineered OMV of claim 3, wherein the linker is a peptide linker comprising the amino acid sequence of any one of SEQ ID NOs: 17-19 and 25.

14. The engineered OMV of claim 13, wherein the fusion protein further comprises a signal peptide capable of targeting the fusion protein to the inner membrane of the engineered host cell.

15. The engineered OMV of claim 14, wherein the signal peptide has the amino acid sequence of SEQ ID NO: 13.

16. The engineered OMV of claim 1, wherein the fusion protein has the amino acid sequence of any one of SEQ ID NOs: 1-6 and 21.

17. The engineered OMV of claim 1, wherein the fusion protein has the amino acid sequence of SEQ ID NO: 1.

18. The engineered host cell of claim 5, wherein the nucleic acid encoding the fusion protein has the nucleotide sequence of SEQ ID NO: 24.

* * * * *

SEQUENCE LISTING

Sequence total quantity: 25
SEQ ID NO: 1              moltype = AA   length = 776
FEATURE                  Location/Qualifiers
source                   1..776
                         mol_type = protein
                         note = synthetic sequence
                         organism = unidentified
SEQUENCE: 1
MKRHLNTCYR LVWNHMTGAF VVASELARAR GKRGGVAVAL SLAAVTSLPV LAGGGHVVKW   60
GYVGKIGPAH WGDLAHEYFM CKVGKNQSPV DINSSVTIEA QLEPINFHYR DQISGEIVNN   120
GHTIMVVPKE DNYIVVDGKK FHLKQFHFHS PSEHTVEGKY YLLELHFVHQ ADDGQLAVIG   180
VVFDRGAEHP EIAKLWKEAP EHEGKKELKS LVNMQALLPE NLDYYRYSGS LTTPPCSEGV   240
IWLFLKNPLQ ISEAQAEKFK KIMGFENNRP VQPVNARKIL KGSSSGSSPT NVTLASGATW   300
NIPDNATVQS VVDDLSHAGQ IHFTSTRTGK FVPATLKVKN LNGQNGTISL RVRPDMAQNN   360
ADRLVIDGGR ATGKTILNLV NAGNSASGLA TSGKGIQVVE AINGATTEEG AFVQGNRLQA   420
GAFNYSLNRD SDESWYLRSE NAYRAEVPLY ASMLTQAMDY DRIVAGSRSH QTGVNGENNS   480
VRLSIQGGHL GHDNNGGIAR GATPESSGSY GFVRLEGDLM RTEVAGMSVT AGVYGAAGHS   540
SVDVKDDDGS RAGTVRDDAG SLGGYLNLVH TSSGLWADIV AQGTRHSMKA SSDNNDFRAR   600
GWGWLGSLET GLPFSITDNL MLEPQLQYTW QGLSLDDGKD NAGYVKFGHG SAQHVRAGFR   660
LGSHNDMTFG EGTSSRAPLR DSAKHSVSEL PVNWWVQPSV IRTFSSRGDM RVGTSTAGSG   720
MTFSPSQNGT SLDLQAGLEA RVRENITLGV QAGYAHSVSG SSAEGYNGQA TLNVTF       776

SEQ ID NO: 2              moltype = AA   length = 751
FEATURE                  Location/Qualifiers
source                   1..751
                         mol_type = protein
                         note = synthetic sequence
                         organism = unidentified
SEQUENCE: 2
MKRLFSALLL APAIAGVAAG AANANGLGGG HVVKWGYVGK IGPAHWGDLA HEYFMCKVGK   60
NQSPVDINSS VTIEAQLEPI NFHYRDQISG EIVNNGHTIM VVPKEDNYIV VDGKKFHLKQ   120
FHFHSPSEHT VEGKYYLLEL HFVHQADDGQ LAVIGVVFDR GAEHPEIAKL WKEAPEHEGK   180
KELKSLVNMQ ALLPENLDYY RYSGSLTTPP CSEGVIWLFL KNPLQISEAQ AEKFKKIMGF   240
ENNRPVQPVN ARKILKGSSS GSSPTNVTLA SGATWNIPDN ATVQSVVDDL SHAGQIHFTS   300
TRTGKFVPAT LKVKNLNGQN GTISLRVRPD MAQNNADRLV IDGGRATGKT ILNLVNAGNS   360
ASGLATSGKG IQVVEAINGA TTEEGAFVQG NRLQAGAFNY SLNRDSDESW YLRSENAYRA   420
EVPLYASMLT QAMDYDRIVA GSRSHQTGVN GENNSVRLSI QGGHLGHDNN GGIARGATPE   480
SSGSYGFVRL EGDLMRTEVA GMSVTAGVYG AAGHSSVDVK DDDGSRAGTV RDDAGSLGGY   540
LNLVHTSSGL WADIVAQGTR HSMKASSDNN DFRARGWGWL GSLETGLPFS ITDNLMLEPQ   600
LQYTWQGLSL DDGKDNAGYV KFGHGSAQHV RAGFRLGSHN DMTFGEGTSS RAPLRDSAKH   660
SVSELPVNWW VQPSVIRTFS SRGDMRVGTS TAGSGMTFSP SQNGTSLDLQ AGLEARVREN   720
ITLGVQAGYA HSVSGSSAEG YNGQATLNVT F                                   751

SEQ ID NO: 3              moltype = AA   length = 1359
FEATURE                  Location/Qualifiers
source                   1..1359
                         mol_type = protein
                         note = synthetic sequence
                         organism = unidentified
SEQUENCE: 3
MNRIYSLRYS AVARGFIAVS EFARKCVHKS VRRLCFPVLL LIPVLFSAGS LAGGGGHVVK   60
WGYVGKIGPA HWGDLAHEYF MCKVGKNQSP VDINSSVTIE AQLEPINFHY RDQISGEIVN   120
NGHTIMVVPK EDNYIVVDGK KFHLKQFHFH SPSEHTVEGK YYLLELHFVH QADDGQLAVI   180
GVVFDRGAEH PEIAKLWKEA PEHEGKKELK SLVNMQALLP ENLDYYRYSG SLTTPPCSEG   240
VIWLFLKNPL QISEAQAEKF KKIMGFENNR PVQPVNARKI LKGSSSGSSN DAPVTFRTSE   300
GGALEWSFNS STGAGALTQG TTTYAMHGQQ GNDLNAGKNL IFGQGNGQIN LKDSVSQGAG   360
SLTFRDNYTV TTSNGSTWTG AGIVVDNGVS VNWQVNGVKG DNLHKIGEGT LTVQGTGINE   420
GGLKVGDGKV VLNQQADNKG QVQAFSSVNI ASGRPTVVLT DERQVNPDTV SWGYRGGTLD   480
VNGNSLTFHQ LKAADYGAVL ANNVDKRATI TLDYALRADK VALNGWSESG KGTAGNLYKY   540
NNPYTNTTDY FILKQSTYGY FPTDQSSNAT WEFVGHSQGD AQKLVADRFN TAGYLFHGQL   600
KGNLNVDNRL PEGVTGALVM DGAADISGTF TQENGRLTLQ GHPVIHAYNT QSVADKLAAS   660

```
GDHSVLTQPT SFSQEDWENR SFTFDRLSLK NTDFGLGRNA TLNTTIQADN SSVTLGDSRV    720
FIDKNDGQGT AFTLEEGTSV ATKDADKSVF NGTVNLDNQS VLNINDIFNG GIQANNSTVN    780
ISSDSAVLGN STLTSTALNL NKGANALASQ SFVSDGPVNI SDATLSLNSR PDEVSHTLLP    840
VYDYAGSWNL KGDDARLNVG PYSMLSGNIN VQDKGTVTLG GEGELSPDLT LQNQMLYSLF    900
NGYRNIWSGS LNAPDATVSM TDTQWSMNGN STAGNMKLNR TIVGFNGGTS PFTTLTTDNL    960
DAVQSAFVMR TDLNKADKLV INKSATGHDN SIWVNFLKKP SNKDTLDIPL VSAPEATADN   1020
LFRASTRVVG FSDVTPILSV RKEDGKKEWV LDGYQVARND GQGKAAATFM HISYNNFITE   1080
VGSLNKRMGD LRDINGEAGT WVRLLNGSGS ADGGFTDHYT LLQMGADRKH ELGSMDLFTG   1140
VMATYTDTDA SADLYSGKTK SWGGGFYASG LFRSGAYFDV IAKYIHNENK YDLNFAGAGK   1200
QNFRSHSLYA GAEVGYRYHL TDTTFVEPQA ELVWGRLQGQ TFNWNDSGMD VSMRRNSVNP   1260
LVGRTGVVSG KTFSGKDWSL TARAGLHYEF DLTDSADVHL KDAAGEHQIN GRKDSRMLYG   1320
VGLNARFGDN TRLGLEVERS AFGKYNTDDA INANIRYSF                         1359

SEQ ID NO: 4              moltype = AA  length = 611
FEATURE                   Location/Qualifiers
source                    1..611
                          mol_type = protein
                          note = synthetic sequence
                          organism = unidentified
SEQUENCE: 4
MKRLFSALLL APAIAGVAAG AANANGLSTE QLQKIDAVTP NGITSGQITS ITELSDVKPT    60
DWAYQALQSL VERYGCIVGY PDRTYRGSRP LSRYEFAAGL NACLDKVIEF AASKEDLDTL   120
KRLTEEFQAE LATLRGRVDS LEARVKELEA TRFSTTTKLQ GEVIFSLDAV ANTAGNERNQ   180
DGAVSFGNRV SLNLNTSFTG KDLLLTRLRA RNIETIQQRL SPGFNPSGSR LDYDGTGSPG   240
VPNSANTFFL DKLLYRFPVG DVSFTVGTAG VQPQDYGLSD ATFFSGPANT KAFKYVGAGV   300
YADTRDADTA GVGFNWKASK NFSFQAGYIN RNSADVSTVN SGGVFGFTPT GTGTNSWDVN   360
AQVKYQTDNN KFRVALAYAL RNGGGHVVKW GYVGKIGPAH WGDLAHEYFM CKVGKNQSPV   420
DINSSVTIEA QLEPINFHYR DQISGEIVNN GHTIMVVPKE DNYIVVDGKK FHLKQFHFHS   480
PSEHTVEGKY YLLELHFVHQ ADDGQLAVIG VVFDRGAEHP EIAKLWKEAP EHEGKKELKS   540
LVNMQALLPE NLDYYRYSGS LTTPPCSEGV IWLFLKNPLQ ISEAQAEKFK KIMGFENNRP   600
VQPVNARKIL K                                                       611

SEQ ID NO: 5              moltype = AA  length = 392
FEATURE                   Location/Qualifiers
source                    1..392
                          mol_type = protein
                          note = synthetic sequence
                          organism = Unidentified
SEQUENCE: 5
MTKLKLLALG VLIATSAGVA HAEGKFSLGA GVGVVEHPYK DYDTDVYPVP VINYEGDNFW    60
FRGLGGGYYL WNDATDKLSI TAYWSPLYFK AKDSGDHQMR HLDDRKSTMM AGLSYAHFTQ   120
YGYLRTTLAG DTLDNSNGIV GGGGSGGSGG GGSGGGGSGG GGSGGGHVVK WGYVGKIGPA   180
HWGDLAHEYF MCKVGKNQSP VDINSSVTIE AQLEPINFHY RDQISGEIVN NGHTIMVVNP   240
EDNYIVVDGK KFHLKQFHFH SPSEHTVEGK YYLLELHFVH QADDGQLAVI GVVFDRGAEH   300
PEIAKLWKEA PEHEGKKELK SLVNMQALLP ENLDYYRYSG SLTTPPCSEG VIWLFLKNPL   360
QISEAQAEKF KKIMGFENNR PVQPVNARKI LK                                392

SEQ ID NO: 6              moltype = AA  length = 473
FEATURE                   Location/Qualifiers
source                    1..473
                          mol_type = protein
                          note = synthetic sequence
                          organism = Unidentified
SEQUENCE: 6
MKYLLPTAAA GLLLLAAQPA MAMTLDKALV LRTCANNMAD HCGLIWPASG TVESRYWQST    60
RRHENGLVGL LWGAGTSAFL SVHADARWIV CEVAVADIIS LEEPGMVKFP RAEVVHVGDR   120
ISASHFISAR QADPASTSTS TSTSTLTPMP TAIPTPMPAV ASVTLPVAEQ ARHEVFDVAS   180
VSAAAAPVNT LPVTTPQNLQ TATYGSTLSG DNHSRLIAGY GSNETAGNHS DLIGGGGSGG   240
GHVVKWGYVG KIGPAHWGDL AHEYFMCKVG KNQSPVDINS SVTIEAQLEP INFHYRDQIS   300
GEIVNNGHTI MVVPKEDNYI VVDGKKFHLK QFHFHSPSEH TVEGKYYLLE LHFVHQADDG   360
QLAVIGVVFD RGAEHPEIAK LWKEAPEHEG KKELKSLVNM QALLPENLDY YRYSGSLTTP   420
PCSEGVIWLF LKNPLQISEA QAEKFKKIMG FENNRPVQPV NARILKHHHH HHH          473

SEQ ID NO: 7              moltype = AA  length = 229
FEATURE                   Location/Qualifiers
source                    1..229
                          mol_type = protein
                          note = synthetic sequence
                          organism = Unidentified
SEQUENCE: 7
GGGHVVKWGY VGKIGPAHWG DLAHEYFMCK VGKNQSPVDI NSSVTIEAQL EPINFHYRDQ    60
ISGEIVNNGH TIMVVPKEDN YIVVDGKKFH LKQFHFHSPS EHTVEGKYYL LELHFVHQAD   120
DGQLAVIGVV FDRGAEHPEI AKLWKEAPEH EGKKELKSLV NMQALLPENL DYYRYSGSLT   180
TPPCSEGVIW LFLKNPLQIS EAQAEKFKKI MGFENNRPVQ PVNARKILK               229

SEQ ID NO: 8              moltype = AA  length = 488
FEATURE                   Location/Qualifiers
source                    1..488
                          mol_type = protein
```

```
                           note = synthetic sequence
                           organism = unidentified
SEQUENCE: 8
PTNVTLASGA TWNIPDNATV QSVVDDLSHA GQIHFTSTRT GKFVPATLKV KNLNGQNGTI   60
SLRVRPDMAQ NNADRLVIDG GRATGKTILN LVNAGNSASG LATSGKGIQV VEAINGATTE  120
EGAFVQGNRL QAGAFNYSLN RDSDESWYLR SENAYRAEVP LYASMLTQAM DYDRIVAGSR  180
SHQTGVNGEN NSVRLSIQGG HLGHDNNGGI ARGATPESSG SYGFVRLEGD LMRTEVAGMS  240
VTAGVYGAAG HSSVDVKDDD GSRAGTVRDD AGSLGGYLNL VHTSSGLWAD IVAQGTRHSM  300
KASSDNNDFR ARGWGWLGSL ETGLPFSITD NLMLEPQLQY TWQGLSLDDG KDNAGYVKFG  360
HGSAQHVRAG FRLGSHNDMT FGEGTSSRAP LRDSAKHSVS ELPVNWWVQP SVIRTFSSRG  420
DMRVGTSTAG SGMTFSPSQN GTSLDLQAGL EARVRENITL GVQAGYAHSV SGSSAEGYNG  480
QATLNVTF                                                          488

SEQ ID NO: 9           moltype = AA   length = 1070
FEATURE                Location/Qualifiers
source                 1..1070
                       mol_type = protein
                       note = synthetic sequence
                       organism = Unidentified
SEQUENCE: 9
NDAPVTFRTS EGGALEWSFN SSTGAGALTQ GTTTYAMHGQ QGNDLNAGKN LIFQGQNGQI   60
NLKDSVSQGA GSLTFRDNYT VTTSNGSTWT GAGIVVDNGV SVNWQVNGVK GDNLHKIGEG  120
TLTVQGTGIN EGGLKVGDGK VVLNQQADNK GQVQAFSSVN IASGRPTVVL TDERQVNPDT  180
VSWGYRGGTL DVNGNSLTFH QLKAADYGAV LANNVDKRAT ITLDYALRAD KVALNGWSES  240
GKGTAGNLYK YNNPYTNTTD YFILKQSTYG YFPTDQSSNA TWEFVGHSQG DAQKLVADRF  300
NTAGYLFHGQ LKGNLNVDNR LPEGVTGALV MDGAADISGT FTQENGRLTL QGHPVIHAYN  360
TQSVADKLAA SGDHSVLTQP TSFSQEDWEN RSFTFDRLSL KNTDFGLGRN ATLNTTIQAD  420
NSSVTLGDSR VFIDKNDGQG TAFTLEEGTS VATKDADKSV FNGTVNLDNQ SVLNINDIFN  480
GGIQANNSTV NISSDSAVLG NSTLTSTALN LNKGANALAS QSFVSDGPVN ISDATLSLNS  540
RPDEVSHTLL PVYDYAGSWN LKGDDARLNV GPYSMLSGNI NVQDKGTVTL GGEGELSPDL  600
TLQNQMLYSL FNGYRNIWSG SLNAPDATVS MTDTQWSMNG NSTAGNMKLN RTIVGFNGGT  660
SPFTTLTTDN LDAVQSAFVM RTDLNKADKL VINKSATGHD NSIWVNFLKK PSNKDTLDIP  720
LVSAPEATAD NLFRASTRVV GFSDVTPILS VRKEDGKKEW VLDGYQVARN DGQGKAAATF  780
MHISYNNFIT EVGSLNKRMG DLRDINGEAG TWVRLLNGSG SADGGFTDHY TLLQMGADRK  840
HELGSMDLFT GVMATYTDTD ASADLYSGKT KSWGGGFYAS GLFRSGAYFD VIAKYIHNEN  900
KYDLNFAGAG KQNFRSHSLY AGAEVGYRYH LTDTTFVEPQ AELVWGRLQG QTFNWNDSGM  960
DVSMRRNSVN PLVGRTGVVS GKTFSGKDWS LTARAGLHYE FDLTDSADVH LKDAAGEHQI 1020
NGRKDSRMLY GVGLNARFGD NTRLGLEVER SAFGKYNTDD AINANIRYSF           1070

SEQ ID NO: 10          moltype = AA   length = 382
FEATURE                Location/Qualifiers
source                 1..382
                       mol_type = protein
                       note = synthetic sequence
                       organism = Unidentified
SEQUENCE: 10
MKRLFSALLL APAIAGVAAG AANANGLSTE QLQKIDAVTP NGITSGQITS ITELSDVKPT   60
DWAYQALQSL VERYGCIVGY PDRTYRGSRP LSRYEFAAGL NACLDKVIEF AASKEDLDTL  120
KRLTEEFQAE LATLRGRVDS LEARVKELEA TRFSTTTKLQ GEVIFSLDAV ANTAGNERNQ  180
DGAVSFGNRV SLNLNTSFTG KDLLLTRLRA RNIETIQQRL SPGFNPSGSR LDYDGTGSPG  240
VPNSANTFFL DKLLYRFPVG DVSFTVGTAG VQPQDYGLSD ATFFSGPANT KAFKYVGAGV  300
YADTRDADTA GVGFNWKASK NFSFQAGYIN RNSADVSTVN SGGVFGFTPT GTGTNSWDVN  360
AQVKYQTDNN KFRVALAYAL RN                                          382

SEQ ID NO: 11          moltype = AA   length = 140
FEATURE                Location/Qualifiers
source                 1..140
                       mol_type = protein
                       note = synthetic sequence
                       organism = Unidentified
SEQUENCE: 11
MTKLKLLALG VLIATSAGVA HAEGKFSLGA GVGVVEHPYK DYDTDVYPVP VINYEGDNFW   60
FRGLGGGYYL WNDATDKLSI TAYWSPLYFK AKDSGDHQMR HLDDRKSTMM AGLSYAHFTQ  120
YGYLRTTLAG DTLDNSNGIV                                             140

SEQ ID NO: 12          moltype = AA   length = 211
FEATURE                Location/Qualifiers
source                 1..211
                       mol_type = protein
                       organism = Unidentified
SEQUENCE: 12
MTLDKALVLR TCANNMADHC GLIWPASGTV ESRYWQSTRR HENGLVGLLW GAGTSAFLSV   60
HADARWIVCE VAVADIISLE EPGMVKFPRA EVVHVGDRIS ASHFISARQA DPASTSTSTS  120
TSTLTPMPTA IPTPMPAVAS VTLPVAEQAR HEVFDVASVS AAAAPVNTLP VTTPQNLQTA  180
TYGSTLSGDN HSRLIAGYGS NETAGNHSDL I                                211

SEQ ID NO: 13          moltype = AA   length = 52
FEATURE                Location/Qualifiers
source                 1..52
```

```
                           mol_type = protein
                           organism = Unidentified
SEQUENCE: 13
MKRHLNTCYR LVWNHMTGAF VVASELARAR GKRGGVAVAL SLAAVTSLPV LA        52

SEQ ID NO: 14             moltype = AA  length = 27
FEATURE                   Location/Qualifiers
source                    1..27
                          mol_type = protein
                          organism = unidentified
SEQUENCE: 14
MKRLFSALLL APAIAGVAAG AANANGL                                    27

SEQ ID NO: 15             moltype = AA  length = 22
FEATURE                   Location/Qualifiers
source                    1..22
                          mol_type = protein
                          organism = unidentified
SEQUENCE: 15
MKYLLPTAAA GLLLLAAQPA MA                                         22

SEQ ID NO: 16             moltype = AA  length = 53
FEATURE                   Location/Qualifiers
source                    1..53
                          mol_type = protein
                          organism = Unidentified
SEQUENCE: 16
MNRIYSLRYS AVARGFIAVS EFARKCVHKS VRRLCFPVLL LIPVLFSAGS LAG       53

SEQ ID NO: 17             moltype = AA  length = 7
FEATURE                   Location/Qualifiers
source                    1..7
                          mol_type = protein
                          organism = Unidentified
SEQUENCE: 17
GSSSGSS                                                          7

SEQ ID NO: 18             moltype = AA  length = 5
FEATURE                   Location/Qualifiers
source                    1..5
                          mol_type = protein
                          organism = Unidentified
SEQUENCE: 18
GGGGS                                                            5

SEQ ID NO: 19             moltype = AA  length = 23
FEATURE                   Location/Qualifiers
source                    1..23
                          mol_type = protein
                          organism = Unidentified
SEQUENCE: 19
GGGGSGGSGG GGSGGGGSGG GGS                                        23

SEQ ID NO: 20             moltype = AA  length = 1038
FEATURE                   Location/Qualifiers
source                    1..1038
                          mol_type = protein
                          organism = Unidentified
SEQUENCE: 20
MKRHLNTCYR LVWNHMTGAF VVASELARAR GKRGGVAVAL SLAAVTSLPV LAADIVVHPG   60
ETVNGGTLAN HDNQIVFGTT NGMTISTGLE YGPDNEANTG GQWVQDGGTA NKTTVTSGGL   120
QRVNPGGSVS DTVISAGGGQ SLQGRAVNTT LNGGEQWMHE GAIATGTVIN DKGWQVVKPG   180
TVATDTVVNT GAEGGPDAEN GDTGQFVRGD AVRTTINKNG RQIVRAEGTA NTTVVYAGGD   240
QTVHGHALDT TLNGGYQYVH NGGTASDTVV NSDGWQIVKN GGVAGNTTVN QKGRLQVDAG   300
GTATNVTLKQ GGALVTSTAA TVTGINRLGA FSVVEGKADN VVLENGGRLD VLTGHTATNT   360
RVDDGGTLDV RNGGTATTVS MGNGGVLLAD SGAAVSGTRS DGKAFSIGGG QADALMLEKG   420
SSFTLNAGDT ATDTTVNGGL FTARGGTLAG TTTLNNGAIL TLSGKTVNND TLTIREGDAL   480
LQGGGSLTGNG SVEKSGSGTL TVSNTTLTQK AVNLNEGTLT LNDSTVTTDV IAQRGTALKL   540
TGSTVLNGAI DPTNVTLASG ATWNIPDNAT VQSVVDDLSH AGQIHFTSTR TGKFVPATLK   600
VKNLNGQNGT ISLRVRPDMA QNNADRLVID GGRATGKTIL NLVNAGNSAS GLATSGKGIQ   660
VVEAINGATT EEGAFVQGNR LQAGAFNYSL NRDSDESWYL RSENAYRAEV PLYASMLTQA   720
MDYDRIVAGS RSHQTGVNGE NNSVRLSIQG GHLGHDNNGG IARGATPESS GSYGFVRLEG   780
DLMRTEVAGM SVTAGVYGAA GHSSVDVKDD DGSRAGTVRD DAGSLGGYLN LVHTSSGLWA   840
DIVAQGTRHS MKASSDNNDF RARGWGWLGS LETGLPFSIT DNLMLEPQLQ YTWQGLSLDD   900
GKDNAGYVKF GHGSAQHVRA GFRLGSHNDM TFGEGTSSRA PLRDSAKHSV SELPVNWWVQ   960
PSVIRTFSSR GDMRVGTSTA GSGMTFPSQ NGTSLDLQAG LEARVRENIT LGVQAGYAHS   1020
VSGSSAEGYN GQATLNVT                                              1038

SEQ ID NO: 21             moltype = AA  length = 784
```

```
FEATURE             Location/Qualifiers
source              1..784
                    mol_type = protein
                    organism = Unidentified
SEQUENCE: 21
MKRHLNTCYR LVWNHMTGAF VVASELARAR GKRGGVAVAL SLAKKFIGGL VGSLMIGGVA   60
LAGGGHVVKW GYVGKIGPAH WGDLAHEYFM CKVGKNQSPV DINSSVTIEA QLEPINFHYR  120
DQISGEIVNN GHTIMVVPKE DNYIVVDGKK FHLKQFHFHS PSEHTVEGKY YLLELHFVHQ  180
ADDGQLAVIG VVFDRGAEHP EIAKLWKEAP EHEGKKELKS LVNMQALLPE NLDYYRYSGS  240
LTTPPCSEGV IWLFLKNPLQ ISEAQAEKFK KIMGFENNRP VQPVNARKIL KGSSSGSSTN  300
VTLASGATWN IPDNATVQSV VDDLSHAGQI HFTSTRTGKF VPATLKVKNL NGQNGTISLR  360
VRPDMAQNNA DRLVIDGGRA TGKTILNLVN AGNSASGLAT SGKGIQVVEA INGATTEEGA  420
FVQGNRLQAG AFNYSLNRDS DESWYLRSEN AYRAEVPLYA SMLTQAMDYD RIVAGSRSHQ  480
TGVNGENNSV RLSIQGGHLG HDNNGGIARG ATPESSGSYG FVRLEGDLMR TEVAGMSVTA  540
GVYGAAGHSS VDVKDDDGSR AGTVRDDAGS LGGYLNLVHT SSGLWADIVA QGTRHSMKAS  600
SDNNDFRARG WGWLGSLETG LPFSITDNLM LEPQLQYTWQ GLSLDDGKDN AGYVKFGHGS  660
AQHVRAGFRL GSHNDMTFGE GTSSRAPLRD SAKHSVSELP VNWWVQPSVI RTFSSRGDMR  720
VGTSTAGSGM TFSPSQNGTS LDLQAGLEAR VRENITLGVQ AGYAHSVSGS SAEGYNGQAT  780
LNVT                                                               784

SEQ ID NO: 22      moltype = AA  length = 43
FEATURE             Location/Qualifiers
source              1..43
                    mol_type = protein
                    organism = Unidentified
SEQUENCE: 22
MKRHLNTCYR LVWNHMTGAF VVASELARAR GKRGGVAVAL SLA                     43

SEQ ID NO: 23      moltype = AA  length = 487
FEATURE             Location/Qualifiers
source              1..487
                    mol_type = protein
                    organism = Unidentified
SEQUENCE: 23
PTNVTLASGA TWNIPDNATV QSVVDDLSHA GQIHFTSTRT GKFVPATLKV KNLNGQNGTI   60
SLRVRPDMAQ NNADRLVIDG GRATGKTILN LVNAGNSASG LATSGKGIQV VEAINGATTE  120
EGAFVQGNRL QAGAFNYSLN RDSDESWYLR SENAYRAEVP LYASMLTQAM DYDRIVAGSR  180
SHQTGVNGEN NSVRLSIQGG HLGHDNNGGI ARGATPESSG SYGFVRLEGD LMRTEVAGMS  240
VTAGVYGAAG HSSVDVKDDD GSRAGTVRDD AGSLGGYLNL VHTSSGLWAD IVAQGTRHSM  300
KASSDNNDFR ARGWGWLGSL ETGLPFSITD NLMLEPQLQY TWQGLSLDDG KDNAGYVKFG  360
HGSAQHVRAG FRLGSHNDMT FGEGTSSRAP LRDSAKHSVS ELPVNWWVQP SVIRTFSSRG  420
DMRVGTSTAG SGMTFSPSQN GTSLDLQAGL EARVRENITL GVQAGYAHSV SGSSAEGYNG  480
QATLNVT                                                            487

SEQ ID NO: 24      moltype = DNA  length = 6795
FEATURE             Location/Qualifiers
source              1..6795
                    mol_type = other DNA
                    organism = Unidentified
SEQUENCE: 24
ctggtttggct tggtttcatc agccatccgc ttgccctcat ctgttacgcc ggcggtagcc   60
ggccagcctc gcagagcagg attcccgttg agcaccgcca ggtgcgaata agggacagtg  120
aagaaggaac acccgctcgc gggtgggcct acttcaccta tcctgcccgg ctgacgccgt  180
tggatacacc aaggaaagtc tacacgaacc ctttggcaaa atcctgtata tcgtgcgaaa  240
aaggatggat ataccgaaaa aatcgctata atgaccccga gacagggtta tgcagcggaa  300
gatcgataat ctcatgacca aaatcccta acgtgagttt tcgttccact gagcgtcaga  360
ccccgtataa aagatcaaag gatcttcttg agatcctttt tttctgcgcg taatctgctg  420
cttgcaaaca aaaaaaccac cgctaccagc ggtggtttgt ttgccggatc aagagctacc  480
aactcttttt ccgaaggtaa ctggcttcag cagagcgcag ataccaaata ctgttcttct  540
agtgtagccg tagttaggcc accacttcaa gaactctgta gcaccgccta cataccctcgc  600
tctgctaatc ctgttaccag tggctgctgc cagtggcgat aagtcgtgtc ttaccgggtt  660
ggactcaaga cgatagttac cggataaggc gcagcggtcg gctgaacgg ggggttcgtg  720
cacacagccc agcttggagc gaacgaccta caccgaactg agatacctac agcgtgagct  780
atgagaaagc gccacgcttc ccgaaggag aaaggcggac aggtatccgg taagcggcag  840
ggtcggaaca ggagagcgca cgagggagct tccaggggga aacgcctggt atctttatag  900
tcctgtcggg tttcgccacc tctgacttga gcgtcgattt ttgtgatgct cgtcaggggg  960
gcggagccta tggaaaaacg ccagcaacgc ggcctttta cggttcctgg cctttttgctg 1020
gccttttgct cacatgtgtg ctgggcccca atgccttctc caagggcgac attccctga  1080
ctgttgaagg cgttgccaat atcaagattg ctggggaaga accgaccatc cacaacgcga 1140
tcgagcggct gcttggcaaa aaccgtaagg aaatcgagca aattgccaag agaccctcg  1200
aaggcaactt cgctggtgtt ttagccagcc tcacgccgga gcagatcaac gaggacaaaa 1260
ttgcctttgc caaaagtctg ctggaagagg cggaggatga ccttgagcag ctgggtcaag 1320
tcctcgatac gctgcaagtc cagaacattt ccgatgaggt cggttatctc tcggctagtg 1380
gacgcagcga gcgggctgat ctgcagcgag atgcccgaat tgctgaagcc gatgcccgag 1440
ctgcctctgc gatccaaacg gccgaaaatg acaagatcac ggccctgcgt cggatcgatc 1500
gcgatgtagc gatcgcccaa gccgaggccg agcgccggat tcaggatgcg ttgacgcggc 1560
gcgaagcggt ggtggccgaa gctgaagcgg acattgctac cgaagtcgct cgtagccaag 1620
cagaactccc tgtgcagcag gagcggatca aacaggtgca gcagcaactt caagccgatg 1680
tgatcgcccc agctgaggca gcttgtaaac gggcgatcgc ggaagcgcgg ggggccgccg 1740
```

-continued

```
cccgtatcgt cgaagatgga aaagctcaag cggaagggac ccaacgctg gcggaggctt    1800
ggcagaccgc tggtgctaat gcccgcgaca tcttcctgct ccagaagtct agataatccc    1860
tagcgatcgc aagtccaaag gttgtctaca atcaatatcc aagcatcaaa aagcgcccca    1920
ttcgaggcgc tttttgatta ttcagactgc tgtaattccg gcaattaggt tatttgccga    1980
ctaccttggt gatctcgcct ttcacgtagt ggacaaattc ttccaactga tctgcgcgcg    2040
aggccaagcg atcttcttct tgtccaagat aagcctgtct agcttcaagt atgacgggct    2100
gatactgggc cggcaggcgc tccattgccc agtcggcagc gacatccttc ggcgcgattt    2160
tgccggttac tgcgctgtac caaatgcggg acaacgtaag cactacattt cgctcatcgc    2220
cagcccagtc gggcggcgag ttccatagcg ttaaggtttc atttagcgcc tcaaatagat    2280
cctgttcagg aaccggatca aagagttcct ccgccgctgg acctaccaag gcaacgctat    2340
gttctcttgc ttttgtcagc aagatagcca gatcaatgtc gatcgtggct ggctcgaaga    2400
taccagcaag aatgtcattg cgctgccatt ctccaaattg cagttcgcgc ttagctggat    2460
aacgccacgg aatgatgtcg tcgtgcacaa caatggtgac ttctacagcg cggagaatct    2520
cgctctctcc aggggaagcc gaagtttcca aaaggtcgtt gatcaaagct cgccgcgttg    2580
tttcatcaag ccttacggtc accgtaacca gcaaatcaat atcactgtgt ggcttcaggc    2640
cgccatccac tgcggagccg tacaaatgta cggccagcaa cgtcggttcg agatggcgct    2700
cgatgacgcc aactacctct gatagttgag tcgatacttc ggcgatcacc gcttccctca    2760
taatgtttaa ctttgtttta gggcgactgc cctgctgcgt aacatcgttg ctgctccata    2820
acatcaaaca tcgacccacg gcgtaacgcg cttgctgctt ggatgcccga ggcatagact    2880
gtaccccaaa aaaacagtca taacaagcca tgaaaaccgc cactgcgccg ttaccaccgc    2940
tgcgttcggt caaggttctg gaccagttgc gtgagcgcat acgctacttg cattacagct    3000
tacgaaccga acaggcttat gtccactggg ttcgtgcctt catccgtttc cacggtgtgc    3060
gtcaccggc aaccttgggg agcagcgaag tcgaggcatt tctgtcctgg ctggctattt    3120
agcgtcttct aatccagtgt agacagtagt tttggctccg ttgagcactg tagccttggg    3180
cgatcgctct aaacattaca taaattcaca aagttttcgt tacataaaaa tagtgtctac    3240
ttagctaaaa attaagggtt ttttacacct ttttgacagt taatctccta gcctaaaaag    3300
caagagtttt taactaagac tcttgccctt tacaacctcg aaggagcgtc agatctcata    3360
tgaaacgcca cctgaacacc tgctaccgcc tggtgtggaa ccacatgacc ggcgcctttg    3420
tggtggccag cgaactggcc cgcgcccgcg gcaaacgcgg cggcgtggcc gtggccctga    3480
gcctggccgc cgtgaccagc ctgcccgtgc tggccgggcg cggccacgtg gtgaaatgga    3540
gctacgtggg caaaatcggc cccgcccact ggggcgatct ggcccacgaa tactttatgt    3600
gcaaagtggg caaaaaccag agcccgtgg atatcaacag cagcgtgacc atcgaagccc    3660
agctggaacc catcaacttt cactaccgcg atcagatcg cggcgaaatc gtgaacaacg    3720
gccacaccat catggtggtg cccaaagaag ataactacat cgtggtggat ggcaaaaaat    3780
ttcacctgaa acagtttcac tttcacagcc ccagcgaaca caccgtggaa ggcaaatact    3840
acctgctgga actgcacttt gtgcaccagg ccgatgatgg ccagctggcc gtgatcggcg    3900
tggtgtttga tcgcggcgcc gaacaccccg aaatcgccaa actgtggaaa gaagcccccg    3960
aacacgaagg caaaaaagaa ctgaaaagcc tggtgaacat gcaggccctg ctgcccgaaa    4020
acctggatta ctaccgctac agcggcagcc tgaccacccc ccctgcagc gaaggcgtga    4080
tctggctgtt tctgaaaaac cccctgcaga tcagcgaagc ccaggccgaa aaatttaaaa    4140
aaatcatggg cctttgaaaac aaccgccccg tgcagcccgt gaacgcccgc aaaatcctga    4200
aaggcagcag cagcggcagc agccccacca acgtgaccct ggccagcggc gccacctgga    4260
acatccccga taacgccacc gtgcagagcg tggtggatga tctgagccac gccggccaga    4320
tccactttac cagcacccgc accggcaaat ttgtgcccgc caccctgaaa gtgaaaaacc    4380
tgaacggcca gaacggcacc atcagcctgc gcgtgcgccc cgatatggcc cagaacaacg    4440
ccgatcgcct ggtgatcgat ggcggccgcg ccaccggcaa aaccatcctg aacctggtga    4500
acgccggcaa cagcgccagc ggcctggcca ccagcgacaa gtggtggaag cctctgtgca    4560
ccatcaacgg cgccaccacc gaagaaggcg cctttgtgca gggcaaccgc ctgcaggccg    4620
cgcgcctttaa ctacagcctg aaccgcgata gcgatgaaag ctggtacctg cgcagcgaaa    4680
acgcctaccg cgccgaagtg cccctgtacg ccagcatgct gacccaggcc atggattacg    4740
atcgcatcgt ggccggcagc cgcagccacc agaccgggt gaacggcgaa aacaacagcg    4800
tgcgcctgag catccagggc ggccacctgg gccacgataa caacggcggc atcgcccgcg    4860
gcgccacccc cgaaagcagc ggcagctacg gctttgtgcg cctggaaggc gatctgatgc    4920
gcaccgaagt ggccggcatg agcgtgaccg ccggcgtgta cggcgccgcc ggccacagca    4980
gcgtggatgt gaaagatgat gatggcagcc gcgccgacgc cgtgcgcgat gatgccggca    5040
gcctgggcgg ctacctgaac ctggtgcaca ccagcagcgg cctgtgggcc gatatcgtgg    5100
cccagggcac ccgccacagc atgaaagcca gcagcgataa caacgatttt cgcgcccgcg    5160
gctggggctg gctgggcagc ctggaaaccg gcctgcccctt tagcatcacc gataacctga    5220
tgctggaacc ccagctgcag tacacctggc agggcctgag cctggatgat ggcaaagata    5280
acgccggcta cgtgaaattt ggccacggca gcgccggtgc cgtgcgtgcc ggctttcgcc    5340
tgggcagcca caacgatatg acctttggcg aaggcaccag cagccgcgcc cccctgcgcg    5400
atagcgccaa acacagcgtg agcgaactgc ccgtgaactg gtgggtgcag cccagcgtga    5460
tccgcacctt tagcagccgc ggcgatatgc gcgtgggcac cagcaccgcc ggcagcggca    5520
tgacctttag ccccagccag aacggcacca gcctggatct gaccagccgg ctggaacgtc    5580
gcgtgcgcga aaacatcacc ctgggcgtgc aggccggcta cgcccacagc gtgagcggca    5640
gcagcgcgca aggctacaac ggccaggcca ccctgaacgt gaccttttaa catatgcacc    5700
accaccatca ccacgaaaac ctgtactttc agggcaagct tcgaattccc ggatccgcgg    5760
taccaggcaa acccatcccc aacccctgc tgggcctgga tagcaccggt ggtggtcacc    5820
accaccatca ccactagagt actgtatgca tcgagtgcct gcggcagta gcgcggtggt    5880
cccacctgac cccatgccga actcagaagt gaaacgccgt agcgccgatg gtagtgtgga    5940
gtctccccat gcgagagtag ggaactgcca ggcatcaaat aaaacgaaag gctcagtcga    6000
aagactgggc cttctcgagt ccctgctcgt cacgctttca ggcaccgtgc cagatatcga    6060
cgtggagtcg atcactgtga ttggcgaagg ggaaggcagc gctacccaaa tcgctagctt    6120
gctggagaag ctgaaacaaa ccacgggcat tgatctgacg aaatccctac cgggtcaatc    6180
cgactcgccc gctgcgaagt cctaagagat agcgatgtga ccgcgatcgc ttgtcaagaa    6240
tcccagtgat cccgaaccat aggaaggcaa gctcaatgct tgcctcgtct tgaggactat    6300
ctagatgtct gtggaacgca catttattgc catcaagccc gatggcgttc agcggggttt    6360
ggtcggtacg atcatcggcc gctttgagca aaaaggcttc aaactggtgg gcctaaagca    6420
gctgaagccc agtcgcgagc tggccgaaca gcactatgct gtccaccgcg agcgcccctt    6480
```

-continued

```
cttcaatggc ctcgtcgagt tcatcacctc tgggccgatc gtggcgatcg tcttggaagg   6540
cgaaggcgtt gtggcggctg ctcgcaagtt gatcggcgct accaatccgc tgacggcaga   6600
accgggcacc atccgtggtg attttggtgt caatattggc cgcaacatca tccatggctc   6660
ggatgcaatc gaaacagcac aacaggaaat tgctctctgg tttagcccag cagagctaag   6720
tgattggacc cccacgattc aaccctggct gtacgaataa ggtctgcatt ccttcagaga   6780
gacattgcca tgccg                                                     6795

SEQ ID NO: 25          moltype = AA  length = 23
FEATURE                Location/Qualifiers
source                 1..23
                       mol_type = protein
                       organism = Unidentified
SEQUENCE: 25
GGGGSGGSGG GGSGGGGSGG GGS                                             23
```